(12) United States Patent
Rogers et al.

(10) Patent No.: US 11,029,198 B2
(45) Date of Patent: Jun. 8, 2021

(54) ALTERNATIVE APPROACH FOR UV SENSING

(71) Applicant: THE BOARD OF TRUSTEES OF THE UNIVERSITY OF ILLINOIS, Urbana, IL (US)

(72) Inventors: John A. Rogers, Wilmette, IL (US); Anthony R. Banks, Savoy, IL (US); Xinying Wang, Savoy, IL (US); Gregory Brown, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 15/578,617

(22) PCT Filed: Jun. 1, 2016

(86) PCT No.: PCT/US2016/035331
§ 371 (c)(1),
(2) Date: Nov. 30, 2017

(87) PCT Pub. No.: WO2016/196673
PCT Pub. Date: Dec. 8, 2016

(65) Prior Publication Data
US 2018/0274973 A1   Sep. 27, 2018

Related U.S. Application Data

(60) Provisional application No. 62/169,308, filed on Jun. 1, 2015, provisional application No. 62/169,983, filed
(Continued)

(51) Int. Cl.
*G01J 1/42* (2006.01)
*A61B 5/00* (2006.01)
(Continued)

(52) U.S. Cl.
CPC .............. *G01J 1/42* (2013.01); *A61B 5/6826* (2013.01); *G01J 1/429* (2013.01); *G01J 5/10* (2013.01);
(Continued)

(58) Field of Classification Search
CPC ..... G01J 1/42; G01J 1/429; G01J 5/10; A61B 5/6826; A61B 5/14552; A61B 2560/0214;
(Continued)

(56) References Cited

U.S. PATENT DOCUMENTS 3,949,410 A   4/1976   Bassous
4,058,418 A   11/1977   Lindmayer
(Continued)

FOREIGN PATENT DOCUMENTS

DE   202004015373   2/2005
WO   WO 98/049936   11/1998
(Continued)

OTHER PUBLICATIONS

Mims III, F. M., "How to Use LEDs to Detect Light", makezine.com, retrieved from the Internet Archive Wayback Machine, dated Dec. 20, 2013 (Year: 2013).*
(Continued)

*Primary Examiner* — Blake C Riddick
(74) *Attorney, Agent, or Firm* — Leydig, Voit & Mayer, Ltd.

(57) ABSTRACT

The invention provides systems and methods for wearable and tissue-mounted electronics for monitoring exposure of a subject or object to electromagnetic radiation, particularly electromagnetic radiation in the visible, ultraviolet and infrared portions of the electromagnetic spectrum. In some embodiments, the devices are purely passive devices where absorption of incident electromagnetic radiation by the device provides at least a portion of the power for the
(Continued)

measurement of the radiant exposure or flux of the incident electromagnetic radiation. Devices of the invention may include near field communication components, for example, for enabling readout by an external device, such as a computer or mobile device.

23 Claims, 65 Drawing Sheets

Related U.S. Application Data on Jun. 2, 2015, provisional application No. 62/218,345, filed on Sep. 14, 2015, provisional application No. 62/218,321, filed on Sep. 14, 2015.

(51) Int. Cl.
*G06K 19/07* (2006.01)
*H02J 50/30* (2016.01)
*G01J 5/10* (2006.01)
*G06K 19/077* (2006.01)
*A61B 5/1455* (2006.01)
*A61B 6/10* (2006.01)
*A61B 6/00* (2006.01)

(52) U.S. Cl.
CPC ..... *G06K 19/0716* (2013.01); *G06K 19/0723* (2013.01); *G06K 19/07722* (2013.01); *H02J 50/30* (2016.02); *A61B 5/14552* (2013.01); *A61B 6/107* (2013.01); *A61B 6/542* (2013.01); *A61B 2560/0214* (2013.01); *A61B 2560/0242* (2013.01); *A61B 2562/028* (2013.01); *A61B 2562/0271* (2013.01)

(58) Field of Classification Search
CPC .... A61B 2560/0242; A61B 2562/0271; A61B 2562/028; G01K 19/0716; G01K 19/0723; G01K 19/07722
USPC ................... 250/336.1, 370.01, 370.07, 372
See application file for complete search history.

(56) References Cited

U.S. PATENT DOCUMENTS

| | | |
|---|---|---|
| 4,392,451 A | 7/1983 | Mickelsen et al. |
| 4,471,003 A | 9/1984 | Cann |
| 4,487,162 A | 12/1984 | Cann |
| 4,663,828 A | 5/1987 | Hanak |
| 4,715,235 A | 12/1987 | Fukui et al. |
| 4,761,335 A | 8/1988 | Aurichio et al. |
| 4,766,670 A | 8/1988 | Gazdik et al. |
| 4,784,720 A | 11/1988 | Douglas |
| 4,855,017 A | 8/1989 | Douglas |
| 5,041,973 A | 8/1991 | Lebron et al. |
| 5,086,785 A | 2/1992 | Gentile et al. |
| 5,118,400 A | 6/1992 | Wollam |
| 5,178,957 A | 1/1993 | Kolpe et al. |
| 5,204,144 A | 4/1993 | Cann et al. |
| 5,313,094 A | 5/1994 | Beyer et al. |
| 5,316,017 A | 5/1994 | Edwards et al. |
| 5,320,967 A * | 6/1994 | Avallone ............... F22B 37/421 122/504 |
| 5,339,180 A | 8/1994 | Katoh |
| 5,403,700 A | 4/1995 | Heller et al. |
| 5,427,096 A | 6/1995 | Bogusiewicz et al. |
| 5,434,751 A | 7/1995 | Cole, Jr. et al. |
| 5,455,178 A | 10/1995 | Fattnger |
| 5,469,845 A | 11/1995 | Delonzor et al. |
| 5,501,893 A | 3/1996 | Laermer et al. |
| 5,525,815 A | 6/1996 | Einset |
| 5,545,291 A | 8/1996 | Smith et al. |
| 5,625,471 A | 4/1997 | Smith |
| 5,648,148 A | 7/1997 | Simpson |
| 5,678,737 A | 10/1997 | White |
| 5,687,737 A | 11/1997 | Branham et al. |
| 5,691,245 A | 11/1997 | Bakhit |
| 5,753,529 A | 5/1998 | Chang et al. |
| 5,757,081 A | 5/1998 | Chang et al. |
| 5,767,578 A | 6/1998 | Chang et al. |
| 5,772,905 A | 6/1998 | Chou |
| 5,783,856 A | 7/1998 | Smith et al. |
| 5,790,151 A | 8/1998 | Mills |
| 5,817,242 A | 10/1998 | Biebuyck et al. |
| 5,824,186 A | 10/1998 | Smith et al. |
| 5,904,545 A | 5/1999 | Smith et al. |
| 5,907,189 A | 5/1999 | Mertol |
| 5,915,180 A | 6/1999 | Hara et al. |
| 5,917,534 A | 6/1999 | Rajeswaran |
| 5,928,001 A | 7/1999 | Gilette et al. |
| 5,955,781 A | 9/1999 | Joshi et al. |
| 5,976,683 A | 11/1999 | Liehrr et al. |
| 5,998,291 A | 12/1999 | Bakhit et al. |
| 6,024,702 A | 2/2000 | Iverson |
| 6,057,212 A | 5/2000 | Chan et al. |
| 6,080,608 A | 6/2000 | Nowak |
| 6,097,984 A | 8/2000 | Douglas |
| 6,165,391 A | 12/2000 | Vedamuttu |
| 6,171,730 B1 | 1/2001 | Kuroda et al. |
| 6,225,149 B1 | 5/2001 | Gan et al. |
| 6,236,883 B1 | 5/2001 | Ciaccio et al. |
| 6,265,326 B1 | 7/2001 | Ueno |
| 6,267,775 B1 | 8/2001 | Schulte |
| 6,274,508 B1 | 8/2001 | Jacobsen et al. |
| 6,276,775 B1 | 8/2001 | Schulte |
| 6,277,712 B1 | 8/2001 | Kang et al. |
| 6,281,038 B1 | 8/2001 | Jacobsen et al. |
| 6,284,418 B1 | 9/2001 | Trantolo |
| 6,291,896 B1 | 9/2001 | Smith |
| 6,316,278 B1 | 11/2001 | Jacobsen et al. |
| 6,316,283 B1 | 11/2001 | Saurer |
| 6,317,175 B1 | 11/2001 | Salerno et al. |
| 6,322,895 B1 | 11/2001 | Canham |
| 6,334,960 B1 | 1/2002 | Wilson et al. |
| 6,380,729 B1 | 4/2002 | Smith |
| 6,403,397 B1 | 6/2002 | Katz |
| 6,413,790 B1 | 6/2002 | Duthaler et al. |
| 6,417,025 B1 | 7/2002 | Gengel |
| 6,420,266 B1 | 7/2002 | Smith et al. |
| 6,433,401 B1 | 8/2002 | Clark et al. |
| 6,451,191 B1 | 9/2002 | Bentsen et al. |
| 6,459,418 B1 | 10/2002 | Comiskey et al. |
| 6,468,638 B2 | 10/2002 | Jacobsen et al. |
| 6,479,395 B1 | 11/2002 | Smith et al. |
| 6,487,906 B1 | 12/2002 | Hock |
| 6,517,995 B1 | 2/2003 | Jacobson et al. |
| 6,555,408 B1 | 4/2003 | Jacobsen et al. |
| 6,527,964 B1 | 5/2003 | Smith et al. |
| 6,559,905 B1 | 5/2003 | Akiyama |
| 6,566,744 B2 | 5/2003 | Gengel |
| 6,580,151 B2 | 6/2003 | Vandeputte et al. |
| 6,586,338 B2 | 7/2003 | Smith et al. |
| 6,590,346 B1 | 7/2003 | Hadley et al. |
| 6,606,079 B1 | 8/2003 | Smith |
| 6,606,247 B2 | 8/2003 | Credelle et al. |
| 6,608,370 B1 | 8/2003 | Chen et al. |
| 6,615,074 B2 | 9/2003 | Mickle et al. |
| 6,623,579 B1 | 9/2003 | Smith et al. |
| 6,639,578 B1 | 10/2003 | Comiskey et al. |
| 6,655,286 B2 | 12/2003 | Rogers |
| 6,657,289 B1 | 12/2003 | Craig et al. |
| 6,661,037 B2 | 12/2003 | Pan et al. |
| 6,665,044 B1 | 12/2003 | Jacobsen et al. |
| 6,666,821 B2 | 12/2003 | Keimel |
| 6,676,600 B1 * | 1/2004 | Conero ................... A61B 5/00 600/438 |
| 6,683,663 B1 | 1/2004 | Hadley et al. |
| 6,693,384 B1 | 2/2004 | Vicentini et al. |
| 6,706,402 B2 | 3/2004 | Rueckes et al. |
| 6,720,469 B1 | 4/2004 | Curtis et al. |
| 6,723,576 B2 | 4/2004 | Nozawa et al. |
| 6,730,990 B2 | 5/2004 | Kondo et al. |

(56) References Cited

U.S. PATENT DOCUMENTS

| | | |
|---|---|---|
| 6,731,353 B1 | 5/2004 | Credelle et al. |
| 6,743,982 B2 | 6/2004 | Biegelsen et al. |
| 6,780,696 B1 | 8/2004 | Schatz |
| 6,784,450 B2 | 8/2004 | Pan et al. |
| 6,814,898 B1 | 11/2004 | Deeman et al. |
| 6,816,380 B2 | 11/2004 | Credelle et al. |
| 6,844,673 B1 | 1/2005 | Bernkopf |
| 6,848,162 B2 | 2/2005 | Arneson et al. |
| 6,850,312 B2 | 2/2005 | Jacobsen et al. |
| 6,856,830 B2 | 2/2005 | He |
| 6,863,219 B1 | 3/2005 | Jacobsen et al. |
| 6,864,435 B2 | 3/2005 | Hermanns et al. |
| 6,864,570 B2 | 3/2005 | Smith |
| 6,872,645 B2 | 3/2005 | Duan et al. |
| 6,878,871 B2 | 4/2005 | Scher et al. |
| 6,881,979 B2 | 4/2005 | Starikov et al. |
| 6,887,450 B2 | 5/2005 | Chen et al. |
| 6,900,094 B2 | 5/2005 | Hammond et al. |
| 6,917,061 B2 | 7/2005 | Pan et al. |
| 6,936,181 B2 | 8/2005 | Bulthaup et al. |
| 6,949,199 B1 | 9/2005 | Gauzner et al. |
| 6,949,206 B2 | 9/2005 | Whiteford |
| 6,950,220 B2 | 9/2005 | Abramson et al. |
| 6,984,934 B2 | 1/2006 | Moller et al. |
| 6,989,285 B2 | 1/2006 | Ball |
| 7,029,951 B2 | 4/2006 | Chen et al. |
| 7,033,961 B1 | 4/2006 | Smart et al. |
| 7,067,903 B2 | 6/2006 | Tachibana et al. |
| 7,116,318 B2 | 10/2006 | Amundson et al. |
| 7,132,313 B2 | 11/2006 | O'Connor et al. |
| 7,148,512 B2 | 12/2006 | Leu et al. |
| 7,158,277 B2 | 1/2007 | Berggren et al. |
| 7,169,546 B2 | 1/2007 | Suzuki et al. |
| 7,169,669 B2 | 1/2007 | Blakers et al. |
| 7,170,164 B2 | 1/2007 | Chen et al. |
| 7,186,624 B2 | 3/2007 | Welser et al. |
| 7,190,051 B2 | 3/2007 | Mech et al. |
| 7,195,733 B2 | 3/2007 | Rogers et al. |
| 7,198,190 B2 | 4/2007 | Juhan et al. |
| 7,223,609 B2 | 5/2007 | Anvar et al. |
| 7,253,442 B2 | 8/2007 | Huang et al. |
| 7,255,919 B2 | 8/2007 | Sakata et al. |
| 7,291,540 B2 | 11/2007 | Mech et al. |
| 7,374,968 B2 | 5/2008 | Kornlivich et al. |
| 7,425,523 B2 | 9/2008 | Ikemizu et al. |
| 7,521,292 B2 | 4/2009 | Rogers et al. |
| 7,557,367 B2 | 7/2009 | Rogers et al. |
| 7,622,367 B1 | 11/2009 | Nuzzo et al. |
| 7,629,691 B2 | 12/2009 | Roush et al. |
| 7,635,755 B2 | 12/2009 | Kaplan et al. |
| 7,674,882 B2 | 3/2010 | Kaplan et al. |
| 7,700,402 B2 | 4/2010 | Wild et al. |
| 7,704,684 B2 | 4/2010 | Rogers et al. |
| 7,705,280 B2 | 4/2010 | Nuzzo et al. |
| 7,709,961 B2 | 5/2010 | Greenberg et al. |
| 7,727,575 B2 | 6/2010 | Kaplan et al. |
| 7,799,699 B2 | 9/2010 | Nuzzo et al. |
| 7,842,780 B2 | 11/2010 | Kaplan et al. |
| 7,896,807 B2 | 3/2011 | Clancy et al. |
| 7,932,123 B2 | 4/2011 | Rogers et al. |
| 7,943,491 B2 | 5/2011 | Nuzzo et al. |
| 7,972,875 B2 | 7/2011 | Rogers et al. |
| 7,982,296 B2 | 7/2011 | Nuzzo et al. |
| 8,039,847 B2 | 10/2011 | Nuzzo et al. |
| 8,074,890 B2 | 12/2011 | Duggan et al. |
| 8,198,621 B2 | 6/2012 | Rogers et al. |
| 8,212,218 B2 | 7/2012 | Cabral, Jr. et al. |
| 8,217,381 B2 | 7/2012 | Rogers et al. |
| 8,367,035 B2 | 2/2013 | Rogers et al. |
| 8,394,706 B2 | 3/2013 | Nuzzo et al. |
| 8,440,546 B2 | 5/2013 | Rogers et al. |
| 8,470,701 B2 | 6/2013 | Rogers et al. |
| 8,519,345 B2 | 8/2013 | Arsalan et al. |
| 8,552,299 B2 | 10/2013 | Rogers et al. |
| 8,562,095 B2 | 10/2013 | Alleyne et al. |
| 8,664,699 B2 | 3/2014 | Nuzzo et al. |
| 8,905,772 B2 | 12/2014 | Rogers et al. |
| 8,934,965 B2 | 1/2015 | Rogers et al. |
| 8,946,683 B2 | 2/2015 | Rogers et al. |
| 9,105,555 B2 | 8/2015 | Rogers et al. |
| 9,117,940 B2 | 8/2015 | Rogers et al. |
| 9,262,759 B2 | 2/2016 | Hanson et al. |
| 9,324,733 B2 | 4/2016 | Rogers et al. |
| 9,450,043 B2 | 9/2016 | Nuzzo et al. |
| 9,496,229 B2 | 11/2016 | Rogers et al. |
| 9,515,025 B2 | 12/2016 | Rogers et al. |
| 9,554,484 B2 | 1/2017 | Rogers et al. |
| 9,601,671 B2 | 3/2017 | Rogers et al. |
| 9,613,911 B2 | 4/2017 | Rogers et al. |
| 9,647,171 B2 | 5/2017 | Rogers et al. |
| 9,761,444 B2 | 9/2017 | Nuzzo et al. |
| 9,768,086 B2 | 9/2017 | Nuzzo et al. |
| 9,825,229 B2 | 11/2017 | Rogers et al. |
| 9,875,974 B2 | 1/2018 | Rogers et al. |
| 9,986,924 B2 | 6/2018 | Rogers et al. |
| 10,029,451 B2 | 7/2018 | Rogers et al. |
| 10,052,066 B2 | 8/2018 | Rogers et al. |
| 10,064,269 B2 | 8/2018 | Rogers et al. |
| 10,143,086 B2 | 11/2018 | Rogers et al. |
| 10,154,592 B2 | 12/2018 | Rogers et al. |
| 10,192,830 B2 | 1/2019 | Rogers et al. |
| 10,204,864 B2 | 2/2019 | Rogers et al. |
| 10,333,069 B2 | 6/2019 | Rogers et al. |
| 10,355,113 B2 | 7/2019 | Rogers et al. |
| 10,374,072 B2 | 8/2019 | Nuzzo et al. |
| 10,497,633 B2 | 12/2019 | Rogers et al. |
| 10,617,300 B2 | 4/2020 | Rogers et al. |
| 10,667,647 B2 | 6/2020 | Budd |
| 2001/0003043 A1 | 6/2001 | Metspalu et al. |
| 2001/0025917 A1* | 10/2001 | Asada ............... G01L 1/248 250/221 |
| 2002/0004251 A1 | 1/2002 | Roberts et al. |
| 2002/0021445 A1 | 2/2002 | Boxhevolnyi et al. |
| 2002/0087436 A1 | 7/2002 | Guthrie et al. |
| 2002/0110766 A1 | 8/2002 | Tsai et al. |
| 2003/0006527 A1 | 1/2003 | Rabolt et al. |
| 2003/0032892 A1 | 2/2003 | Erlach et al. |
| 2003/0082889 A1 | 5/2003 | Maruyama et al. |
| 2003/0087476 A1 | 5/2003 | Oohata et al. |
| 2003/0138704 A1 | 7/2003 | Mei et al. |
| 2003/0149456 A1 | 8/2003 | Rottenberg et al. |
| 2003/0178316 A1 | 9/2003 | Jacobs et al. |
| 2003/0222282 A1 | 12/2003 | Fjelstad et al. |
| 2003/0227116 A1 | 12/2003 | Halik et al. |
| 2004/0005723 A1 | 1/2004 | Empedocles et al. |
| 2004/0026684 A1 | 2/2004 | Empedocles et al. |
| 2004/0079464 A1 | 4/2004 | Kumakura |
| 2004/0081384 A1 | 4/2004 | Datesman et al. |
| 2004/0095658 A1 | 5/2004 | Buretea et al. |
| 2004/0112964 A1 | 6/2004 | Empedocles et al. |
| 2004/0136866 A1 | 7/2004 | Pontis et al. |
| 2004/0146560 A1 | 7/2004 | Whiteford et al. |
| 2004/0155290 A1 | 8/2004 | Mech et al. |
| 2004/0178390 A1 | 9/2004 | Whiteford |
| 2004/0178913 A1 | 9/2004 | Penuela et al. |
| 2004/0192082 A1 | 9/2004 | Wagner et al. |
| 2004/0114459 A1 | 10/2004 | Suenaga et al. |
| 2004/0200734 A1 | 10/2004 | Co et al. |
| 2004/0206448 A1 | 10/2004 | Dubrow |
| 2004/0211458 A1 | 10/2004 | Gui et al. |
| 2004/0242976 A1* | 12/2004 | Abreu ............... A61B 5/0008 600/315 |
| 2004/0250950 A1 | 12/2004 | Dubrow |
| 2004/0252559 A1 | 12/2004 | Gupta |
| 2005/0020094 A1 | 1/2005 | Forbes et al. |
| 2005/0233546 A1 | 1/2005 | Oohata et al. |
| 2005/0038498 A1 | 2/2005 | Dubrow et al. |
| 2005/0082526 A1 | 4/2005 | Bedell et al. |
| 2005/0096513 A1 | 5/2005 | Ozguz et al. |
| 2005/0124712 A1 | 6/2005 | Anderson et al. |
| 2005/0133954 A1 | 6/2005 | Homola |
| 2005/0212007 A1 | 9/2005 | Daniels et al. |
| 2005/0214962 A1 | 9/2005 | Daniels et al. |
| 2005/0227389 A1 | 10/2005 | Bhattacharya et al. |

(56) References Cited

U.S. PATENT DOCUMENTS

| | | |
|---|---|---|
| 2005/0238967 A1 | 10/2005 | Rogers et al. |
| 2005/0255686 A1 | 11/2005 | Yamano et al. |
| 2005/0260706 A1 | 11/2005 | Kaplan et al. |
| 2005/0261561 A1 | 11/2005 | Jones et al. |
| 2006/0038182 A1 | 2/2006 | Rogers et al. |
| 2006/0049485 A1 | 3/2006 | Pan et al. |
| 2006/0084012 A1 | 4/2006 | Nuzzo et al. |
| 2006/0085976 A1 | 4/2006 | Eldridge et al. |
| 2006/0102525 A1 | 5/2006 | Volkel et al. |
| 2006/0119853 A1 | 6/2006 | Baumberg et al. |
| 2006/0127817 A1 | 6/2006 | Ramanujan et al. |
| 2006/0129056 A1 | 6/2006 | Leuthardt et al. |
| 2006/0132025 A1 | 6/2006 | Gao et al. |
| 2006/0134893 A1 | 6/2006 | Savage et al. |
| 2006/0159837 A1 | 7/2006 | Kaplan et al. |
| 2006/0164252 A1* | 7/2006 | Richmond .......... F21V 21/0824 340/606 |
| 2006/0169989 A1 | 8/2006 | Bhatacharya |
| 2006/0173364 A1 | 8/2006 | Clancy et al. |
| 2006/0177479 A1 | 8/2006 | Giachelli et al. |
| 2006/0178655 A1 | 8/2006 | Santini et al. |
| 2006/0244105 A1 | 11/2006 | Forbes et al. |
| 2006/0248478 A1* | 11/2006 | Liau .................. G06F 3/014 715/863 |
| 2006/0255341 A1 | 11/2006 | Pinnington et al. |
| 2006/0273279 A1 | 12/2006 | Kaplan et al. |
| 2006/0279191 A1 | 12/2006 | Gehegan et al. |
| 2006/0286488 A1 | 12/2006 | Rogers et al. |
| 2006/0286785 A1 | 12/2006 | Rogers et al. |
| 2007/0009968 A1 | 1/2007 | Cunningham et al. |
| 2007/0031607 A1 | 2/2007 | Dubson et al. |
| 2007/0032089 A1 | 2/2007 | Nuzzo et al. |
| 2007/0043416 A1 | 2/2007 | Callas et al. |
| 2007/0058254 A1 | 3/2007 | Kim |
| 2007/0073130 A1 | 3/2007 | Finch et al. |
| 2007/0123963 A1 | 5/2007 | Krulevitch |
| 2007/0187862 A1 | 8/2007 | Kaplan et al. |
| 2007/0212730 A1 | 9/2007 | Vepari et al. |
| 2007/0227586 A1 | 10/2007 | Zapalac |
| 2007/0233208 A1 | 10/2007 | Kurtz et al. |
| 2007/0257821 A1 | 11/2007 | Son et al. |
| 2008/0038236 A1 | 2/2008 | Gimble et al. |
| 2008/0055581 A1 | 3/2008 | Rogers et al. |
| 2008/0085272 A1 | 4/2008 | Kaplan et al. |
| 2008/0090322 A1 | 4/2008 | Mech et al. |
| 2008/0102096 A1 | 5/2008 | Molin et al. |
| 2008/0108171 A1 | 5/2008 | Rogers et al. |
| 2008/0152281 A1 | 6/2008 | Lundquist et al. |
| 2008/0000871 A1 | 7/2008 | Suh et al. |
| 2008/0157235 A1 | 7/2008 | Rogers et al. |
| 2008/0183076 A1 | 7/2008 | Witte et al. |
| 2008/0203431 A1 | 8/2008 | Garcia et al. |
| 2008/0212102 A1 | 9/2008 | Nuzzo et al. |
| 2008/0239755 A1 | 10/2008 | Parker et al. |
| 2008/0280360 A1 | 11/2008 | Kaplan et al. |
| 2008/0288037 A1 | 11/2008 | Neysmith et al. |
| 2008/0293919 A1 | 11/2008 | Kaplan et al. |
| 2009/0004737 A1 | 1/2009 | Borenstein et al. |
| 2009/0012533 A1 | 1/2009 | Barbagli et al. |
| 2009/0028910 A1 | 1/2009 | Desimone et al. |
| 2009/0040037 A1* | 2/2009 | Schraga ................ G01S 7/4017 340/459 |
| 2009/0078990 A1 | 3/2009 | Yasuda |
| 2009/0085214 A1 | 4/2009 | Wada et al. |
| 2009/0114832 A1 | 5/2009 | Lynn et al. |
| 2009/0149930 A1 | 6/2009 | Schecnk |
| 2009/0198293 A1 | 8/2009 | Cauller et al. |
| 2009/0199960 A1 | 8/2009 | Nuzzo et al. |
| 2009/0202614 A1 | 8/2009 | Kaplan et al. |
| 2009/0208555 A1 | 8/2009 | Kuttler et al. |
| 2009/0221896 A1 | 9/2009 | Rickert et al. |
| 2009/0232963 A1 | 9/2009 | Kaplan et al. |
| 2009/0234026 A1 | 9/2009 | Kaplan et al. |
| 2009/0289246 A1 | 11/2009 | Schneider et al. |
| 2009/0293664 A1 | 12/2009 | Aabloo et al. |
| 2009/0294803 A1 | 12/2009 | Nuzzo et al. |
| 2010/0002402 A1 | 1/2010 | Rogers et al. |
| 2010/0028451 A1 | 2/2010 | Kaplan et al. |
| 2010/0046902 A1 | 2/2010 | Kaplan et al. |
| 2010/0052112 A1 | 3/2010 | Rogers et al. |
| 2010/0055438 A1 | 3/2010 | Kaplan et al. |
| 2010/0059863 A1 | 3/2010 | Rogers et al. |
| 2010/0063404 A1 | 3/2010 | Kaplan et al. |
| 2010/0065784 A1 | 3/2010 | Kaplan et al. |
| 2010/0068740 A1 | 3/2010 | Kaplan et al. |
| 2010/0070068 A1 | 3/2010 | Kaplan et al. |
| 2010/0072577 A1 | 3/2010 | Nuzzo et al. |
| 2010/0096763 A1 | 4/2010 | Kaplan et al. |
| 2010/0120116 A1 | 5/2010 | Kaplan et al. |
| 2010/0121420 A1 | 5/2010 | Fiset et al. |
| 2010/0141407 A1 | 6/2010 | Heubel et al. |
| 2010/0178304 A1 | 7/2010 | Wang et al. |
| 2010/0191328 A1 | 7/2010 | Kaplan et al. |
| 2010/0196447 A1 | 8/2010 | Kaplan et al. |
| 2010/0200752 A1 | 8/2010 | Lee et al. |
| 2010/0203226 A1 | 8/2010 | Kaplan et al. |
| 2010/0238636 A1* | 9/2010 | Mascaro ............ B29C 45/14639 361/750 |
| 2010/0279112 A1 | 11/2010 | Kaplan et al. |
| 2010/0283069 A1 | 11/2010 | Rogers et al. |
| 2010/0289124 A1 | 11/2010 | Nuzzo et al. |
| 2010/0317132 A1 | 12/2010 | Rogers et al. |
| 2011/0071439 A1 | 3/2011 | Bach-y-Rita et al. |
| 2011/0129158 A1 | 6/2011 | Sato |
| 2011/0147715 A1 | 6/2011 | Rogers et al. |
| 2011/0168403 A1 | 7/2011 | Patel |
| 2011/0170225 A1 | 7/2011 | Rogers et al. |
| 2011/0171813 A1 | 7/2011 | Rogers et al. |
| 2011/0187798 A1 | 8/2011 | Rogers et al. |
| 2011/0220890 A1 | 9/2011 | Nuzzo et al. |
| 2011/0230747 A1 | 9/2011 | Rogers et al. |
| 2011/0254665 A1 | 10/2011 | Lindsay et al. |
| 2011/0266561 A1 | 11/2011 | Rogers et al. |
| 2011/0276112 A1 | 11/2011 | Simon et al. |
| 2011/0277813 A1 | 11/2011 | Rogers et al. |
| 2011/0316120 A1 | 12/2011 | Rogers et al. |
| 2012/0157804 A1 | 6/2012 | Rogers et al. |
| 2012/0165759 A1 | 6/2012 | Rogers et al. |
| 2012/0261551 A1 | 10/2012 | Rogers et al. |
| 2012/0320581 A1 | 12/2012 | Rogers et al. |
| 2012/0327608 A1 | 12/2012 | Rogers et al. |
| 2013/0018742 A1 | 1/2013 | Fisher |
| 2013/0036928 A1 | 2/2013 | Rogers et al. |
| 2013/0041235 A1 | 2/2013 | Rogers et al. |
| 2013/0070805 A1* | 3/2013 | Coln .................. G01K 7/186 374/1 |
| 2013/0072775 A1 | 3/2013 | Rogers et al. |
| 2013/0100618 A1 | 4/2013 | Rogers et al. |
| 2013/0140649 A1 | 6/2013 | Rogers et al. |
| 2013/0200268 A1* | 8/2013 | Rafferty .................. H04Q 9/00 250/372 |
| 2014/0034815 A1 | 2/2014 | Lai et al. |
| 2014/0263989 A1* | 9/2014 | Valentino .................. G01T 1/02 250/239 |
| 2014/0264047 A1* | 9/2014 | Valentino .................. G01T 1/02 250/370.01 |
| 2014/0268601 A1* | 9/2014 | Valentino ................ G01T 1/026 361/752 |
| 2014/0326791 A1 | 11/2014 | Ishida et al. |
| 2015/0022814 A1* | 1/2015 | Kousalik ................ D01H 13/26 356/431 |
| 2015/0080695 A1 | 3/2015 | Rogers et al. |
| 2015/0085893 A1* | 3/2015 | Zhang .................... G02B 27/62 372/100 |
| 2015/0094914 A1* | 4/2015 | Abreu ................ B60H 1/00742 701/41 |
| 2015/0102208 A1 | 4/2015 | Appelboom et al. |
| 2015/0112169 A1* | 4/2015 | Lamego ................ A61B 5/6843 600/316 |
| 2015/0141767 A1 | 5/2015 | Rogers et al. |
| 2015/0237711 A1 | 8/2015 | Rogers et al. |
| 2015/0335254 A1* | 11/2015 | Fastert ................ A61B 5/6833 600/549 |

(56) References Cited

U.S. PATENT DOCUMENTS

| | | | |
|---|---|---|---|
| 2015/0373831 A1 | 12/2015 | Rogers et al. | |
| 2016/0050750 A1 | 2/2016 | Rogers et al. | |
| 2016/0064814 A1* | 3/2016 | Jang | H01Q 1/526 |
| | | | 343/842 |
| 2016/0136877 A1 | 5/2016 | Rogers et al. | |
| 2017/0020402 A1 | 1/2017 | Rogers et al. | |
| 2017/0128015 A1 | 5/2017 | Rogers et al. | |
| 2017/0133751 A1* | 5/2017 | Noh | G06K 7/10336 |
| 2017/0179085 A1 | 6/2017 | Rogers et al. | |
| 2017/0179100 A1 | 6/2017 | Rogers et al. | |
| 2017/0179356 A1 | 6/2017 | Rogers et al. | |
| 2017/0200707 A1 | 7/2017 | Rogers et al. | |
| 2017/0224257 A1 | 8/2017 | Rogers | |
| 2017/0231571 A1 | 8/2017 | Rogers et al. | |
| 2017/0347891 A1 | 12/2017 | Rogers et al. | |
| 2018/0014734 A1 | 1/2018 | Rogers et al. | |
| 2018/0064377 A1 | 3/2018 | Rogers et al. | |
| 2018/0165566 A1 | 6/2018 | Rogers et al. | |
| 2018/0175158 A1 | 6/2018 | Rogers et al. | |
| 2018/0192952 A1 | 7/2018 | Rogers et al. | |
| 2018/0274973 A1 | 9/2018 | Rogers et al. | |
| 2018/0286820 A1 | 10/2018 | Rogers et al. | |
| 2018/0303418 A1 | 10/2018 | Rogers et al. | |
| 2018/0359850 A1 | 12/2018 | Rogers et al. | |
| 2019/0053712 A1 | 2/2019 | Rogers et al. | |
| 2019/0090801 A1 | 3/2019 | Rogers et al. | |
| 2019/0369728 A1 | 12/2019 | Rogers et al. | |
| 2020/0006540 A1 | 1/2020 | Nuzzo et al. | |
| 2020/0013720 A1 | 1/2020 | Rogers et al. | |
| 2020/0022601 A1 | 1/2020 | Rogers et al. | |
| 2020/0088739 A1 | 3/2020 | Rogers et al. | |
| 2020/0093416 A1 | 3/2020 | Rogers et al. | |
| 2020/0129077 A1 | 4/2020 | Rogers et al. | |
| 2020/0155047 A1 | 5/2020 | Rogers et al. | |
| 2020/0161291 A1 | 5/2020 | Rogers et al. | |
| 2020/0315488 A1 | 10/2020 | Rogers et al. | |
| 2020/0326231 A1 | 10/2020 | Rogers et al. | |
| 2020/0345279 A1 | 11/2020 | Rogers et al. | |

FOREIGN PATENT DOCUMENTS

| | | |
|---|---|---|
| WO | WO 99/045860 | 9/1999 |
| WO | WO 00/046854 | 8/2000 |
| WO | WO 00/049421 | 8/2000 |
| WO | WO 00/049658 | 8/2000 |
| WO | WO 00/055915 | 9/2000 |
| WO | WO 00/055916 | 9/2000 |
| WO | WO 01/031082 | 5/2001 |
| WO | WO 01/033621 | 5/2001 |
| WO | WO 01/066833 | 9/2001 |
| WO | WO 01/098838 | 12/2001 |
| WO | WO 02/027701 | 4/2002 |
| WO | WO 02/043032 | 5/2002 |
| WO | WO 02/073699 | 9/2002 |
| WO | WO 02/092778 | 11/2002 |
| WO | WO 02/097724 | 12/2002 |
| WO | WO 2004/099068 | 12/2002 |
| WO | WO 03/030194 | 4/2003 |
| WO | WO 03/032240 | 4/2003 |
| WO | WO 03/049201 | 6/2003 |
| WO | WO 03/063211 | 7/2003 |
| WO | WO 03/085700 | 10/2003 |
| WO | WO 03/085701 | 10/2003 |
| WO | WO 03/092073 | 11/2003 |
| WO | WO 04/000915 | 12/2003 |
| WO | WO 04/001103 | 12/2003 |
| WO | WO 04/003535 | 1/2004 |
| WO | WO 04/022637 | 3/2004 |
| WO | WO 04/022714 | 3/2004 |
| WO | WO 04/023527 | 3/2004 |
| WO | WO 04/024407 | 3/2004 |
| WO | WO 04/027822 | 4/2004 |
| WO | WO 2004/032190 | 4/2004 |
| WO | WO 2004/032191 | 4/2004 |
| WO | WO 2004/032193 | 4/2004 |
| WO | WO 2004/034025 | 4/2004 |
| WO | WO 2004/062697 | 7/2004 |
| WO | WO 2004/086289 | 10/2004 |
| WO | WO 2004/094303 | 11/2004 |
| WO | WO 2004/100252 | 11/2004 |
| WO | WO 2004/105456 | 12/2004 |
| WO | WO 2005/000483 | 1/2005 |
| WO | WO 2005/005679 | 1/2005 |
| WO | WO 2005/012606 | 2/2005 |
| WO | WO 2005/015480 | 2/2005 |
| WO | WO 2005/017962 | 2/2005 |
| WO | WO 2005/022120 | 3/2005 |
| WO | WO 2005/029578 | 3/2005 |
| WO | WO 2005/054119 | 6/2005 |
| WO | WO 2005/104756 | 11/2005 |
| WO | WO 02/097708 | 12/2005 |
| WO | WO 2005/122285 | 12/2005 |
| WO | WO 2005/123114 | 12/2005 |
| WO | WO 2006/028996 | 3/2006 |
| WO | WO 2006/042287 | 4/2006 |
| WO | WO 2006/076711 | 7/2006 |
| WO | WO 2006/104069 | 10/2006 |
| WO | WO 2006/130721 | 12/2006 |
| WO | WO 2007/000037 | 1/2007 |
| WO | WO 2007/016524 | 2/2007 |
| WO | WO 2007/028003 | 3/2007 |
| WO | WO 2007/056183 | 5/2007 |
| WO | WO 2007/126412 | 11/2007 |
| WO | WO 2008/030666 | 3/2008 |
| WO | WO 2008/030960 | 3/2008 |
| WO | WO 2008/036837 | 3/2008 |
| WO | WO 2008/055054 | 5/2008 |
| WO | WO 2008/085904 | 7/2008 |
| WO | WO 2008/103464 | 8/2008 |
| WO | WO 2008/106485 | 9/2008 |
| WO | WO 2008/108838 | 9/2008 |
| WO | WO 2008/118133 | 10/2008 |
| WO | WO 2008/118211 | 10/2008 |
| WO | WO 2008/127401 | 10/2008 |
| WO | WO 2008/127402 | 10/2008 |
| WO | WO 2008/127403 | 10/2008 |
| WO | WO 2008/127404 | 10/2008 |
| WO | WO 2008/127405 | 10/2008 |
| WO | WO 2008/140562 | 11/2008 |
| WO | WO 2008/143635 | 11/2008 |
| WO | WO 2008/150861 | 12/2008 |
| WO | WO 2009/011709 | 1/2009 |
| WO | WO 2009/023615 | 2/2009 |
| WO | WO 2009/061823 | 5/2009 |
| WO | WO 2009/075625 | 6/2009 |
| WO | WO 2009/076088 | 6/2009 |
| WO | WO 2009/090398 | 7/2009 |
| WO | WO 2009/100280 | 8/2009 |
| WO | WO 2009/111641 | 9/2009 |
| WO | WO 2009/114115 | 9/2009 |
| WO | WO 2009/114689 | 9/2009 |
| WO | WO 2009/118678 | 10/2009 |
| WO | WO 2009/126689 | 10/2009 |
| WO | WO 2009/140588 | 11/2009 |
| WO | WO 2009/155397 | 12/2009 |
| WO | WO 2010/005707 | 1/2010 |
| WO | WO 2010/036807 | 4/2010 |
| WO | WO 2010/036992 | 4/2010 |
| WO | WO 2010/040528 | 4/2010 |
| WO | WO 2010/042798 | 4/2010 |
| WO | WO 2010/049881 | 5/2010 |
| WO | WO 2010/057142 | 5/2010 |
| WO | WO 2010/065957 | 6/2010 |
| WO | WO 2010/081989 | 7/2010 |
| WO | WO 2010/126640 | 11/2010 |
| WO | WO 2010/132552 | 11/2010 |
| WO | WO 2010/141133 | 12/2010 |
| WO | WO 2011/005381 | 1/2011 |
| WO | WO 2011/006133 | 1/2011 |
| WO | WO 2011/008842 | 1/2011 |
| WO | WO 2011/011347 | 1/2011 |
| WO | WO 2011/026101 | 3/2011 |
| WO | WO 2011/038401 | 3/2011 |

(56) References Cited

FOREIGN PATENT DOCUMENTS

| WO | WO 2011/041395 | 4/2011 |
|---|---|---|
| WO | WO 2011/046652 | 4/2011 |
| WO | WO 2011/084450 | 7/2011 |
| WO | WO 2011/112931 | 9/2011 |
| WO | WO 2011/115643 | 9/2011 |
| WO | WO 2012/167096 | 12/2012 |
| WO | WO 2013/010113 | 1/2013 |
| WO | WO 2013/089867 | 6/2013 |
| WO | WO 2013/149181 | 10/2013 |
| WO | WO 2014/032193 | 3/2014 |
| WO | WO 2014/169170 | 10/2014 |
| WO | WO 2014/169218 | 10/2014 |
| WO | WO 2015/051085 | 4/2015 |
| WO | WO 2017/173339 | 10/2017 |
| WO | WO 2017/218878 | 12/2017 |
| WO | WO 2018/140693 | 8/2018 |
| WO | WO 2018/140743 | 8/2018 |
| WO | WO 2018/209100 | 11/2018 |
| WO | WO 2018/223033 | 12/2018 |
| WO | WO 2018/223044 | 12/2018 |
| WO | WO 2018/223058 | 12/2018 |
| WO | WO 2018/223090 | 12/2018 |
| WO | WO 2019/161277 | 8/2019 |
| WO | WO 2019/165219 | 8/2019 |
| WO | WO 2019/191693 | 10/2019 |
| WO | WO 2019/191703 | 10/2019 |
| WO | WO 2019/222605 | 11/2019 |
| WO | WO 2020/092747 | 5/2020 |
| WO | WO 2020/092764 | 5/2020 |
| WO | WO 2020/092786 | 5/2020 |

OTHER PUBLICATIONS

European Supplemental Search Report, dated Oct. 31, 2018, corresponding to European Application No. 16804359.4, a related application, 9 pp.
Search Report and Written Opinion, dated Oct. 24, 2016, corresponding to International Application No. PCT/US2016/035331 (filed Jun. 1, 2016), parent of the present application, 13 pp.
European Supplemental Search Report, dated Jan. 31, 2019, corresponding to European Application No. 16804361.0, a related application, 8 pp.
Search Report and Written Opinion, dated Oct. 11, 2016, corresponding to International Application No. PCT/US16/35336 (filed Jun. 1, 2016), parent of the present application, 12 pp.
Ahn et al. "Stretchable electronics: materials, architectures and integrations," J Phys. D: Appl. Phys., 2012, 45:103001 (14 pp.).
Bean "Nail Growth: Thirty-five Years of Observation," Arch Intern Med, 1980, 140(1):73-76.
Chinese First Office Action with English translation, dated Jul. 3, 2019, in Chinese Patent Application No. 201680045183.6, 19 pp.
Dangerous Things (2014) "The xNT implantable NFC chip," Retrieved Mar. 15, 2014, from http: //www.indiegogo.com/projects/the-xnt-implantable-nfc-chip.
European Examination Report, dated Aug. 6, 2019, in European Patent Application No. 16804359.4, 5 pp.
Fitzpatrick "The Validity and Practicality of Sun-Reactive Skin Types I Through VI," Arch. Dermatol., 1988 124(6):869-871.
Freudenthal et al. "Suitability of NFC for Medical Device Communication and Power Delivery," IEEE Dallas Engineering in Medicine and Biology Workshop, 2007:51-54.
Gao et al. "Epidermal photonic devices for quantitative imaging of temperature and thermal transport characteristics of the skin," Nature Communications, Sep. 2014, 5:4938. (10 pp.).
Harpster et al. "A passive wireless integrated humidity sensor," Sensor Actuat a-Phys, 2002, 95: 100-107.
Huang et al. "Materials and Designs for Wireless Epidermal Sensors of Hydration and Strain," Adv Funct Mater, Mar. 2014, 24: 3846-3854.

Huang et al. "Stretchable, Wireless Sensors and Functional Substrates for Epidermal Characterization of Sweat," Small, Apr. 2014, 10(15):3083-3090.
Jang et al. "Soft network composite materials with deterministic and bio-inspired designs," Nature Commun, Mar. 2015, 6:6566. (11 pp.).
Jeong et al. "Materials and Optimized Designs for Human-Machine Interfaces Via Epidermal Electronics," Adv Mater, 2013, 25(47):6839. (21 pp.).
Kim et al. "Epidermal Electronics," Science, 2011, 333:838-843. (Additional supporting material 39 pp.).
Kim et al. "Flexible and Stretchable Electronics for Biointegrated Devices," Annu. Rev. Biomed. Eng., 2012, 14:113-128.
Kim et al. "Epidermal Electronics with Advanced Capabilities in Near-Field Communication," Small, Feb. 2015, 11(8):906-912.
"LED Circuit," last edited Jan. 2020, Wikipedia, available online at https://en.wikipedia.org/wiki/LED_circuit#LED_as_light_sensor, 6 pp.
Lu et al. "Delamination of stiff islands patterned on stretchable substrates," Int J Mater Res, 2007, 98(8):717-722.
Murdan "Transverse fingernail curvature in adults: a quantitative evaluation and the influence of gender, age, and hand size and dominance," Int J Cosmetic Sci, 2011, 33:509-513. (17 pp.).
Raupp "(Invited) Flexible Thin Film Transistor Arrays as an Enabling Platform Technology: Opportunities and Challenges," Ecs Transactions 2011, 37(1):229-240.
Rose et al. "Adhesive RFID Sensor Patch for Monitoring of Sweat Electrolytes," IEEE Transactions on Biomedical Engineering, Jun. 2015, 62(6): 1457-1465.
Saeed et al. "Off-line NFC Tag Authentication," The 7th International Conference for Internet Technology and Secured Transactions, 2012, 730-735.
Sidén et al. "Home care with NFC sensors and a smart phone", Proceedings of the 4th International Symposium on Applied Sciences in Biomedical and Communication Technologies, 2011.
USPTO "Non-Final Office Action," dated Oct. 12, 2018, in U.S. Appl. No. 15/578,602, 8 pp.
USPTO "Final Office Action," dated Jun. 6, 2019, in U.S. Appl. No. 15/578,602, 8 pp.
USPTO "Non-Final Office Action," dated Sep. 17, 2019, in U.S. Appl. No. 15/578,602, 7 pp.
Wang et al. "Mechanics of Epidermal Electronics," J Appl Mech-T Asme, 2012, 79: 031022-1-031022-6.
Windmiller et al. "Electrochemical Sensing Based on Printable Temporary Transfer Tattoos," Chem Commun, 2012, 48(54):6794-6796.
Windmiller et al. "Wearable Electrochemical Sensors and Biosensors: A Review," Electroanalysis, 2013, 25(1): 29-46.
Xu et al. "Soft Microfluidic Assemblies of Sensors, Circuits, and Radios for the Skin," Science, Apr. 2014, 344(6179):70-74.
Zeng et al. "Fiber-Based Wearable Electronics: A Review of Materials, Fabrication, Devices, and Applications," Adv. Mater., Jun. 2014, 26:5310-5336.
Žnidaršič et al. "Adoption of RFID microchip for eHealth according to eActivities of potential users," BLED 2014 Proceedings, Jun. 2014, 16: 1-14.
AZoSensors (2013) "LED Light Sensors," AZoNetwork; Available online at https://www.azosensors.com/article.aspx?ArticleID=329, Accessed Apr. 10, 2020: 3 pp.
Chinese Second Office Action with English translation, dated Apr. 22, 2020, in Chinese Patent Application No. 201680045183.6, 19 pp.
Marian (2012) "LED as Light Detector," Electro Schematics; Available online at https://www.electroschematics.com/led-as-light-detector/, Accessed Apr. 10, 2020: 7 pp.
Mims III (Jan. 2014) "How to Use LEDs to Detect Light," MAKE; Available online at https://makezine.com/projects/make-36-boards/how-to-use-leds-to-detect-light/, Accessed Apr. 10, 2020: 9 pp.
Australian Exam Report, dated Sep. 4, 2020, corresponding to Australian Patent Application No. 2016270805, 4 pp.
Australian Exam Report, dated Sep. 21, 2020, corresponding to Australian Patent Application No. 2016270807, 3 pp.

(56) References Cited

OTHER PUBLICATIONS

Brazilian Office Action, dated May 20, 2020, corresponding to Brazilian Patent Application No. 112017025616-9, 5 pp.
European Office Action, dated Apr. 24, 2020, corresponding to European Patent Application No. 16804361.0, 5 pp.
European Office Action, dated May 14, 2020, corresponding to European Patent Application No. 16804359.4, 5 pp.
USPTO "Notice of Allowance," dated Jan. 29, 2020, in U.S. Appl. No. 15/578,602, 8 pp.
USPTO "Non-Final Office Action," dated Sep. 2, 2020, in U.S. Appl. No. 16/861,608, 9 pp.

* cited by examiner

--Prior Art--

Influence of UV-A/B in Sunlight

UV-A

- The wavelength is 320~400nm.
- The percentage for UV in sunlight is 99%
- Cause of suntan, wrinkles, skin aging and skin cancer.

UV-B

- The wavelength is 280~320nm.
- The percentage for UV in sunlight is 1%.
- More harmful than UV-A
- Cause of sunburn and skin cancer — Prior Art —

NFC Chip Details

- AMS SL13A

Parameters:
1) Single channel A/D: 300-600 mV **
2) Built-in temp sensing capability --Prior Art--

NFC Chip Details

- TI RF430FRL152H

Parameters:
1) Three A/D ports: 0-1.5 V **
2) Built-in temp sensing capability
3) On-board processing capability

Key Components:
(1): LED: 395 nm, 0603 package
W L H: 1.6, 0.8, 0.6 mm
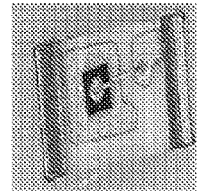
(2): Cap: 14mF
W L H: 3.2, 2.5, 1 mm
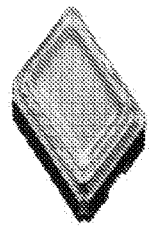
(3): NFC: AMS Die
2.37, 2.24, 0.120 mm
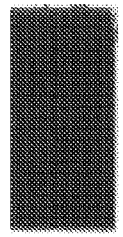
Other: Coil substrate (WISP/Echinacea), filter (plastic)
FIG. 11

Key Components:
(1):     LED: 395 nm, 0603 package
W L H: 1.6, 0.8, 0.6 mm
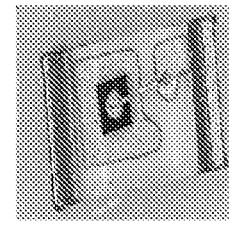
(2):     Cap: 14mF
W L H: 3.2, 2.5, 0.9 mm
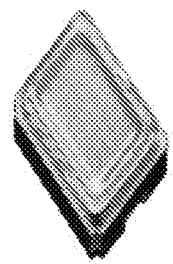
(3):     NFC: TI
W L H: 2, 2, 0.110 mm
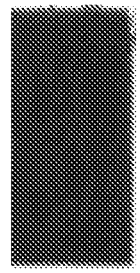
Other: Coil substrate, filter (plastic)
FIG. 12

Ultraminiaturized, UV Dosimeter

Typical cap voltage vs UV exposure time and leakage SPICE simulation
$$C\frac{dV(t)}{dt} = i(t) - \frac{V(t)}{R_{leak}}$$
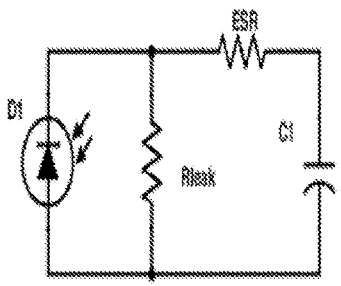
We can accurately determine the leakage resistance by simulation for a variety of photodiodes
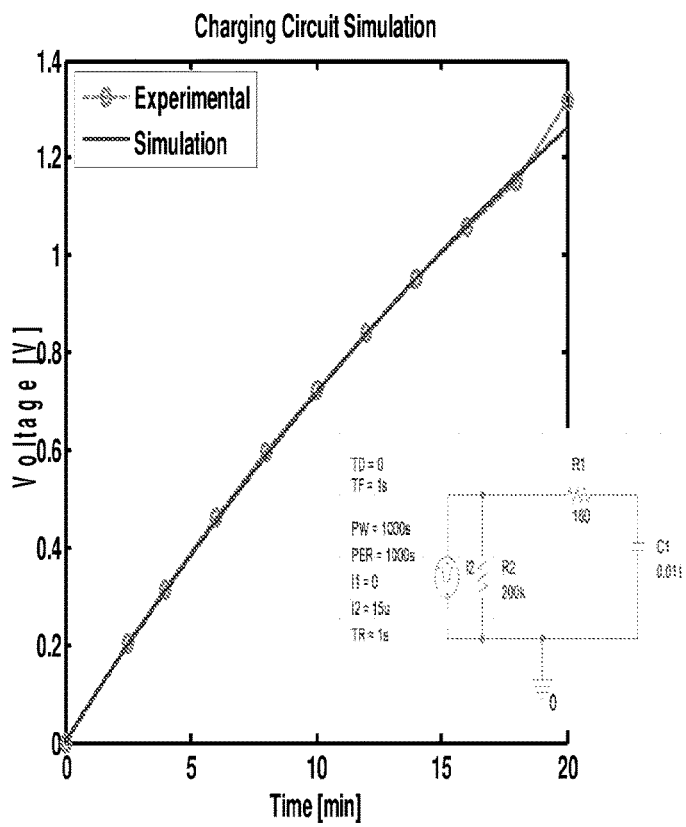
FIG. 19

Minimum Erythema Dose MED-Solar Simulator

Solar Simulator
- UVB = 0.3 J/M2
- UVA = 41 J/M2

Minimal Erythema Dose (MED)

Fitzpatrick, T. B. (1988) *Arch. Dermatol.* 124(6)

| Skin Type | Skin Color | MED-A(J/m$^2$) | MED-B(J/m$^2$) |
|---|---|---|---|
| I | Caucasian ~ Fair skin, Blue eye~ | 200000 | 200 |
| II | Caucasian ~ Fair skin, Green eye~ | 300000 | 250 |
| III | Dark Caucasian, light Asian | 400000 | 300 |
| IV | Hispanic, Asian, Mediterranean | 500000 | 450 |
| V | Middle Eastern, Latin, Indian | 700000 | 600 |
| VI | Dark-skinned black | 1000000 | 1000 |

FIG. 20

Assumptions for UVB used for determining MED with 1 channel AMS System

| Skin Type | MED-UVA (J/m2) | Solar Simulator Intensity (W/m2) | Seconds | Minutes | Hours |
|---|---|---|---|---|---|
| I | 200000 | 41 | 4878.0 | 81.3 | 1.4 |
| II | 300000 | 41 | 7317.1 | 122.0 | 2.0 |
| III | 400000 | 41 | 9756.1 | 162.6 | 2.7 |
| IV | 500000 | 41 | 12195.1 | 203.3 | 3.4 |
| V | 700000 | 41 | 17073.2 | 284.6 | 4.7 |
| VI | 1000000 | 41 | 24390.2 | 406.5 | 6.8 |

| Ratio to MED | | UVA+UVB Exposure Times (m) |
|---|---|---|
| UV-A | UV-B | |
| 0.12 | 0.88 | 9.8 |
| 0.10 | 0.90 | 12.5 |
| 0.09 | 0.91 | 15.1 |
| 0.11 | 0.89 | 22.3 |
| 0.10 | 0.90 | 29.8 |
| 0.12 | 0.88 | 48.9 |

| Skin Type | MED-UVb (J/m2) | Solar Simulator Intensity (W/m2) | Seconds | Minutes | Hours |
|---|---|---|---|---|---|
| I | 200 | 0.3 | 666.7 | 11.1 | 0.2 |
| II | 250 | 0.3 | 833.3 | 13.9 | 0.2 |
| III | 300 | 0.3 | 1000.0 | 16.7 | 0.3 |
| IV | 450 | 0.3 | 1500.0 | 25.0 | 0.4 |
| V | 600 | 0.3 | 2000.0 | 33.3 | 0.6 |
| VI | 1000 | 0.3 | 3333.3 | 55.6 | 0.9 |

FIG. 21

Instantaneous UV dosage/UV level Measurement
Scienterra
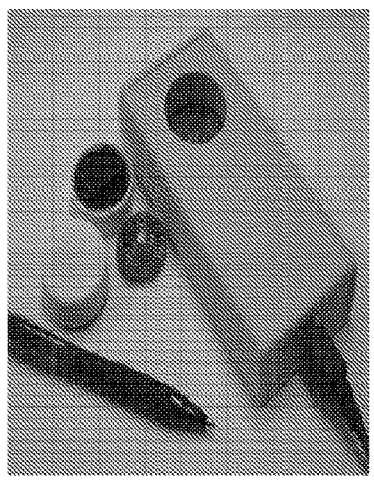
Solartech
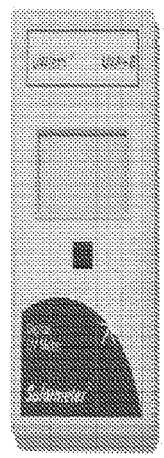
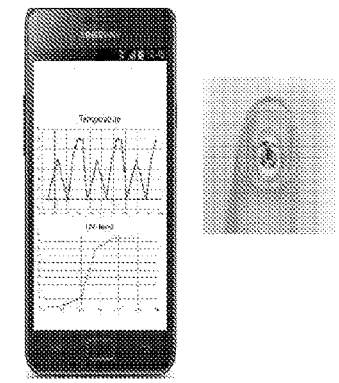
- Similar circuit as accumulated UV dosage measurement
- More sensitive UV photo diode
- Multiple ADC sampling
- Software data processing
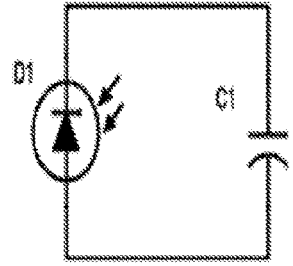
$$\frac{V1 - V2}{\Delta t} = \frac{\bar{I}}{C}$$
$$\bar{I} = E_{UV} A \gamma$$
$$E_{UV} = \frac{C(V1 - V2)}{\Delta t A \gamma}$$
FIG. 22

- UVB light source intensity 0.5W/m²
- Super Capacitor   14 mF
- Moderate charging with only one UVB sensor and large cap.
- Increased area boost sensitivity, with 7 UVB sensors stacked together (bottom)
- Equivalent time in terms of measurement condition
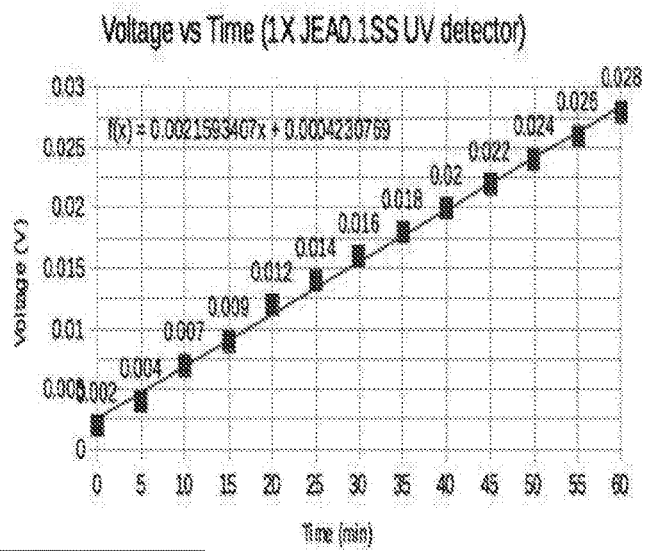
| MED | I | II | III | IV | V | VI |
|---|---|---|---|---|---|---|
| Time | 400 s | 500 s | 600 s | 900 s | 1200s | 2000s |
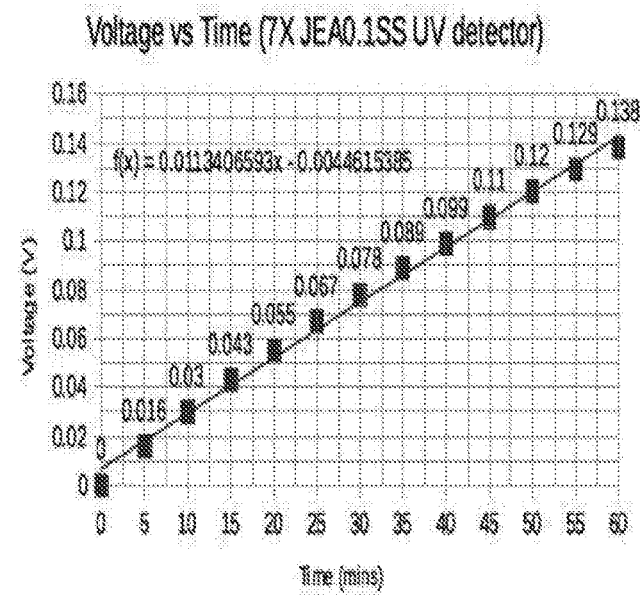
FIG. 25

Sensitivities of Capacitors 330 uF capacitor
charge rates

| Time (mins) | Voltage (V) |
|---|---|
| 0 | 0 |
| 5 | 0.32 |
| 10 | 0.65 |
| 15 | 0.893 |
| 17.45 | 1 |

| MED | I | II | III | IV | V | VI |
|---|---|---|---|---|---|---|
| Time | 6.6 m | 8.3 m | 10 m | 15 m | 20 m | 33.3 m |

UV sensing software

Software features

- ✓ Access to all three ADC channels plus internal temperature sensor is supported by the software
- ✓ ADC single reading and continuous real time plot are implemented
- ✓ Concurrent plot for three ADC channels is fully supported
- ✓ Super capacitor reset function is implemented in the software (need hardware support)
- ✓ Save ADC reading to local computer disk for future processing

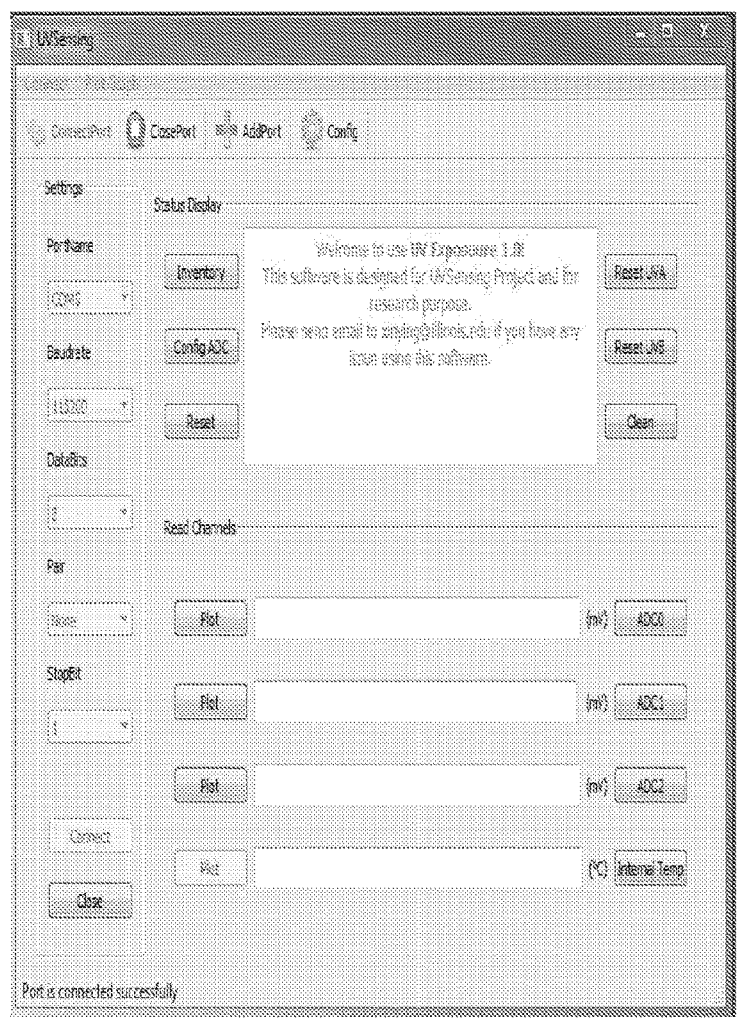

FIG. 28

TI NFC App. 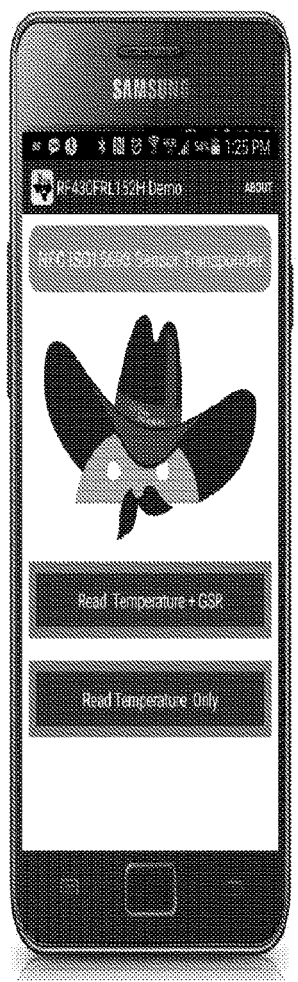 Statistics 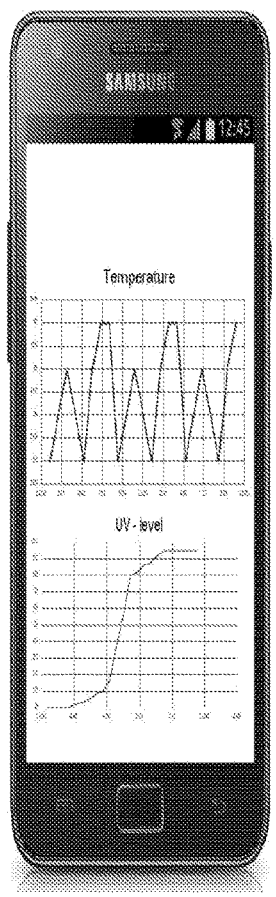 Social networks 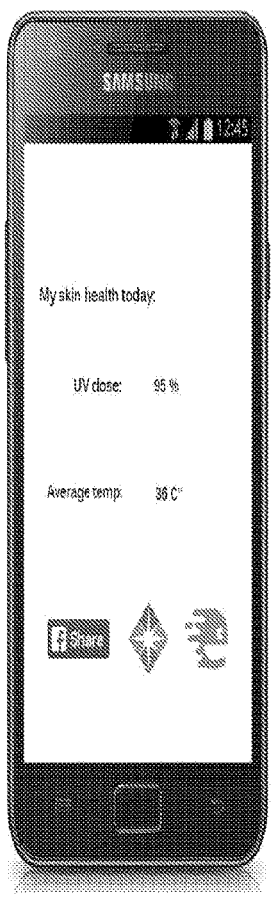
FIG. 29

UVB LED

- GUVB-S11SD
- Much smaller size (2.8mmX3.5mm)
- UV-responsivity 0.11A/W
- Active area 0.076 mr

Typical cap voltage vs UV exposure time and leakage SPICE simulation
$$C\frac{dV(t)}{dt} = i(t) - \frac{V(t)}{R_{leak}}$$
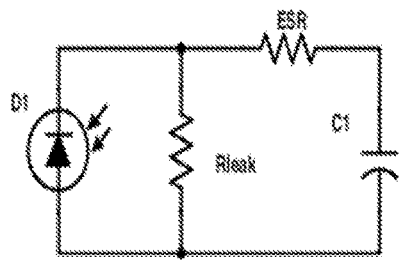
We can accurately determine the leakage resistance by simulation for a variety of photodiodes
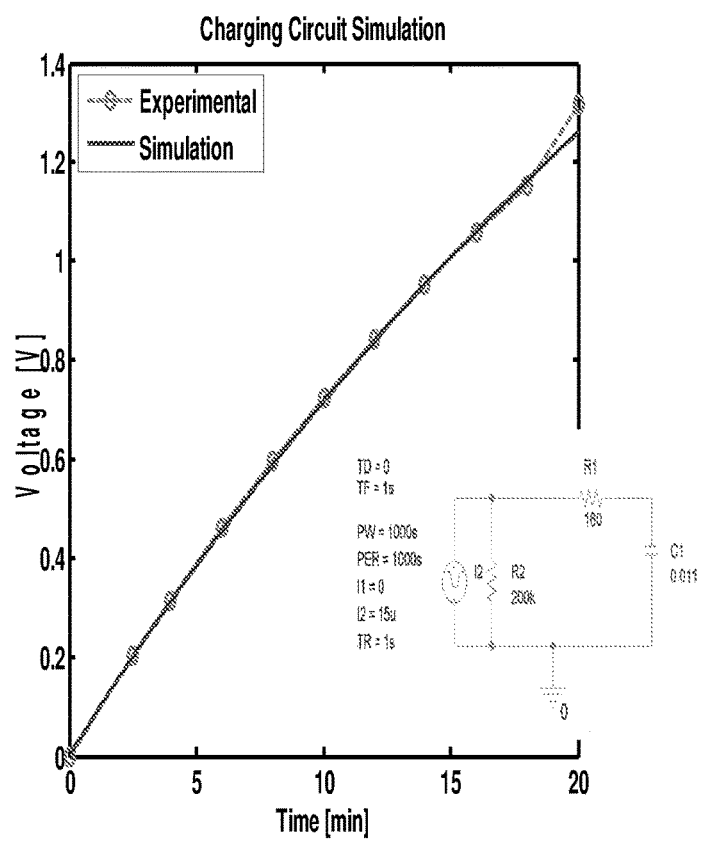
FIG. 33

Instantaneous UV dosage/UV level measurement

- Similar circuit as accumulated UV dosage measurement
- More sensitive UV photo diode
- Multiple ADC sampling
- Software data processing $$\frac{V1 - V2}{\Delta t} = \frac{\bar{I}}{C}$$

$$\bar{I} = E_{UV} A \gamma$$

$$E_{UV} = \frac{C(V1 - V2)}{\Delta t A \gamma}$$

UVB calibration measurement

UVB photo sensor
- JEA0.1SS
- Area: 0.1mm²
- UV-responsivity: 0.18A/W
- Larger die area sensor is available

| Time (min) | UV level | Voltage (mV) | w/o filter | UV dosage (J/m2) |
|---|---|---|---|---|
| 0 | 0 | 0 | 0 | 0 |
| 81.3 | MED I | 124 | 264 | 200000 |

Results
1) 12mV after 10min.
2) 7 mV after 10min.
3) 3 mV after 10min.
The patch I was using for this test was measured wirelessly using the TI reader and GUI software app 1. Keeping hand directly in the sun.
2. Walking with hand in the normal down/swinging position (not paying attention to angle etc.) keeping other side/hand facing east toward the sun. (walking south)
3. Random (in reference to the sun) walking directions (attempting to avoid shade)

FIG. 36

Skin or Nail Mounted Sensors of Exposure in UV Phototherapy

UV-B therapy, used to treat psoriasis, atopic dermatitis (eczema), vitiligo (loss of skin color) and some other skin diseases.

UV-A treatment for skin problems such as psoriasis, eczema, vitiligo UV-A light is applied most commonly to persistent problems with hands and feet.

Phototherapy in the NICU

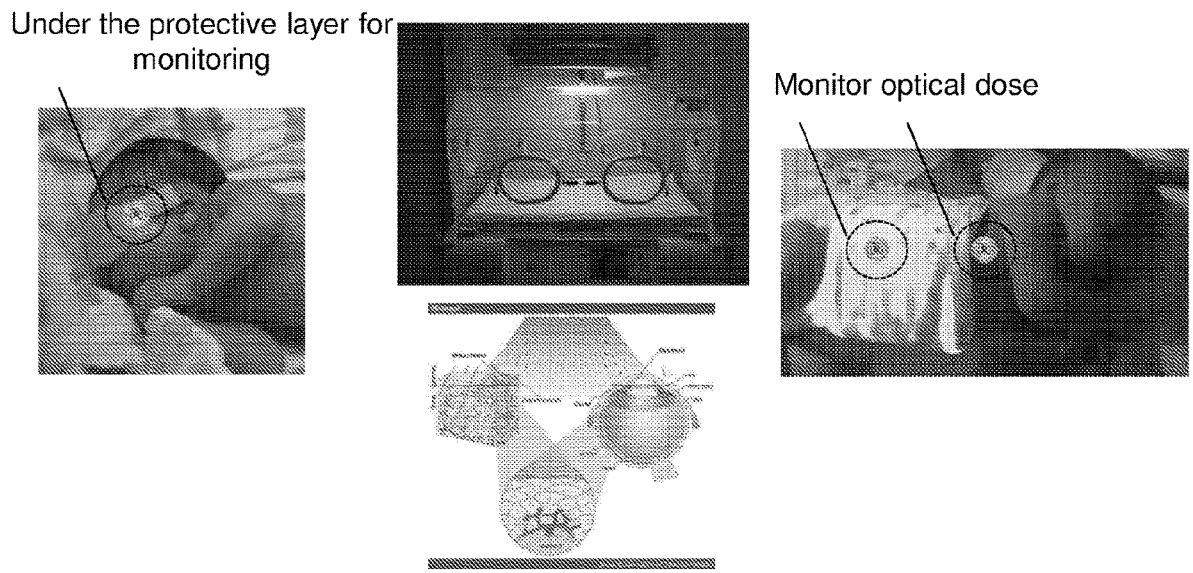

Blue-light exposure of cutaneous and uveal melanocytes during phototherapy. Ocular melanocytes consist of two different cell types: conjunctival and uveal melanocytes. Uveal melanocytes reside in the middle layer of the eyeball: in the iris, the ciliary body and the choroid. Conjunctival melanocytes are located in the conjunctiva (thin layers of epithelium and underlying connective tissue covering the anterior surface of the sclera and the posterior surface of the eyelids).

FIG. 38

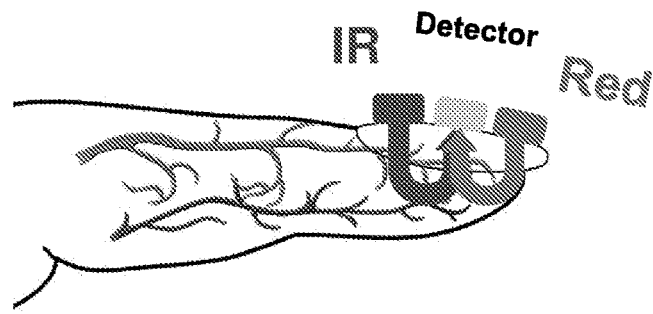
(B)
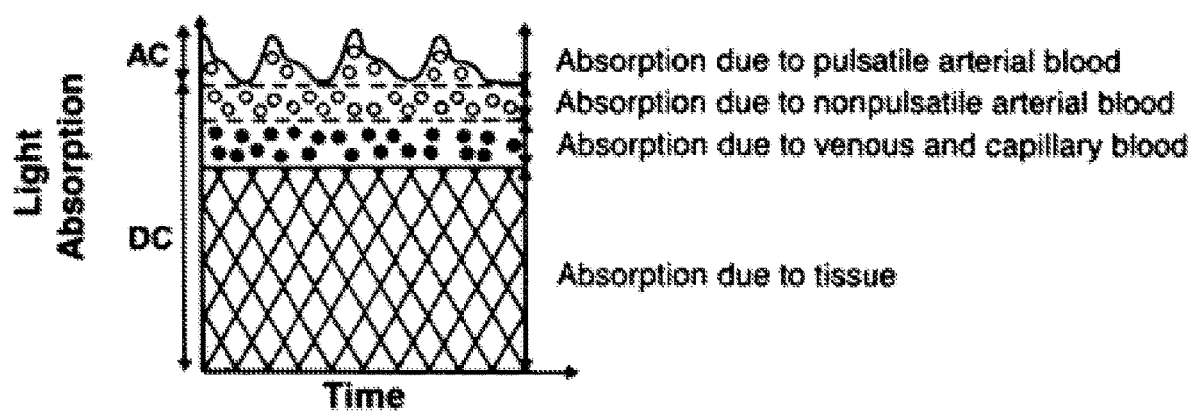
(C)
FIG. 40 (con't)

1. The NFC reader gives power to the device
2. LEDs turn on
3. A Photodetector get light signals
4. NFC converts the signal and transmits the data to the NFC reader

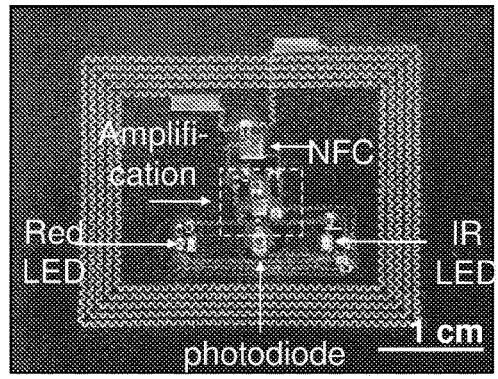
(A)
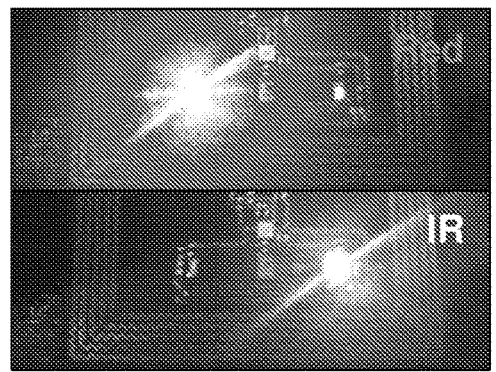
(B)
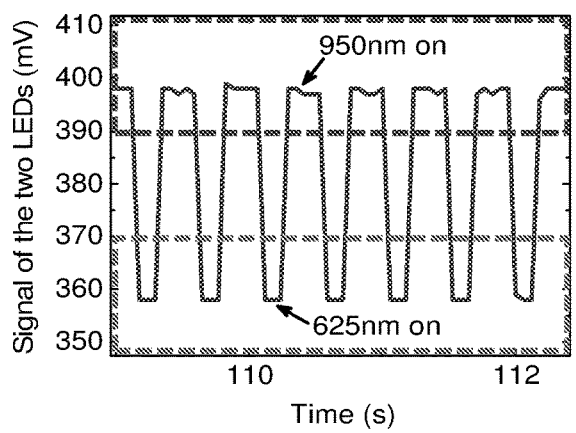
(C)
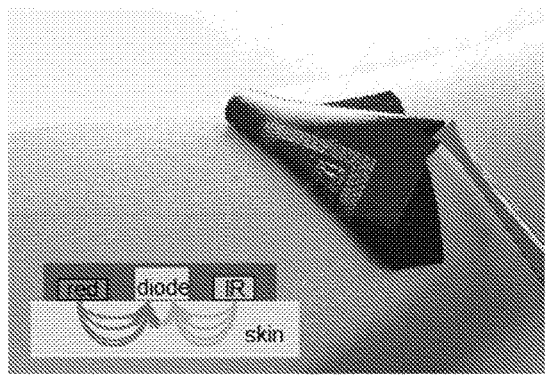
(D)
FIG. 42 simplification    miniaturization (A)

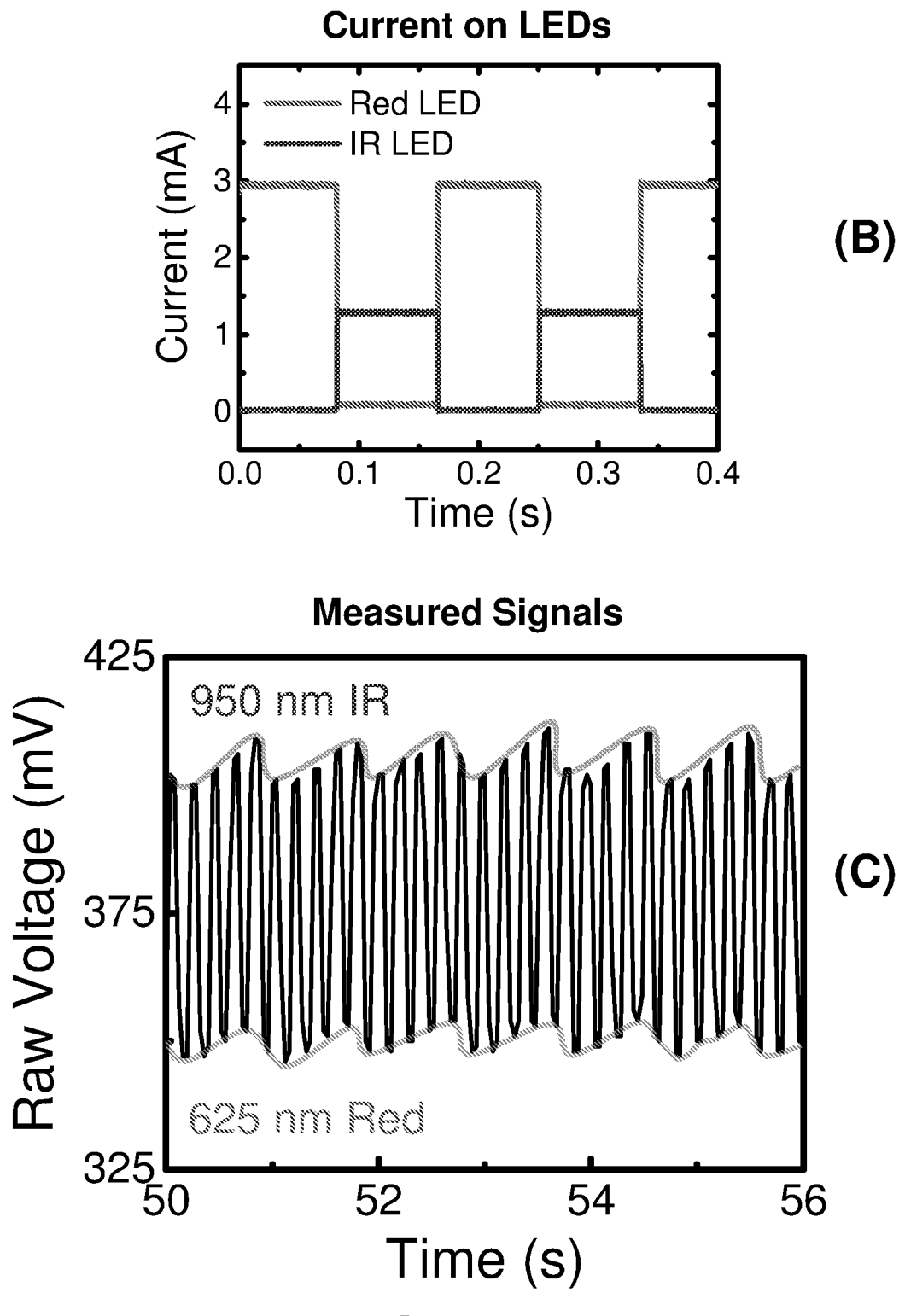
FIG. 45 (con't)

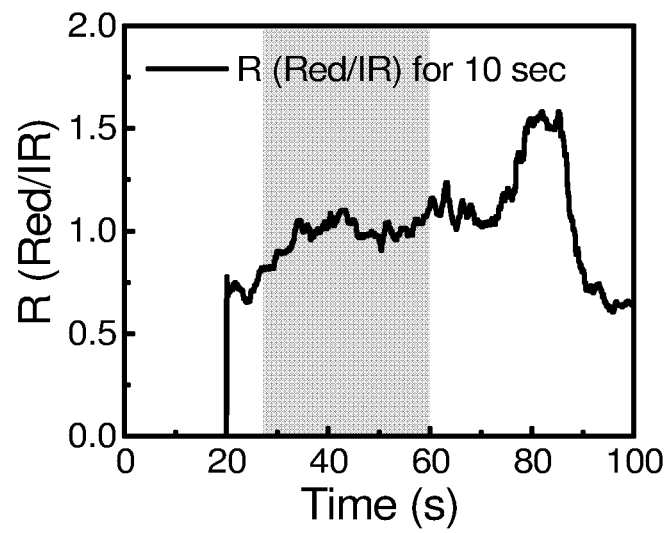
(D)
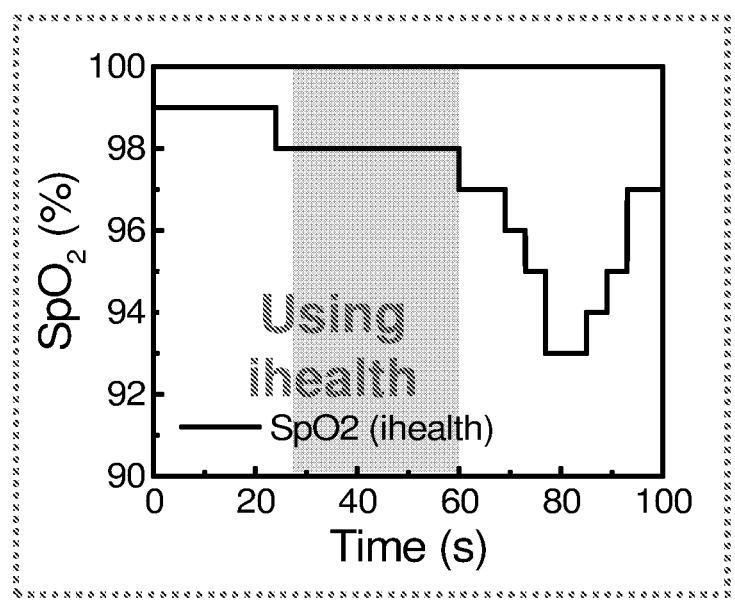
(E)
FIG. 46 (con't)

UV spectrum of Bilirubin
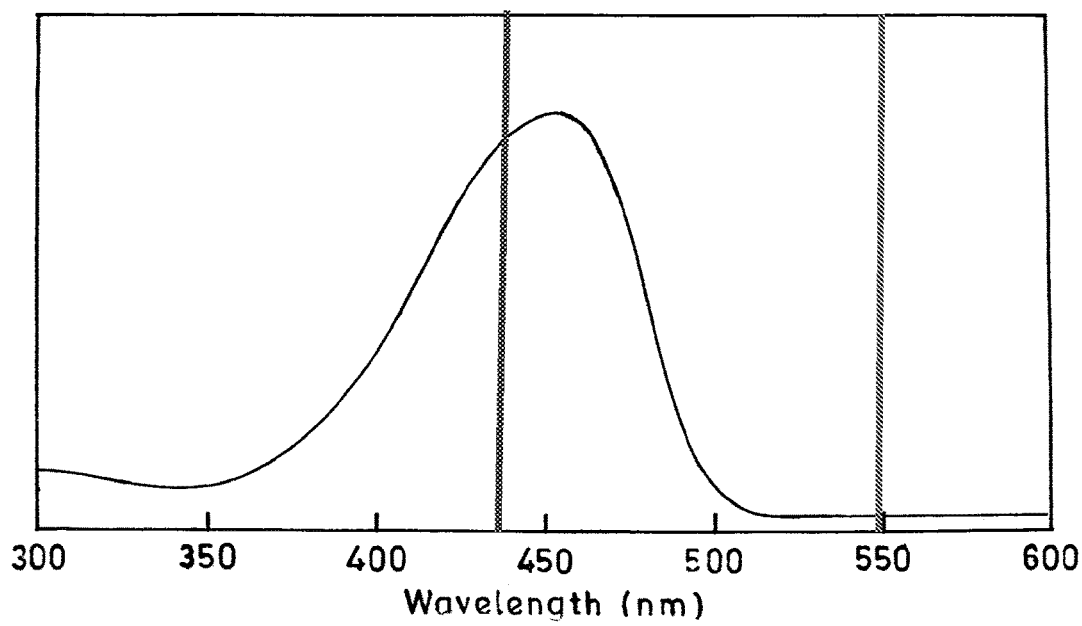
Normal skin
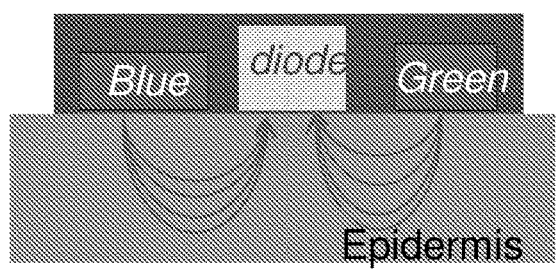
Jaundice skin
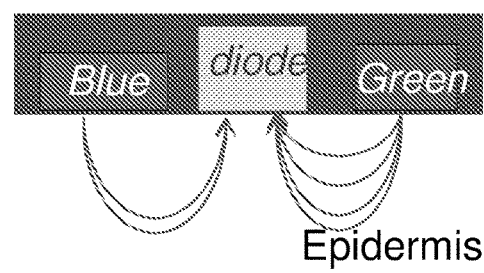
FIG. 47

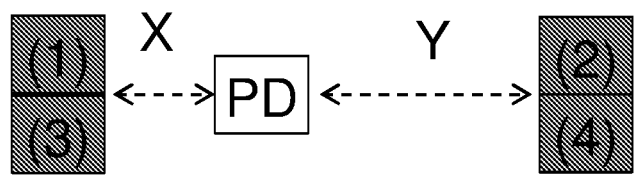
(A)
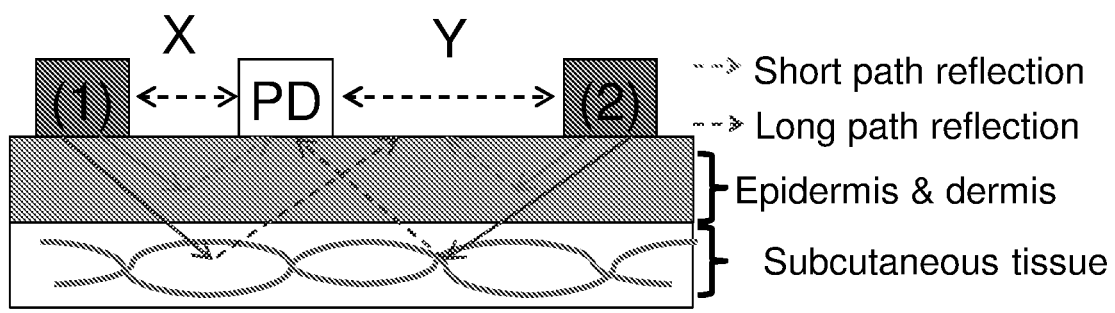
(B)
FIG. 48

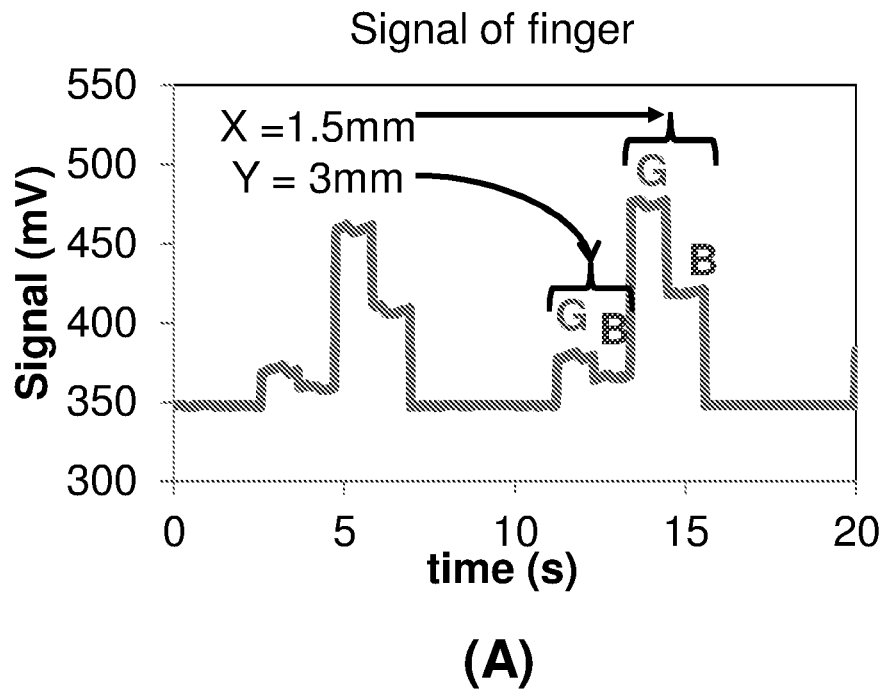
(A)
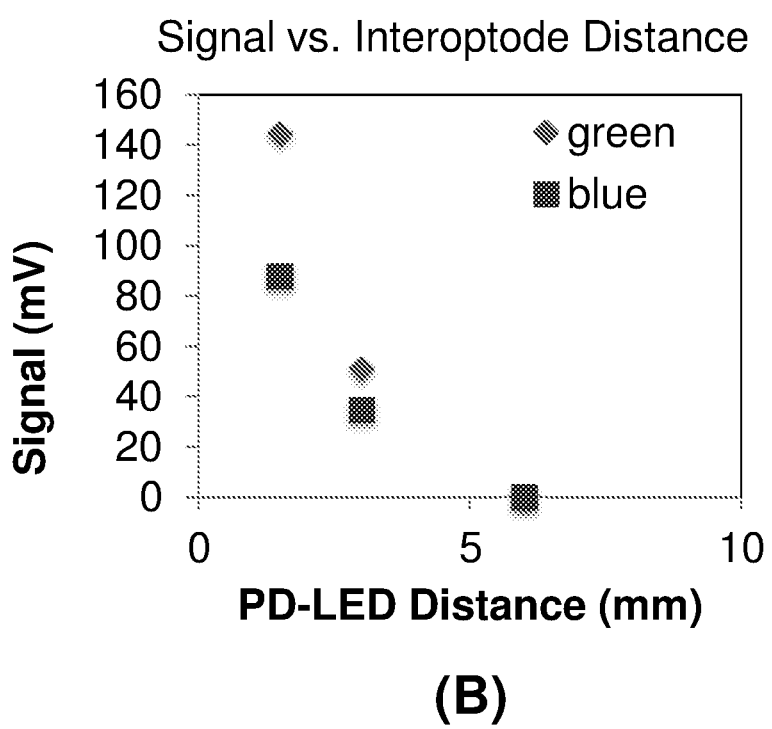
(B)
FIG. 49

Light source: 1.4 mW/cm² UV-A (peak 365 nm)
| Skin Type | MED-UVA [J/m2] | sec | min | hour |
|---|---|---|---|---|
| I | 200000 | 14286 | 238 | 3.97 |
| II | 300000 | 21429 | 357 | 5.95 |
| III | 400000 | 28571 | 476 | 7.94 |
| IV | 500000 | 35714 | 595 | 9.92 |
| V | 700000 | 50000 | 833 | 13.89 |
| VI | 1000000 | 71429 | 1190 | 19.84 |
(A)
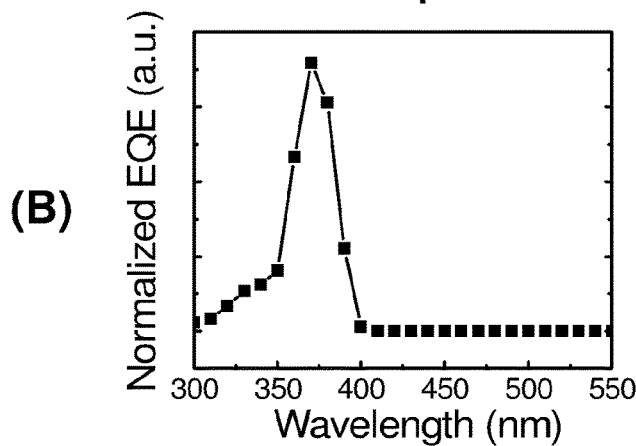
(B)
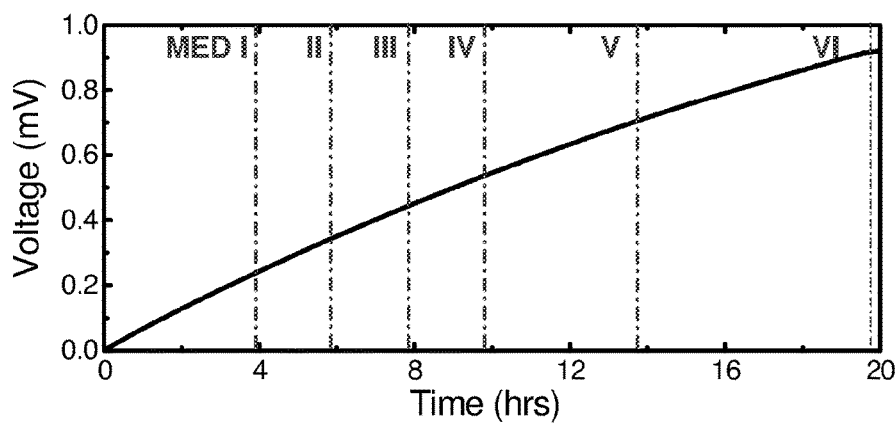
(C)
FIG. 50

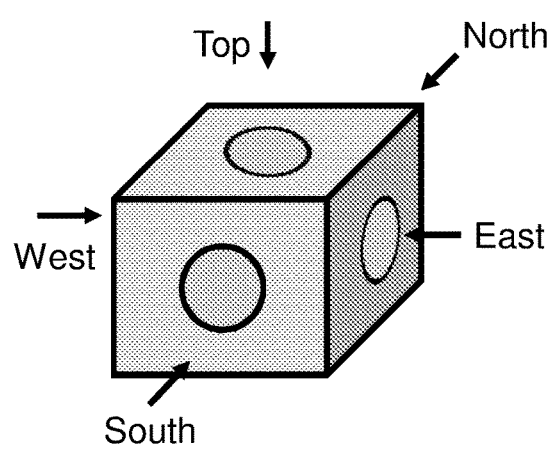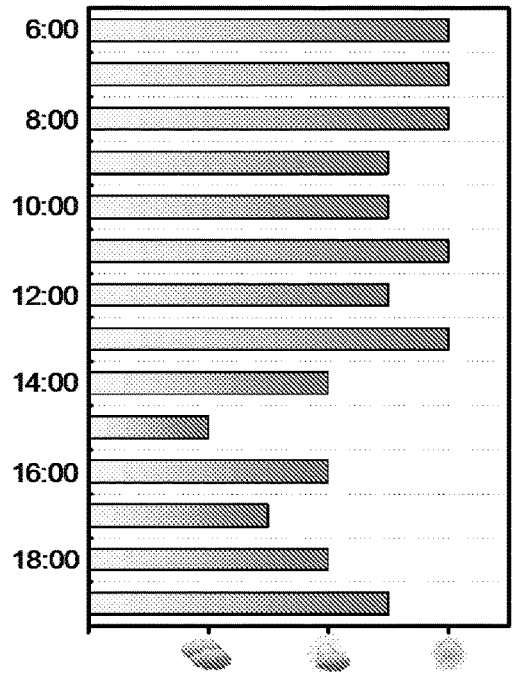
FIG. 51

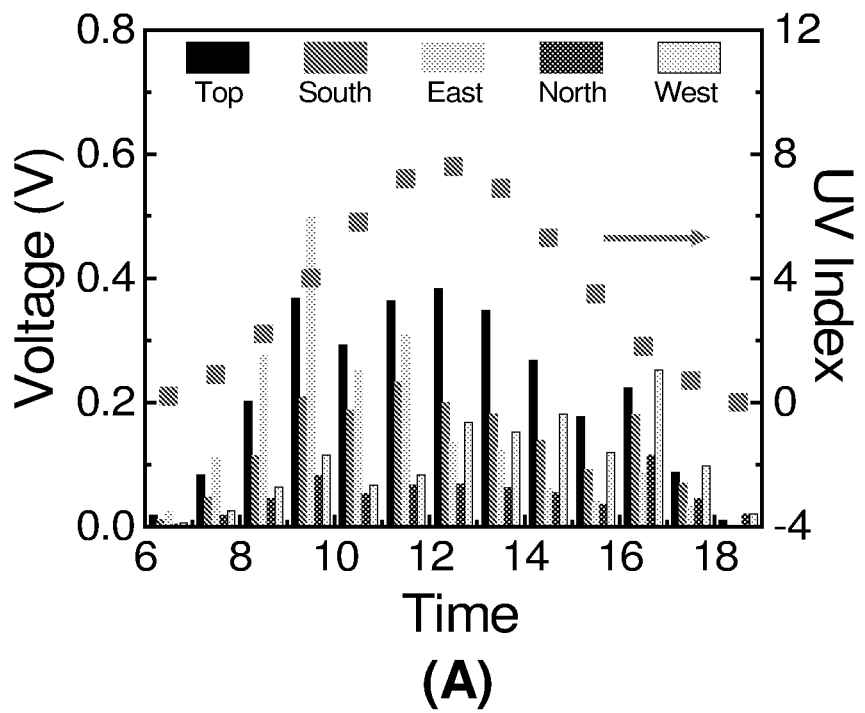
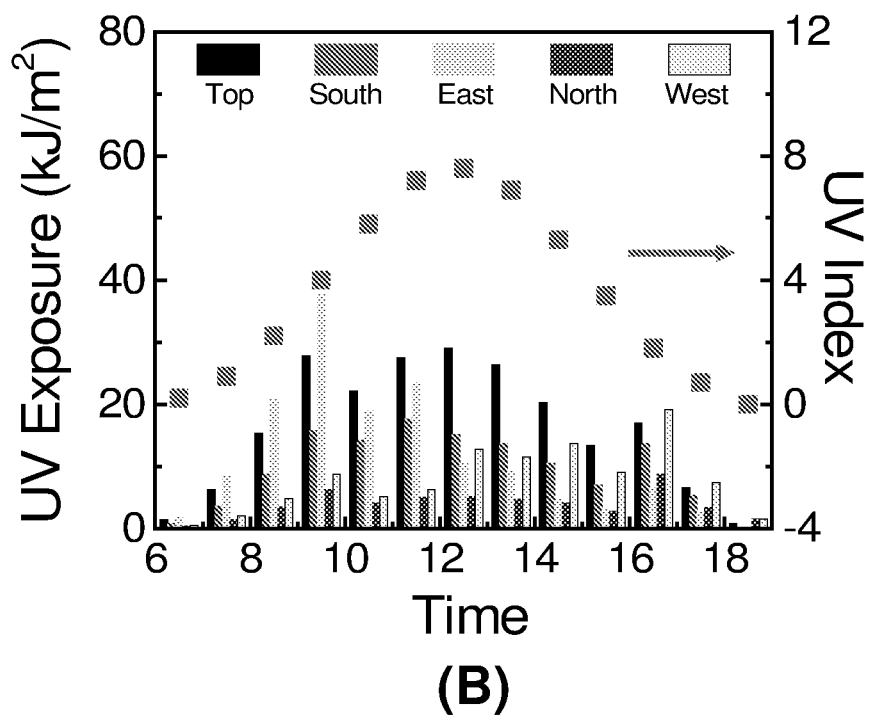
FIG. 53

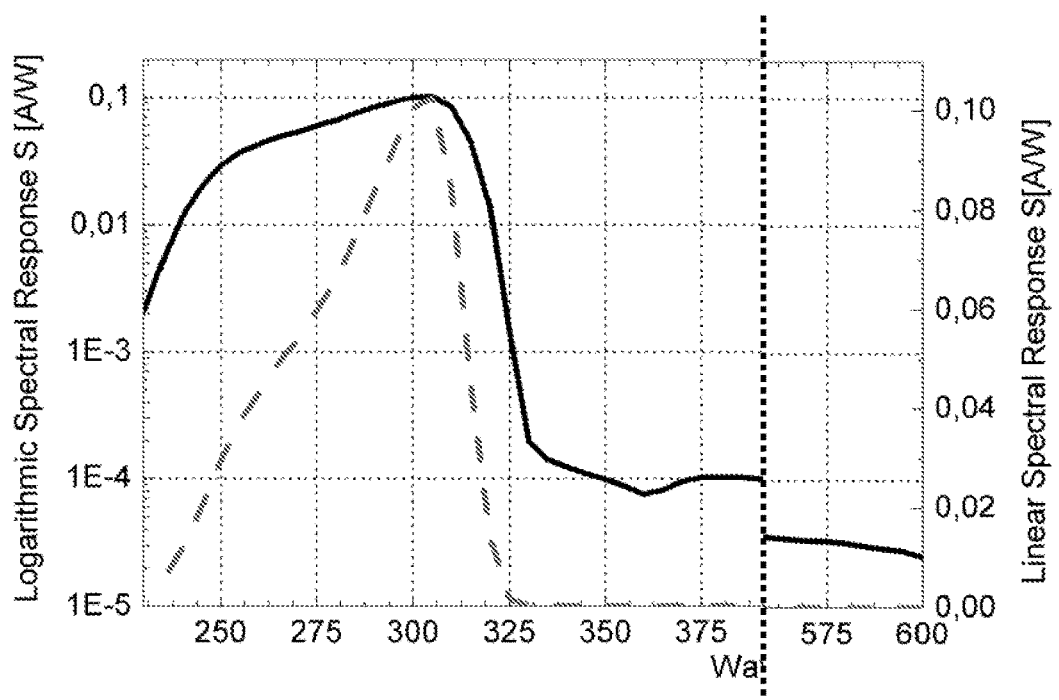
(A)
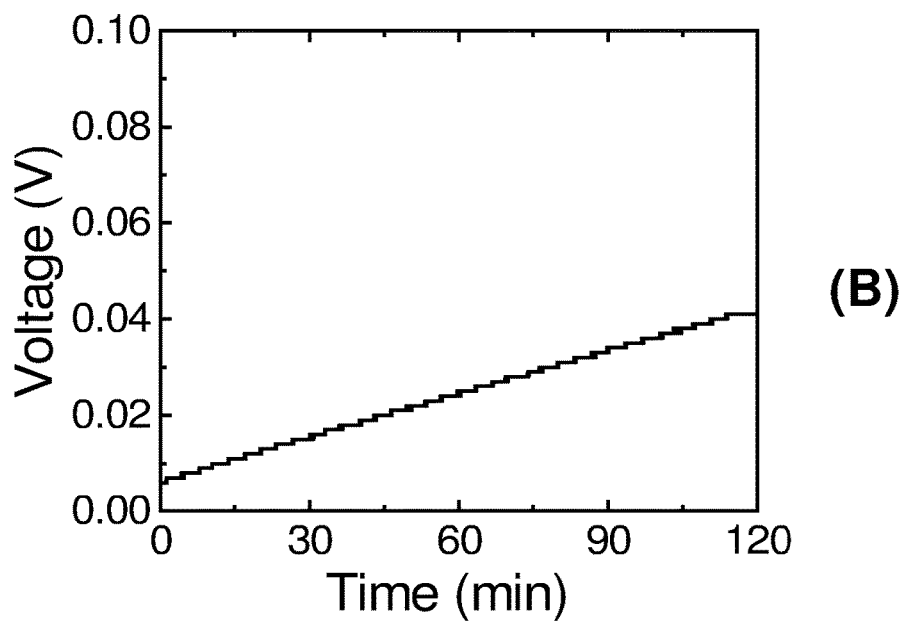
(B)
FIG. 54

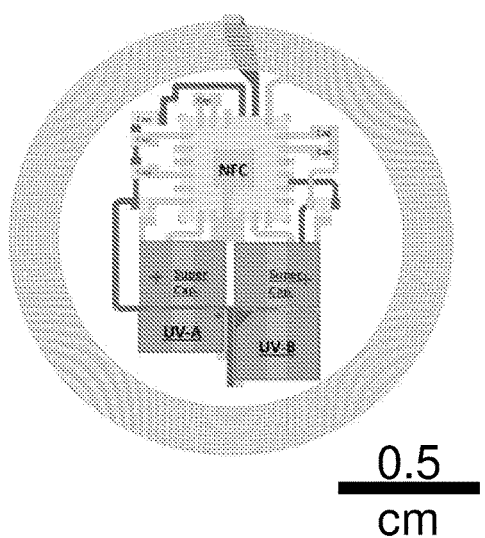
(A)
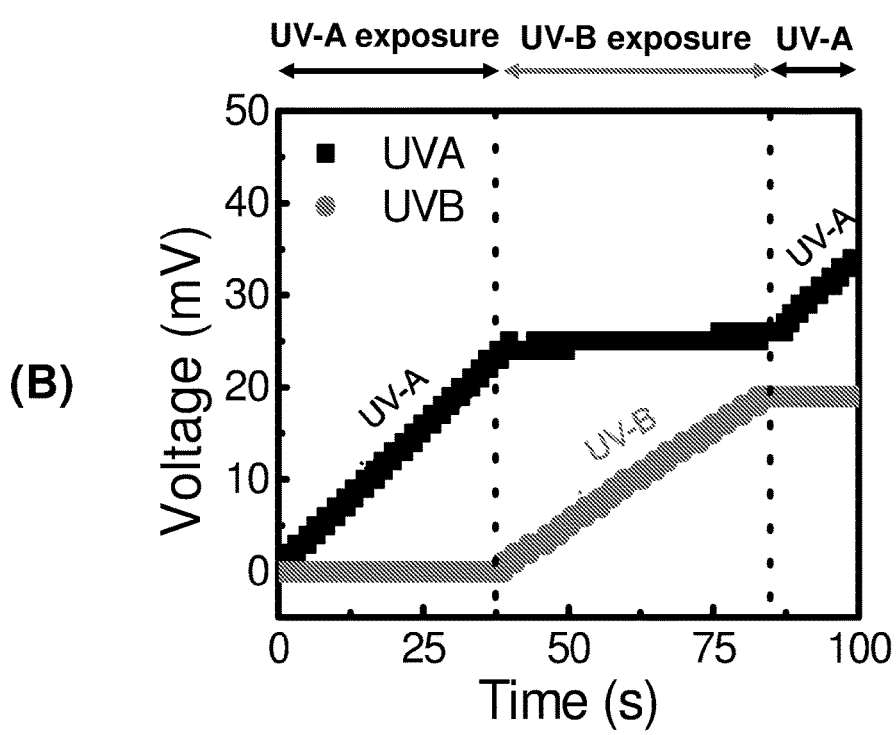
(B)
FIG. 55

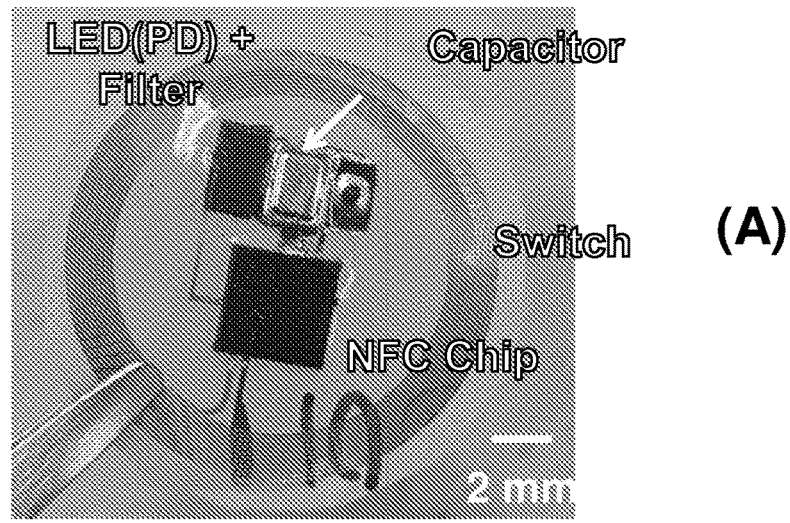
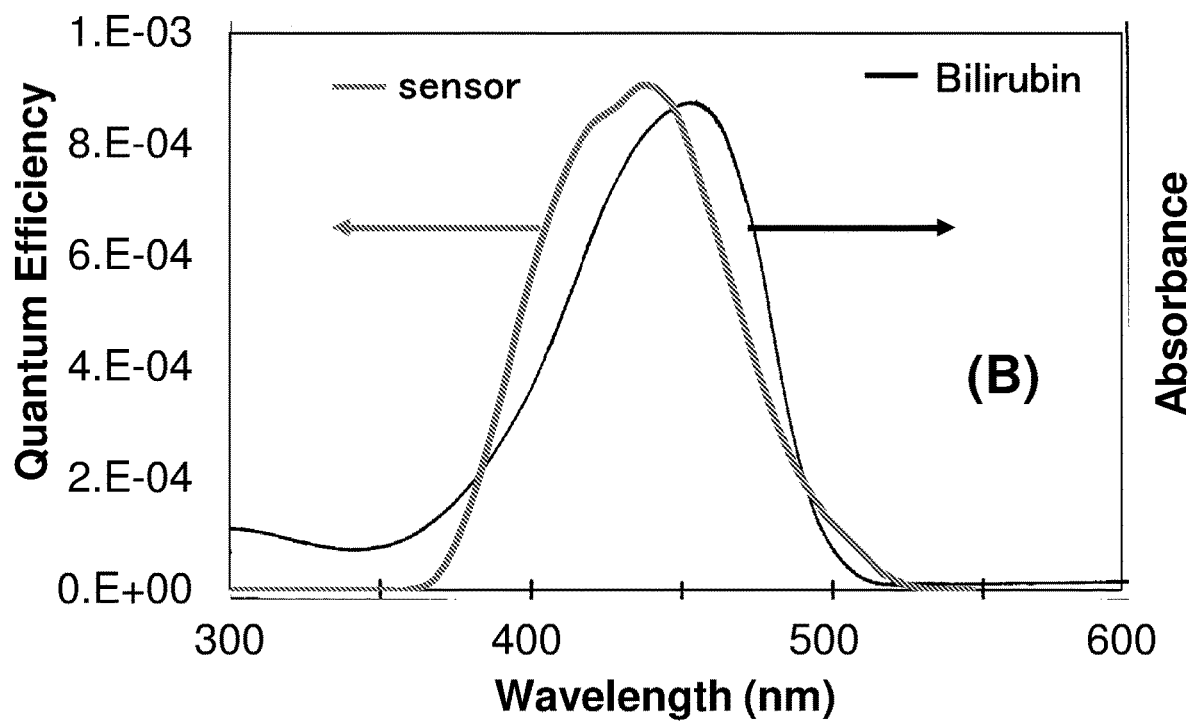
FIG. 57

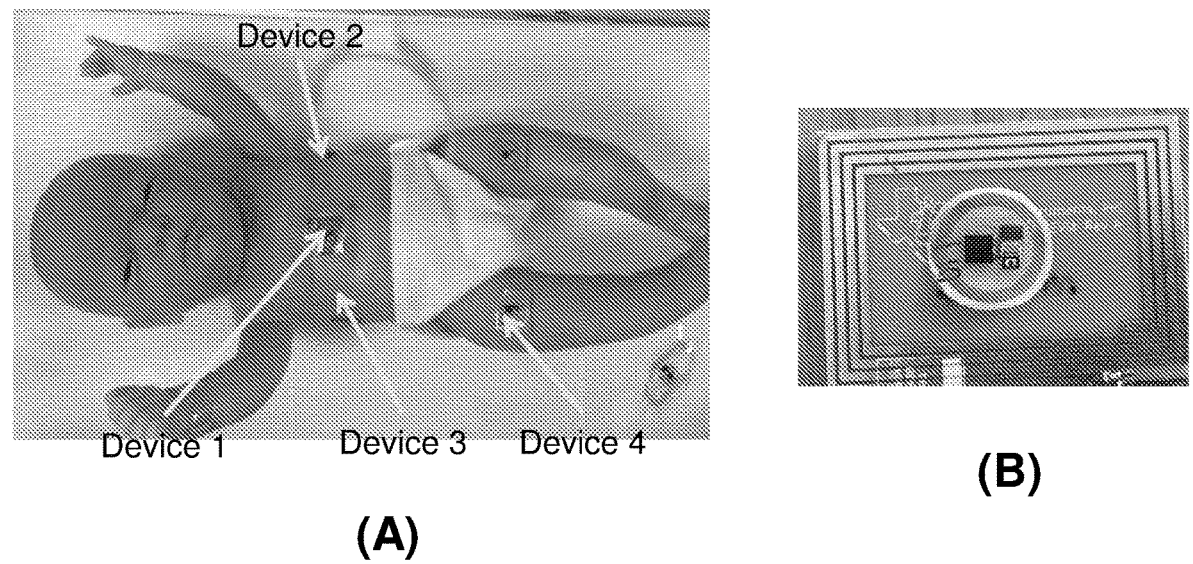
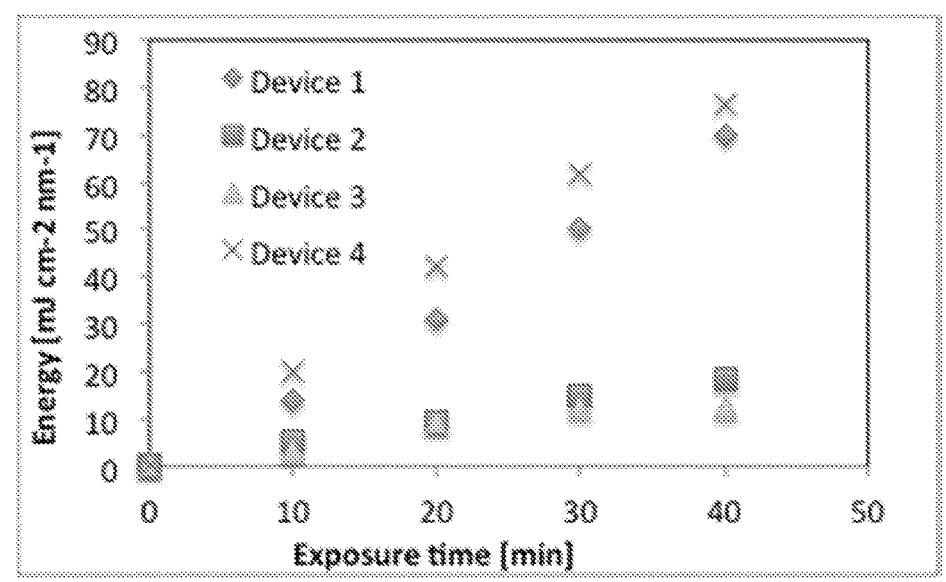
FIG. 58

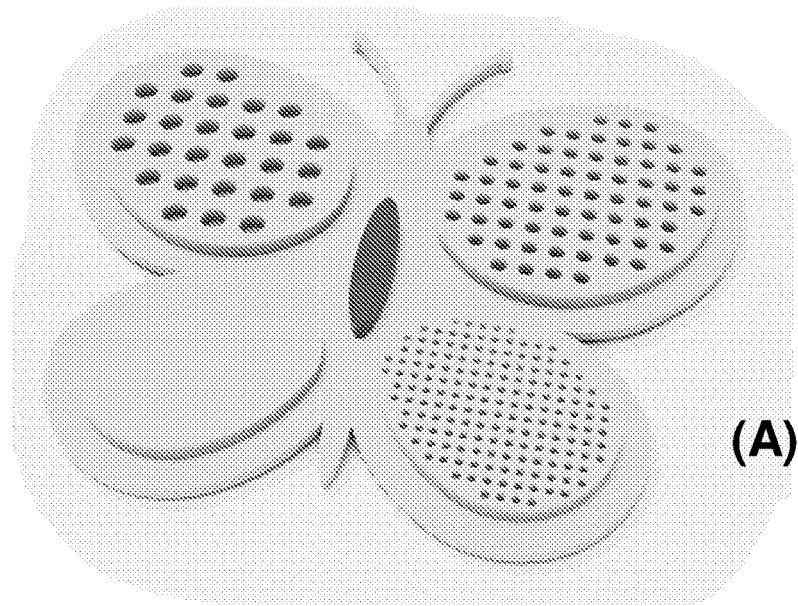
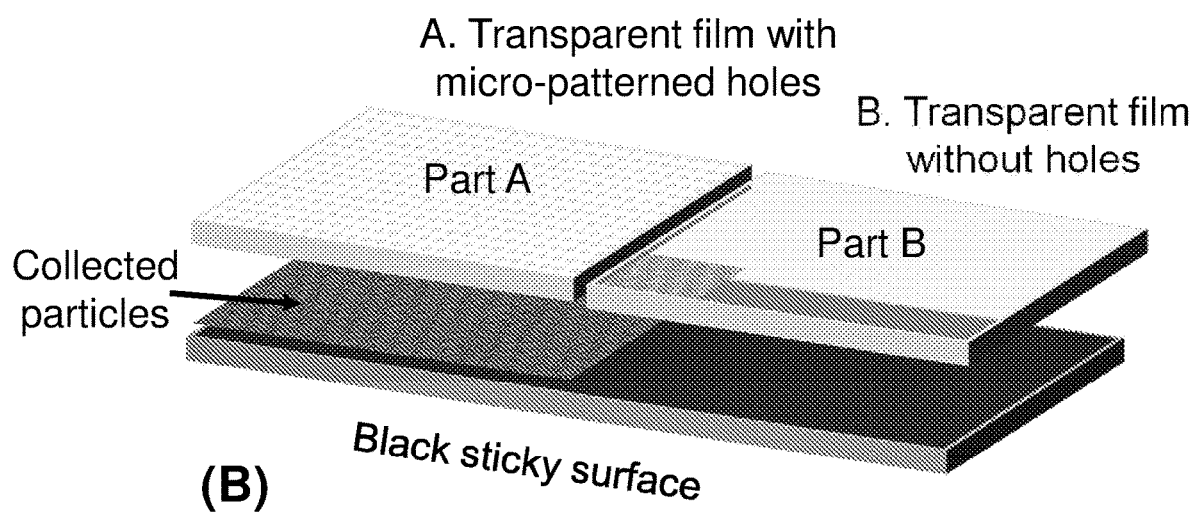
FIG. 59

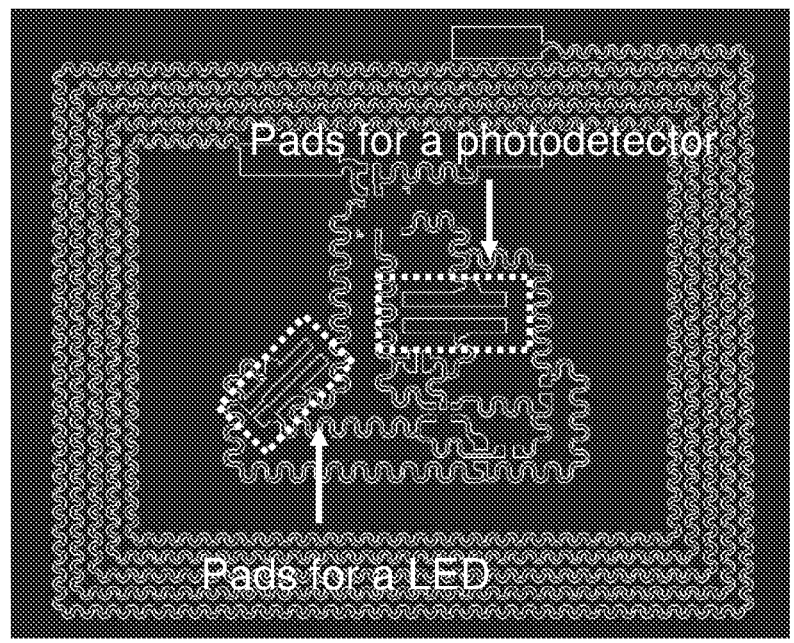
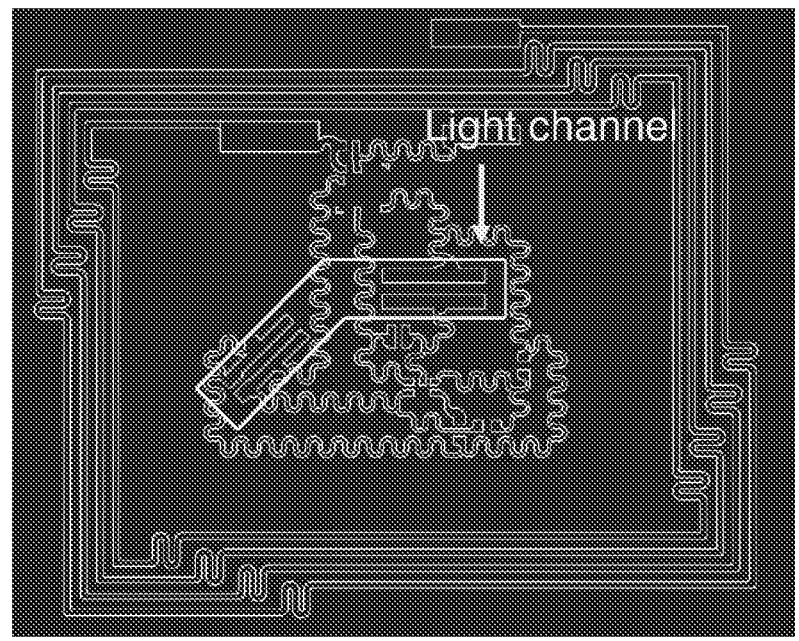
FIG. 62

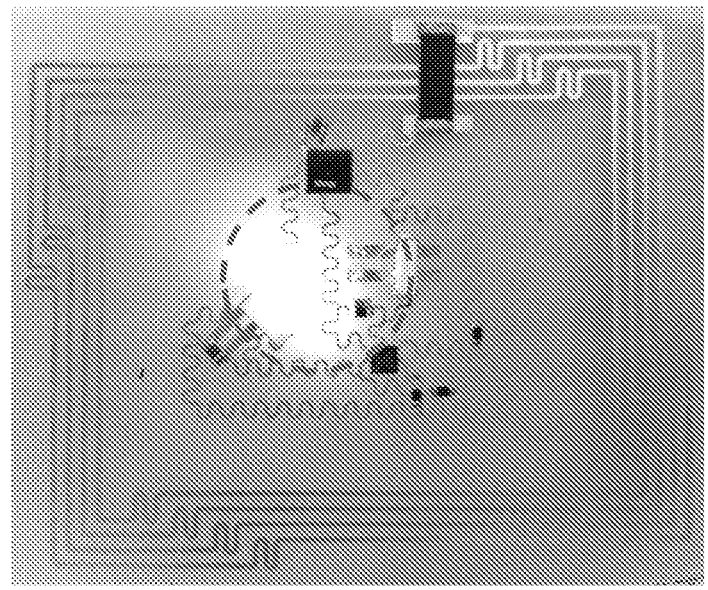
(A)
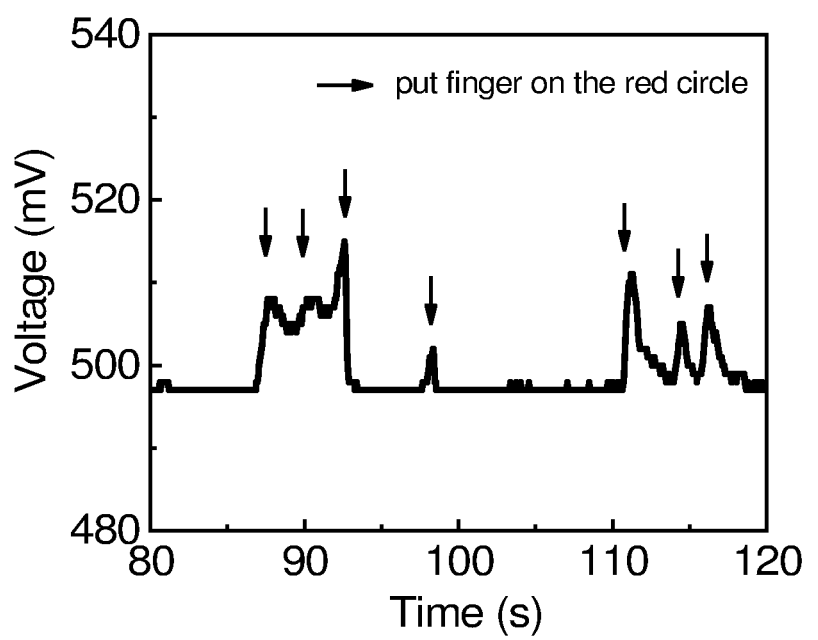
(B)
FIG. 65

ALTERNATIVE APPROACH FOR UV SENSING

CROSS REFERENCE TO RELATED APPLICATIONS

This application is a U.S. National Stage Application under 35 U.S.C. § 371 of International Application No. PCT/US2016/035331, filed Jun. 1, 2016, which claims the benefit of priority from U.S. Provisional Patent Application No. 62/169,308 filed Jun. 1, 2015, U.S. Provisional Patent Application No. 62/169,983 filed Jun. 2, 2015, U.S. Provisional Application No. 62/218,345 filed Sep. 14, 2015, and U.S. Provisional Application No. 62/218,321 filed Sep. 14, 2015, each of which is hereby incorporated by reference in its entirety to the extent not inconsistent herewith.

STATEMENT REGARDING FEDERALLY SPONSORED RESEARCH OR DEVELOPMENT

Not applicable.

BACKGROUND OF INVENTION

Accurate measurement of the exposure of a person, animal, plant or object to ultraviolet (UV), visible and infrared light is important for clinical, agricultural and environmental purposes. Digital electronic sensing technology provides an accurate and versatile means for determining exposure to UV, visible and infrared light. However, traditional approaches require bulky, expensive devices comprising integrated circuits, detectors, batteries, memory, display panels and power management systems. Such systems are not always practical or cost effective.

It will be appreciated from the foregoing that systems are needed to practically and cost effectively monitor exposure of a subject or object to electromagnetic radiation.

SUMMARY OF THE INVENTION

The invention provides systems and methods for wearable and tissue-mounted electronics for monitoring exposure of a subject or object to electromagnetic radiation, particularly electromagnetic radiation in the visible, ultraviolet and infrared portions of the electromagnetic spectrum. Devices of some embodiments of the invention implement high performance device components having miniaturized formats. In some embodiments, the devices are purely passive devices where absorption of incident electromagnetic radiation by the device provides at least a portion of the power for the measurement of the radiant exposure or flux of the incident electromagnetic radiation. In some embodiments, the invention provides complementary tissue mounting strategies providing for mechanically robust and/or long term integration of the present devices, for example, via mounting on tissue surfaces that are not subject to rapid growth or exfoliation processes such as the fingernail or toenail. Devices of the invention may include near field communication components, for example, for enabling readout by an external device, such as a computer or mobile device.

In one aspect, the invention provides a monitoring system for measuring a radiant exposure or flux of incident electromagnetic radiation comprising: a substrate and an electronic device supported by the substrate for receiving the incident electromagnetic radiation and generating an electronic signal characteristic of the radiant exposure or flux of the incident electromagnetic radiation; wherein absorption of the incident electromagnetic radiation by the device provides at least a portion of the power for the measurement of the radiant exposure or flux of the incident electromagnetic radiation. In an embodiment, for example, absorption of the incident electromagnetic radiation by the device provides at least 50%, at least 60%, at least 75%, or at least 90% of the power for said measurement of the radiant exposure or flux of said incident electromagnetic radiation, and optionally for some embodiments, all of the power for said measurement of the radiant exposure or flux of said incident electromagnetic radiation In an embodiment, the electronic device does not include a battery or solar cell configured to provide power to said electronic device. In an embodiment, the system continuously monitors the radiant exposure or flux of incident electromagnetic radiation received by the electronic device. In an embodiment, the system monitors the cumulative flux of incident electromagnetic radiation received by the electronic device.

In an embodiment, the system is wearable or tissue-mounted. For example, an inner surface of the substrate may be capable of being conformally integrated with a tissue surface. In embodiments, the tissue is skin, bone or a nail.

In some embodiments, the electronic device comprises a transducer for converting at least a portion of the incident electromagnetic radiation into an electrical current. In some embodiments, the transducer is reverse-biased. In some embodiments, the transducer comprises one or more diodes. For example, the transducer may comprise one or more light emitting diodes (LEDs), where the one or more LEDs are characterized by absorption in the ultraviolet, visible or infrared regions of the electromagnetic spectrum. In an embodiment, the one or more LEDs are characterized by a band gap selected from the range of 6 eV to 1 eV, or 5 eV to 1.5 eV, or 4 eV to 2 eV. In an embodiment, the one or more LEDs are characterized by a conversion efficiency selected from the range of 1% to 90%, or 5% to 80%, or 10% to 75%, or 20% to 60%. In an embodiment, the one or more LEDs are characterized by a spectral response selected from the range of 200 nm to 1200 nm, or 220 nm to 1000 nm, or 280 nm to 800 nm.

In some embodiments, the electronic device further comprises an energy storage device in electrical communication with said transducer, wherein said electrical current transmitted from said transducer is stored in the energy storage device. In some embodiments, the energy storage device is characterized by a leakage of the total charge stored in the energy storage device of less than or equal to 5% for a given time interval, such as the time interval between successive readouts. In some embodiments, the energy storage device is characterized by a capacitance selected over the range of 1 µF to 1 F, or 50 µF to 100 mF, or 10 µF to 14 mF. For some applications, such as non-wearable applications, monitoring systems of the present invention may comprise energy storage devices characterized by a capacitance less than or equal to 1 F. For some applications, such as wearable applications, monitoring systems of the present invention may comprise energy storage devices characterized by a capacitance less than or equal to 14 mF. In some embodiments, the energy storage device is a capacitor or a supercapacitor.

In some embodiments, the electronic device further comprises a readout generator for generating an output signal corresponding to the amount of energy stored in the energy storage device. For example, the readout generator may be a near field communication (NFC) chip. In some embodiments, the output signal is a wireless output signal.

In some embodiments, the electronic device further comprises one or more optical filters positioned to optically filter the incident electromagnetic radiation received by the system. Typically, the optical filters optically filter the incident electromagnetic radiation such that the radiant exposure or flux of incident electromagnetic radiation corresponds to a preselected wavelength range. In an embodiment, the one or more optical filters are thin film filters. In an embodiment, the optical filters are neutral density filters or bandpass filters. A neutral density filter may, for example, adjust the flux of incident electromagnetic radiation reaching the energy storage device to ensure compatibility with component specifications, such as a readout threshold for a near field communication chip.

In some embodiments, the monitoring system further comprises a near-field coil for wirelessly coupling the system with an external electronic device. In an embodiment, the external electronic device receives and stores voltage data from the system. In an embodiment, the external electronic device emits a reset signal capable of shorting the energy storage device. In an embodiment, the near-field coil has a diameter selected from the range of 500 microns to 20 millimeters, or selected from the range of 700 microns to 5 millimeters, or selected from the range of 800 microns to 2 millimeters, or selected from the range of 900 microns to 1500 microns. In an embodiment, the near-field coil has an average thickness selected from the range of 1 micron to 5 millimeters, or selected from the range of 10 microns to 2 millimeters, or selected from the range of 100 microns to 1 millimeter. In an embodiment, the coil has a geometry selected from an annulus and an elliptical annulus.

In an embodiment, the system further comprises a temperature sensor, for example, wherein said temperature sensor provides for continuous measurement of ambient temperature or measurement of ambient temperature at discrete intervals.

In some embodiments, the system further comprises a power source, such as a battery, an energy harvester, a solar cell, a piezoelectric element or any combination of these. Such a power source may, for example, provide power for a processor, optionally including memory, an NFC chip, or other components of a monitoring system.

In some embodiments, the electronic device comprises a plurality of transducers, wherein each transducer converts incident electromagnetic radiation having a different range of wavelengths into an electrical current. In an embodiment, the transducers include a first transducer that absorbs electromagnetic radiation having wavelengths between 320 nm and 400 nm and a second transducer that absorbs electromagnetic radiation having wavelengths between 280 nm and 320 nm. In an embodiment, the first transducer is a UVA LED and the second transducer is a UVB LED.

In some embodiments, the electronic device is at least partially encapsulated by the substrate or one or more encapsulation layers. In an embodiment, for example, the electronic device is waterproof. In some embodiments, the electronic device is a flexible electronic device, a stretchable electronic device or a rigid electronic device. In an embodiment, the electronic device comprises an inorganic semiconductor component, an organic semiconductor component, a metallic conductor component or combinations of these. In an embodiment, the inorganic semiconductor component, the organic semiconductor component, or the metallic conductor component has a thickness selected from the range of 50 microns to 10000 microns, or selected from the range of 100 microns to 5000 microns, or selected from the range of 250 microns to 1500 microns. In an embodiment, the inorganic semiconductor component, the organic semiconductor component, or the metallic conductor component has a thickness greater than 50 microns.

In embodiments, monitoring systems of the present invention are tissue mounted systems or systems that are conformally integrated with tissue.

As used herein, the term "tissue-mounted" is intended to broadly include a class of systems that upon implementation are supported by one or more tissue surfaces. In some embodiments, upon implementation, tissue-mounted systems of the invention are supported directly by a tissue surface, for example, wherein a surface of the system, such as a substrate surface, is in physical contact with the tissue surface, such as in conformal contact. In some embodiments, upon implementation, tissue-mounted systems of the invention are supported indirectly by a tissue surface, for example, wherein a surface of the system, such as a substrate surface, is in physical contact with an intermediate structure, such as an integration platform, provided between the tissue surface and the tissue-mounted system. A tissue mounted system may be coupled to the body by a wide variety of intermediate structures supported by the body including manufactured materials and non-natural materials. In some embodiments, for example, a tissue mounted system may be directly or indirectly coupled to the body by faux nails (i.e., false finger nails), teeth, clothing (buttons, tags, woven material, etc), jewelry (e.g., rings, bracelets, necklaces, wrist watches, piercings, etc.), body-enhancements, glasses, gloves, nail polish and the like.

Conformal integration refers to the ability of the present systems to be provided to a tissue in a manner that the device spatially conforms at an interface between the system and the tissue or at the interface with an intermediate structure provided between the system and tissue surface. Conformal integration may be via direct or indirect contact with a tissue surface. Tissue mounted systems of the invention may be provided in direct conformal integration, wherein the system itself establishes conformal contact with the tissue surface. Tissue mounted systems of the invention may be provided in indirect conformal integration, wherein the system is provided on an intermediate structure provided in conformal contact with the tissue surface, such as a prosthetic, adhesive tape, faux nails (i.e., false finger nails), clothing (buttons, tags, woven material, etc), jewelry (e.g., rings, bracelets, necklaces, wrist watches, piercings, etc.), body-enhancements, glasses, gloves, nail polish and the like.

In an embodiment, the inner surface of the substrate conforms to the curvature of a tissue surface. In embodiments, inorganic components are selected from inorganic semiconductor components, metallic conductor components and combinations of inorganic semiconductor components and metallic conductor components.

Systems and methods of some aspects of the invention exploit overall size miniaturization to achieve a mechanically robust interface with a tissue surface without generating stresses or strains adversely impacting performance and/or to minimize adverse physical effects to tissue. In embodiments, for example, the system has a lateral area footprint less than or equal to 500 $mm^2$, or less than or equal to 300 $mm^2$, or selected from the range of 1 $mm^2$ to 500 $mm^2$, or selected from the range of 10 $mm^2$ to 500 $mm^2$, or selected from the range of 10 $mm^2$ to 300 $mm^2$. In an embodiment, the system has an areal mass density selected from the range of 0.1 mg $cm^{-2}$ to 100 mg $cm^{-2}$, 1 mg $cm^{-2}$ to 100 mg $cm^{-2}$. In embodiments, the system has an average thickness selected from the range of 5 microns to 5 millimeters, or, for example, greater than 5 microns.

Systems and methods of some aspects of the invention integrate thin, flexible functional components and substrates to provide sufficient mechanical compliance to achieve a conformal interface at the mounting site for a tissue surface. Advantages of mechanically flexible systems of the invention include the ability to conform to complex contoured tissue surfaces and/or tissue surfaces that are dynamic with respect to time. Alternatively, the invention also includes rigid systems integrating rigid functional components and/or substrates, for example, for integration with tissue types having compatible physical properties, such as the fingernail or toenail. Advantages of mechanically rigid systems of the invention include providing high functionality systems, where thin, mechanically flexible construction might represent a disadvantage, in terms of potential damage during manipulation.

In embodiments, the system has an average modulus selected from the range of 10 kPa to 100 GPa, or 10 kPa to 10 GPa, or greater than 10 kPa, optionally greater than 10 MPa. In embodiments, the system has a flexural rigidity or net bending stiffness selected from the range of 0.1 nN m to 1 N m. In an embodiment, the system has a net bending stiffness of greater than 0.1 nN m, optionally for some applications greater than 10 nN m, and optionally for some applications greater than 1000 nN m. In some embodiments, for example, one or more mechanical properties of the system, such as average modulus, flexural rigidity or bending stiffness, are matched to properties of the tissue at the mounting site; e.g., within a factor of 5.

Systems of the invention include multilayer devices, for example, wherein functional layers having electronically and/or optoelectronically functional device components are separated from each other by structural layers, such as electrically insulating or supporting layers or coatings. In embodiments, the system has a multilayer geometry comprising a plurality of functional layers, supporting layers, encapsulating layers, planarizing layers or any combination of these. In embodiments, the system has a shape selected from the group consisting of elliptical, rectangular, circular, serpentine and/or irregular. In an embodiment, the shape is characterized by an aspect ratio of a lateral dimension to thickness selected from the range of 5 to 1.

Substrates having a range of physical and chemical properties are useful in the systems and methods of the present invention. The invention includes substrates having functionality as electrical insulators, optical transparency, optical filtering, and/or functionality as a mechanically supporting layer.

In embodiments, the substrate is a flexible substrate, a stretchable substrate or a rigid substrate. In an embodiment, the substrate is characterized by an average modulus selected from the range of 10 kPa to 100 GPa, or 10 kPa to 10 GPa, or greater than 10 kPa, optionally for some applications greater than 10 kPa. In an embodiment, the substrate is characterized by an average thickness selected from the range of 50 microns to 10 millimeters, and in some embodiments, greater than 50 microns, optionally for some embodiments greater than 500 microns.

In an embodiment, the substrate comprises one or more thin films, coatings or both. For example, in some embodiments, a coating or thin film is provided directly on the electronic device or component thereof, and in some embodiments, in direct physical contact. In some embodiments, however, the coating or thin film is provided on an intermediate structure positioned between the electronic device and the coating or film. In embodiments, the substrate comprises an inorganic polymer, an organic polymer, a plastic, an elastomer, a biopolymer, a thermoset polymer, a rubber, an adhesive tape or any combination of these. For example, in embodiments, the substrate comprises polyimide, polydimethylsiloxane (PDMS), polyurethane, cellulose paper, cellulose sponge, polyurethane sponge, polyvinyl alcohol sponge, silicone sponge, polystyrene, epoxy, polymethyl methacrylate (PMMA) or polycarbonate.

A range of functional electronic device components and device integration strategies are compatible with the present methods and systems, thereby supporting expansive applications in wearable electronics. In an embodiment, for example, the system further comprises one or more encapsulating layers or coatings for encapsulating the electronic device. In embodiments, the electronic device is a flexible electronic device or a stretchable electronic device. In embodiments, for example, the inorganic component comprises one or more thin films, nanoribbons, microribbons, nanomembranes or micromembranes. In an embodiment, the inorganic component comprises a single crystalline inorganic semiconductor material.

In an embodiment, for example, the inorganic component has a thickness selected from the range of 50 microns to 100000 microns, for some applications a range of 50 microns to 2000 microns. In an embodiment, for example, the inorganic component has a thickness greater than 50 microns. In an embodiment, the inorganic component is characterized by a curved geometry, for example, a bent, coiled, interleaved or serpentine geometry. In an embodiment, the inorganic component is characterized by one or more island and bridge structures.

In embodiments, the electronic device has a multilayer geometry comprising a plurality of functional layers, barrier layers, supporting layers and encapsulating layers. In an embodiment, the electronic device is provided proximate to a neutral mechanical surface of the system.

In embodiments, the electronic device comprises one or more energy storage systems or a component thereof, for example, energy storage systems or components thereof selected from the group consisting of an electrochemical cell, a fuel cell, a photovoltaic cell, a wireless power coil, a thermoelectric energy harvester, a capacitor, a supercapacitor, a primary battery, a secondary battery and a piezoelectric energy harvester.

In embodiments, the electronic device comprises one or more communication systems or a component thereof, for example, communication systems or components thereof selected from the group consisting of a transmitter, a receiver, a transceiver, an antenna, and a near field communication device.

In embodiments, the electronic device comprises one or more coils, for example, inductive coils or near-field communication coils. In an embodiment, each of the near-field communication coils independently has a diameter selected from the range of 50 microns to 20 millimeters. In an embodiment, for example, each of the near-field communication coils independently has an average thickness selected from the range of 1 micron to 500 microns. In an embodiment, for example, an edge-to-edge diameter of each of the near-field communication coils changes by less than 20% upon change from a planar configuration to a bent configuration characterized by a radius of curvature selected over the range of 1 mm to 20 mm. In an embodiment, the one or more coils are at least partially encapsulated by the substrate or one or more encapsulation layers. In embodiments, for example, the one or more coils have a geometry selected from the group consisting of an annulus or an elliptical annulus.

In an aspect, the system of the invention further comprises a mounting platform to provide effective integration with one or more tissue surfaces. In some embodiments, for example, the mounting platform has an external surface for establishing contact with a surface of said tissue and an internal surface for supporting said electronic device and substrate. In an embodiment, the mounting platform is the substrate component of the system itself. In an embodiment, said mounting platform is for establishing conformal contact with said tissue surface, such as establishing conformal contact with a surface of a fingernail. The invention includes mounting platform components that are rigid or flexible. In an embodiment, the mounting platform is a prosthetic. In an embodiment, the mounting platform is an adhesive tape. In an embodiment, the mounting platform is a false fingernail. In an embodiment, the mounting platform is jewelry. In an embodiment, the mounting platform is clothing.

In an embodiment, for example, the inner surface of the substrate is capable of establishing contact with a tissue surface. In embodiments, the external tissue is skin, a fingernail, a toenail, tooth, bone or an ear lobe. In embodiments, for example, the inner surface of the substrate is bonded to the tissue surface via an adhesive, such as an acrylic. In an embodiment, the system further comprises a near field communication device. In an embodiment, the near field communication device is for communicating with an external electronic device, such as a computer or mobile electronic device.

In an aspect, the present invention is a method for making a monitoring system for measuring the radiant exposure or flux of incident electromagnetic radiation, comprising: providing a substrate and providing an electronic device supported by the substrate for receiving the incident electromagnetic radiation and generating an electronic signal characteristic of the radiant exposure or flux of the incident electromagnetic radiation, wherein absorption of the incident electromagnetic radiation provides at least a portion of the power for the measurement of the radiant exposure or flux of the incident electromagnetic radiation. In an embodiment, for example, the step of providing the substrate, providing the electronic device or both is carried out in an industrial process using a roll-to-roll process. In an embodiment, for example, the roll-to-roll process comprises web processing or reel-to-reel processing. In an embodiment, for example, the system is fabricated using a roll of flexible plastic or metal foil.

In an aspect, the present invention is a method of using a monitoring system for measuring the radiant exposure or flux of incident electromagnetic radiation, comprising: mounting a monitoring system on a subject, the monitoring system comprising: a substrate and an electronic device supported by the substrate for receiving the incident electromagnetic radiation and generating an electronic signal characteristic of the radiant exposure or flux of the incident electromagnetic radiation; wherein absorption of the incident electromagnetic radiation by the device provides at least a portion of the power for the measurement of the radiant exposure or flux of the incident electromagnetic radiation; exposing the electronic device of the monitoring system to the electromagnetic radiation; and measuring the electronic signal. In an embodiment, for example, the incident electromagnetic radiation is solar radiation. In an embodiment, for example, the monitoring system is a wearable or a tissue mounted system provided on a subject or an object. In an embodiment, for example, the monitoring system is provided on the skin, bone or finger nail of the subject.

In an aspect, the invention provides a monitoring system for measuring an ambient parameter comprising: (i) a substrate; and (ii) an electronic device supported by the substrate; wherein the electronic device absorbs ambient energy, wherein absorption of the ambient energy by the device provides at least a portion of the power for the measurement of the ambient parameter. In an embodiment, for example, the ambient parameter is a thermal parameter, an optical parameter, an electrical parameter or a mechanical parameter. In an embodiment, for example, the ambient parameter is temperature, strain, radiant exposure or flux of incident electromagnetic radiation. In an embodiment, for example, the ambient parameter is electromagnetic radiation, ionizing radiation, heat, movement, strain, pollution, particle concentration, humidity, pressure, the presence of gases (such as volatile organic compounds, VOCs), motion (e.g., acceleration and gyration), sound, a magnetic force or a combination thereof. In an embodiment, for example, the electronic device detects UV intensity and/or dose. In an embodiment, for example, the electronic device detects color. In an embodiment, for example, the electronic device comprises an accelerometer, a gyroscope, a spectrometer, a pressure sensor, a barometer, a strain sensor, a humidity sensor, a heat sensor, a radiation sensor, a sound detector, a magnetic sensor or a combination thereof.

In an embodiment, the electronic device comprises a transducer for converting the ambient energy to electrical current, for example, wherein the transducer comprises a piezoelectric element, a thermoelectric element, or a diode. In an embodiment, the electronic device further comprises an energy storage device in electrical communication with the transducer, wherein the electrical current transmitted from the transducer is stored in the energy storage device. In an embodiment, for example, the energy storage device is characterized by a leakage of the total charge stored in the energy storage device of less than or equal to 5% for a given time interval, such as the time interval between successive readouts. In an embodiment, the energy storage device is a capacitor or a supercapacitor. In an embodiment, the electronic device further comprises a readout generator for generating an output signal corresponding to the amount of energy stored in the energy storage device, for example, wherein the readout generator is a near field communication (NFC) chip and/or wherein the output signal is a wireless output signal.

The invention includes mounting strategies supportive of a range of applications for wearable electronics. In an embodiment, for example, the tissue surface comprises an external tissue of a subject, such as a human or nonhuman subject. In an embodiment, for example, the external tissue is characterized by a growth rate less than or equal to 6 mm per month or for some embodiments less than or equal to 0.1 mm per day. In an embodiment, for example, the external tissue is characterized by a rate of exfoliation less than or equal to once per day or for some embodiments less than or equal to 0.1 mm per day. In an embodiment, for example, the external tissue is characterized by a modulus greater than or equal to 10 kPa, optionally for some embodiments greater than or equal to 10 MPa. In an embodiment, for example, the external tissue is characterized by a bending stiffness greater than or equal to 0.1 nN m, optionally for some embodiments greater than or equal to 100 nN M or greater than or equal to 1000 nNM. In an embodiment, for example, the tissue surface is characterized by a radius of curvature selected over the range of 1 mm to 25 mm.

In an embodiment, for example, the tissue is human tissue. In an embodiment, for example, the tissue is skin, fingernail, toenail, tooth, or an ear lobe of a human subject. In an embodiment, for example, the tissue is not epidermal tissue. In an embodiment, for example, the tissue is not internal tissue. In an embodiment, for example, the tissue is non-human tissue, such as tissue of a non-human animal, for example for livestock or veterinary applications. In an embodiment, for example, the tissue is non-human tissue, such as tissue of a plant (e.g. leaves and/or roots), for example for agricultural applications.

In an embodiment, for example, a step of sensing one or more properties comprises sensing a discrete, substantially instantaneous signal or sensing a cumulative signal acquired over a period of time.

In an embodiment, multiple tissue mounted systems, spatially distributed from one another, may provide data indicative of a spatially or spatiotemporally varying property.

In an embodiment, communicating comprises generating or receiving a near field communication signal, for example, wherein the near field communication signal is received or generated by a computer or portable electronic device. In an embodiment, for example, the near field communication signal is for data transmission.

In an aspect, the invention provides a method of monitoring a user's activity, the method comprising: providing a tissue mounted electronic system on a tissue surface, wherein the tissue mounted electronic system comprises: a substrate having an inner surface and an outer surface; and an electronic device comprising one or more inorganic components, organic components or a combination of inorganic and organic components supported by the outer surface of the substrate; sensing a tissue property using the tissue mounted electronic system; and communicating a signal indicative of the tissue property from the tissue mounted electronic system to an external device. In an embodiment, the tissue property is selected from the group consisting of temperature, motion, respiratory rate, heart rate or combinations thereof. In an embodiment, the method of monitoring a user's activity further comprises obtaining instantaneous caloric output, cumulative caloric output or both from said signal. In an embodiment, the tissue property is selected from the group consisting of glucose concentration, insulin concentration or combinations thereof.

In an aspect, the invention provides a method of monitoring pollution, the method comprising: providing a tissue mounted electronic system on a tissue surface, wherein the tissue mounted electronic system comprises: a substrate having an inner surface and an outer surface; and an electronic device comprising one or more inorganic components, organic components or a combination of inorganic and organic components supported by the outer surface of the substrate; and sensing dust particles on the tissue mounted electronic system.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 11. Individual components for the single ADC UV dosimeter design.

FIG. 12. Examples of components for a two channel and three channel ADC UV dosimeter device.

FIG. 19. SPICE (Simulation Program with Integrated Circuit Emphasis) simulation showing the relationship between capacitor voltage, UV exposure time and leakage.

FIG. 20. Minimum Erythema Dose (MED) calibrated from a Solar Simulator was used to calibrate the UV dosimeter NFC device. MED values obtained from Fitzpatrick, T. B. (1988) Arch. Dermatol. 124(6).

FIG. 21. Calibration and adjustments needed for single ADC devices to incorporate UVB and UVA values.

FIG. 22. Comparison of two leading UV devices that measure instantaneous UV with the UV dosimeter NFC device.

FIG. 25. Experimental testing and calibration of UVB dosimeter NFC device.

FIG. 28. UV NFC dosimeter software GUI with added functionality.

FIG. 29. Screen shot of UV NFC dosimeter app compared with TI commercial NFC app.

FIG. 33. SPICE simulation vs. experimental results and corresponding model for NFC UV dosimeter devices. The experimental results were carried out using a single channel UV dosimeter device with a UV LED as a photodetector and a 11 mF super capacitor.

FIG. 36. Experimental procedure and calibration results in various daily outdoor activities.

FIG. 38. Examples of light radiation sensing in hospitals for bili light treatment of infants.

FIG. 42. (A) Picture of an oximetry device, (B) showing operable red and IR LEDs. (C) Picture of a tissue mounted oximetry device with an inset schematically showing placement of the red and IR LEDs. (D) Graphical representation of switching red and IR LEDs, showing that backscattered amplitudes for both red and IR can be captured using a single photodetector.

FIG. 47. Schematic showing the UV spectrum of bilirubin and operation of a jaundice meter on normal skin and jaundice skin with intensity indicated by number of curved lines. Bilirbubin concentration is calculated by comparing reflection intensity of blue and green light.

FIG. 48. Schematic illustrating the geometry of a bili sensor: (A) top view, (B) cross sectional view. The short path reflection can detect the color of the epidermis and the dermis. The long path reflection can detect information from the subcutaneous tissues. To check both short and long path reflections, LEDs are mounted different distances from the photodetector (PD).

FIG. 49. Graphs of (A) signal versus time from a bili sensor on a finger and (B) signal versus PD-LED distance. Different voltage values, which correspond to the reflectance, are measured with different light colors and interoptode distances.

FIG. 50. Measurements of UV-A exposure over a specified period (A) with a 1.4 mW/cm$^2$ light source having a peak wavelength of 365 nm (B). Graph of voltage versus time (C) showing that voltage values correspond to the amount of UV exposure.

FIG. 51. Test conditions for a UV sensor. (A) The devices are mounted on different locations on the box. (B) Voltage values measured with time increase during the day and correspond to the amount of sun versus cloud cover.

FIG. 53. Analysis per time with UV index. (A) Voltage versus time. (B) UV exposure versus time. The UV-A exposure amount per time shows a similar trend to the UV index.

FIG. 54. UV-B LEDs having dimensions of (L×W×H: 3.5 mm×2.8 mm×1.8 mm) were used to measure UV-B exposure over time with a 0.8 mW/cm$^2$ light source having a peak wavelength of 300 nm (A). The voltage value increases with UV-B exposure, as shown in graph (B).

FIG. 55. (A) Schematic of a sensor having UV-A and UV-B detection capabilities. (B) Voltage versus time curve.

FIG. 57. Picture of (A) a bili light sensor and (B) a graph of quantum efficiency (EQE) and bilirubin absorbance versus wavelength showing that the sensitivity of the sensor is suitable for bili light detection.

FIG. 58. Picture of (A) doll having multiple bili light sensors mounted on different parts of its body, (B) a picture of a bili light sensor and (C) a graph of energy versus exposure time showing variability between sensor readings depending upon mounting location.

FIG. 59. Schematic of (A) a dust sensor and (B) the structure of a dust sensor for colorimetric sensing of accumulated dust. Part A allows particles to pass through and Part B does not. Measuring the color difference between the black sticky surface under Part A and the black sticky surface under Part B allows for a qualitative and/or quantitative determination of dust.

FIG. 62. Stretchable designs for an optical dust sensor comprising distance-tunable pads for a LED and a photodetector, as well as a black light channel.

FIG. 65. (A) Photograph of a dust sensor comprising an IR LED and IR photodetector. (B) Graph of voltage versus time where arrows indicate that the tester placed a finger over the area of the sensor marked with a dashed circle.

DETAILED DESCRIPTION OF THE INVENTION

Figure 1:
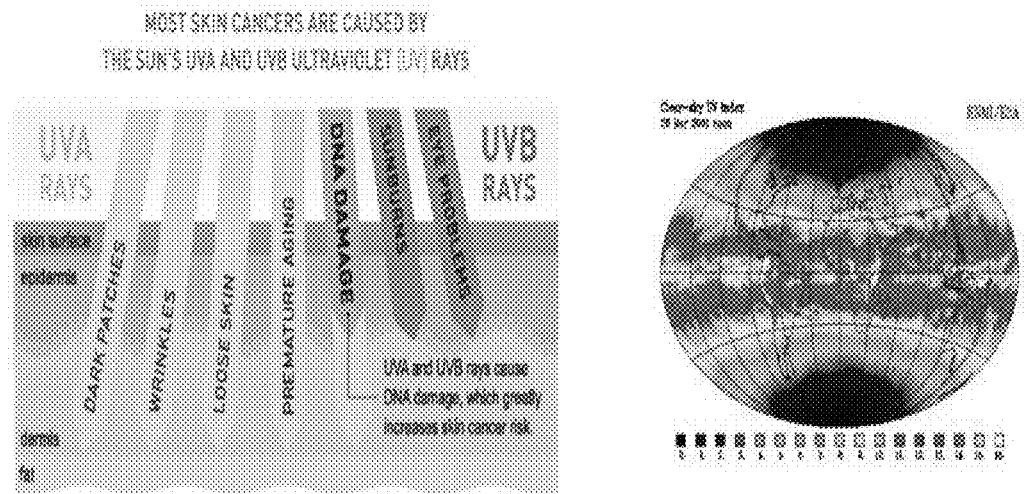
FIG. 1. Illustration of UVA and UVB effects on the human body, a plot of the intensity of the UV spectral distribution on earth, and information relating to wavelengths and percent of UVA and UVB.
Figure 2:
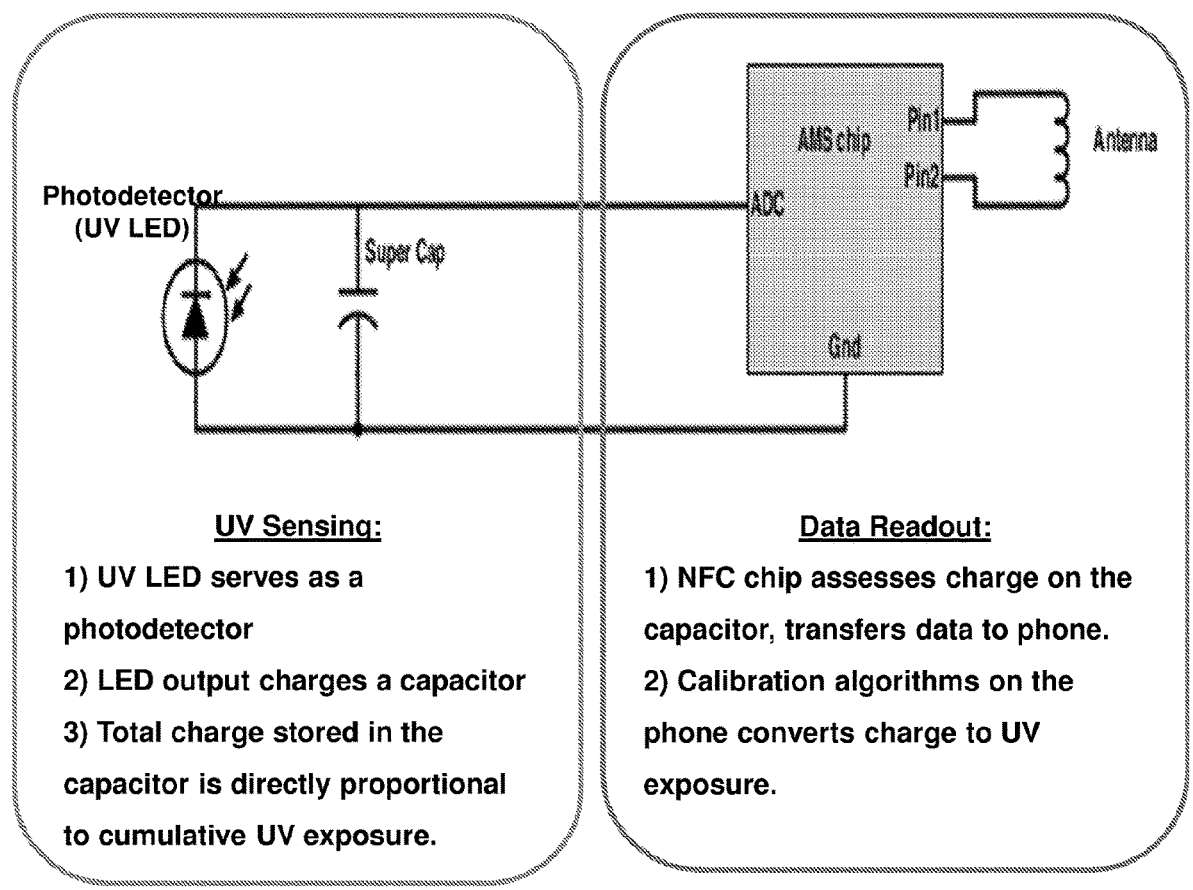
FIG. 2. Schematic illustration of a single channel dosimeter utilizing a NFC chip having an internal temperature sensor with internal analog to digital converter (ADC), and a single external (ADC) input channel. Other components include a coil antenna with a resonant frequency compatible with NFC enabled devices, a capacitor that serves as an energy storage device typically in the range of micro to milli Farad range (dependent on desired device sensitivity), and a single LED, which has a photon absorption spectrum in the UV range and serves as a photodetector.
Figure 3:
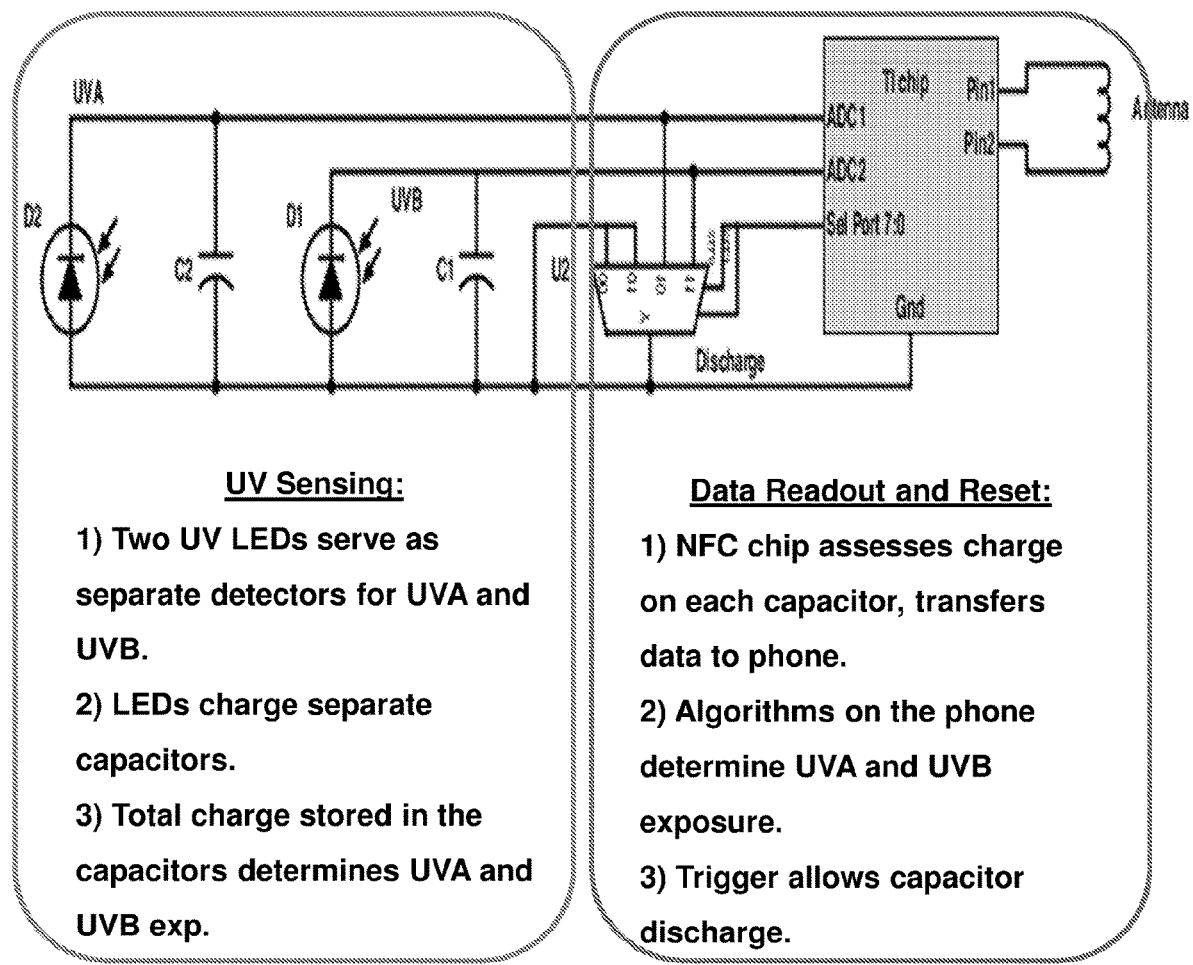
FIG. 3. Schematic illustration of a two channel dosimeter utilizing a NFC chip having an internal temperature sensor with internal analog to digital converter (ADC), one I/O port and two external (ADC) input channels. Other components include a coil antenna with a resonant frequency compatible with NFC enabled devices, two capacitors each serving as an independent energy storage device for each ADC channel typically in the range of micro to milli Farad range (dependent on desired device sensitivity), two LEDs (one per ADC channel) having photon absorption spectra in the UV range serving as photodetectors, and a multi MOSFET transistor serving as a reset switch trigger.
Figure 4:
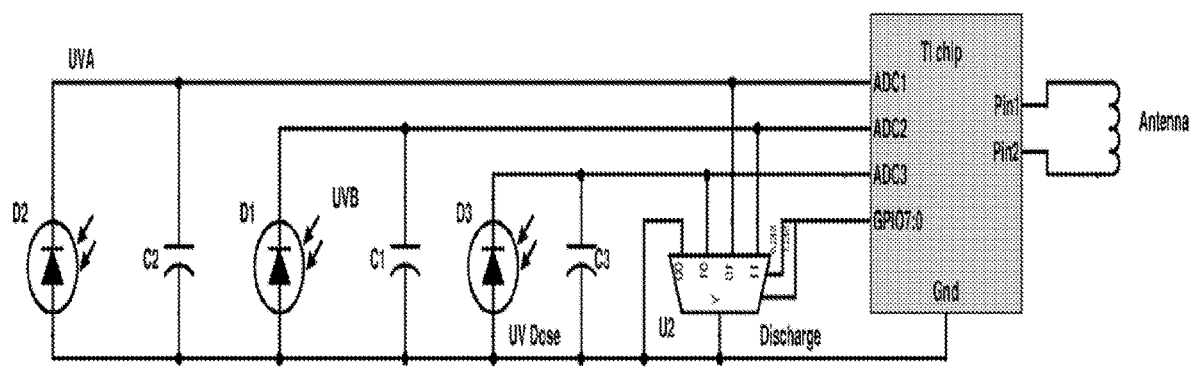
FIG. 4. Schematic illustration of a three channel dosimeter utilizing a NFC chip having an internal temperature sensor with internal analog to digital converter (ADC), one I/O port and three external (ADC) input channels. Other components include a coil antenna with a resonant frequency compatible with NFC enabled devices, three capacitors each serving as an independent energy storage device for each ADC channel typically in the range of micro to milli Farad range (dependent on desired device sensitivity), three LEDs (one per ADC channel) having photon absorption spectra in the UV range serving as photodetectors, or alternately a photodetector instead of an LED in the UV range (an LED or PD can be interchanged, depending on desired sensitivity), and a multi MOSFET transistor serving as a reset switch trigger.
Figure 5:
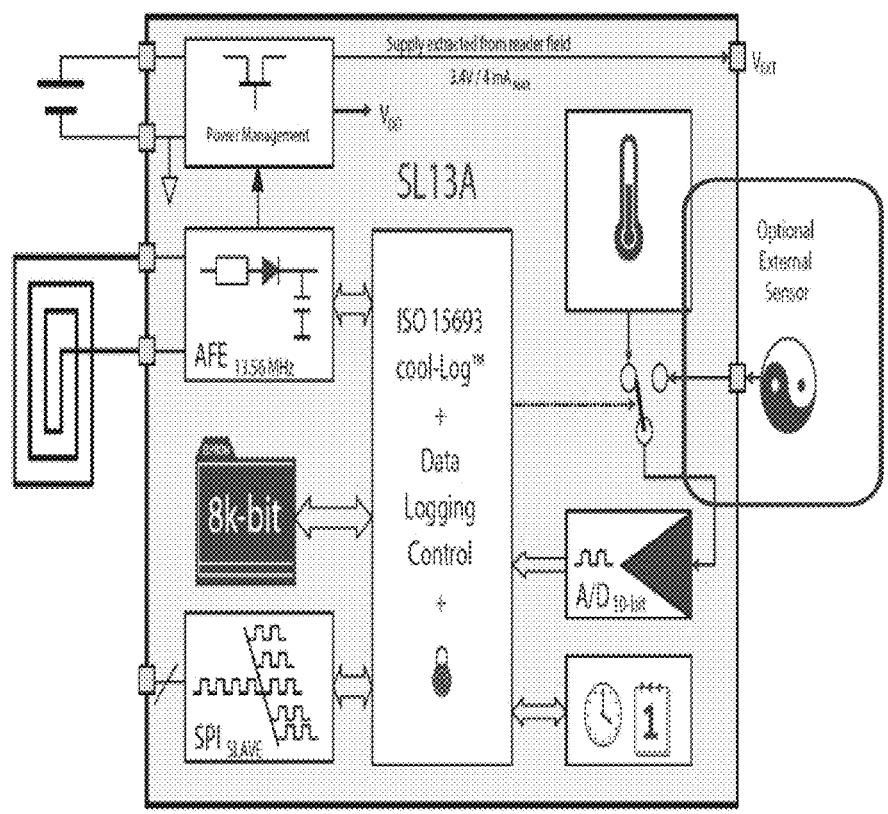
FIG. 5. Schematic of NFC chip layout and illustration of a SL13A NFC chip used in some NFC dosimeter designs compatible with the single NFC dosimeter design shown in FIG. 2. A single ADC channel is used by an internal temperature sensor and/or an external ADC input signal, an analog front-end (AFE) is used with an antenna for power and communication. Features of the serial peripheral interface (SPI) include power management, a clock, memory, an energy harvester battery connection.
Figure 6:
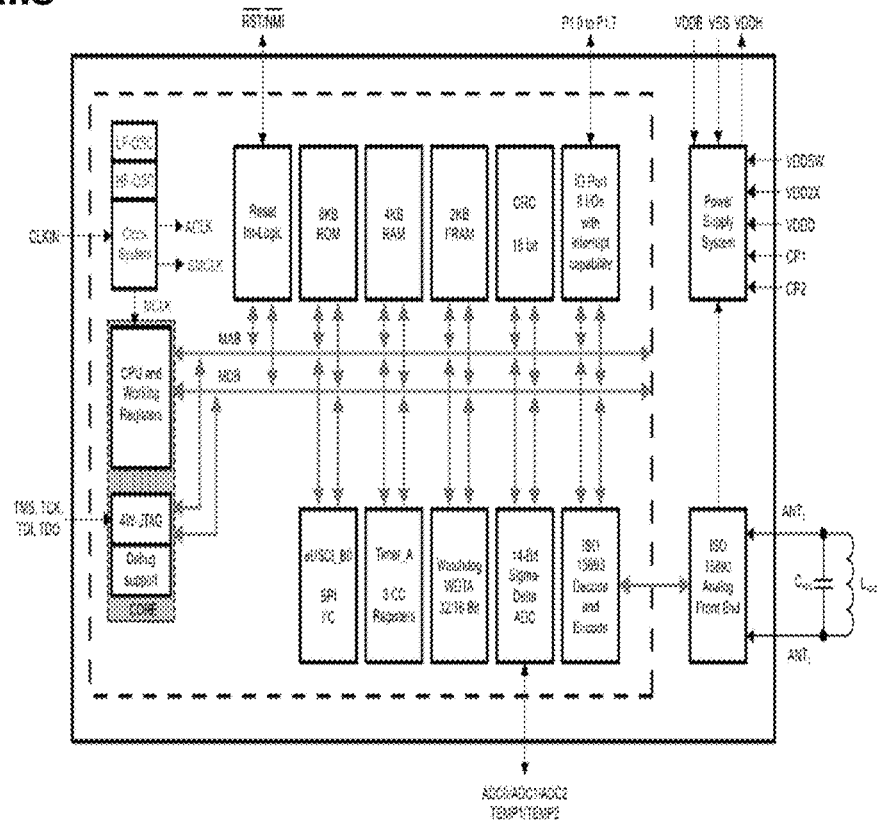
FIG. 6. Schematic of NFC chip layout for a RF430FRL152H NFC chip. Compatible with single, two and three channel NFC dosimeter designs with a reset feature. Includes three external ADC channels and an internal ADC channel used by an internal temperature sensor. An AFE is used with an antenna for power and communication. Features of the SPI include power management, an energy harvester battery connection, 7 I/O ports, a clock, memory, and a CPU.
Figure 7:
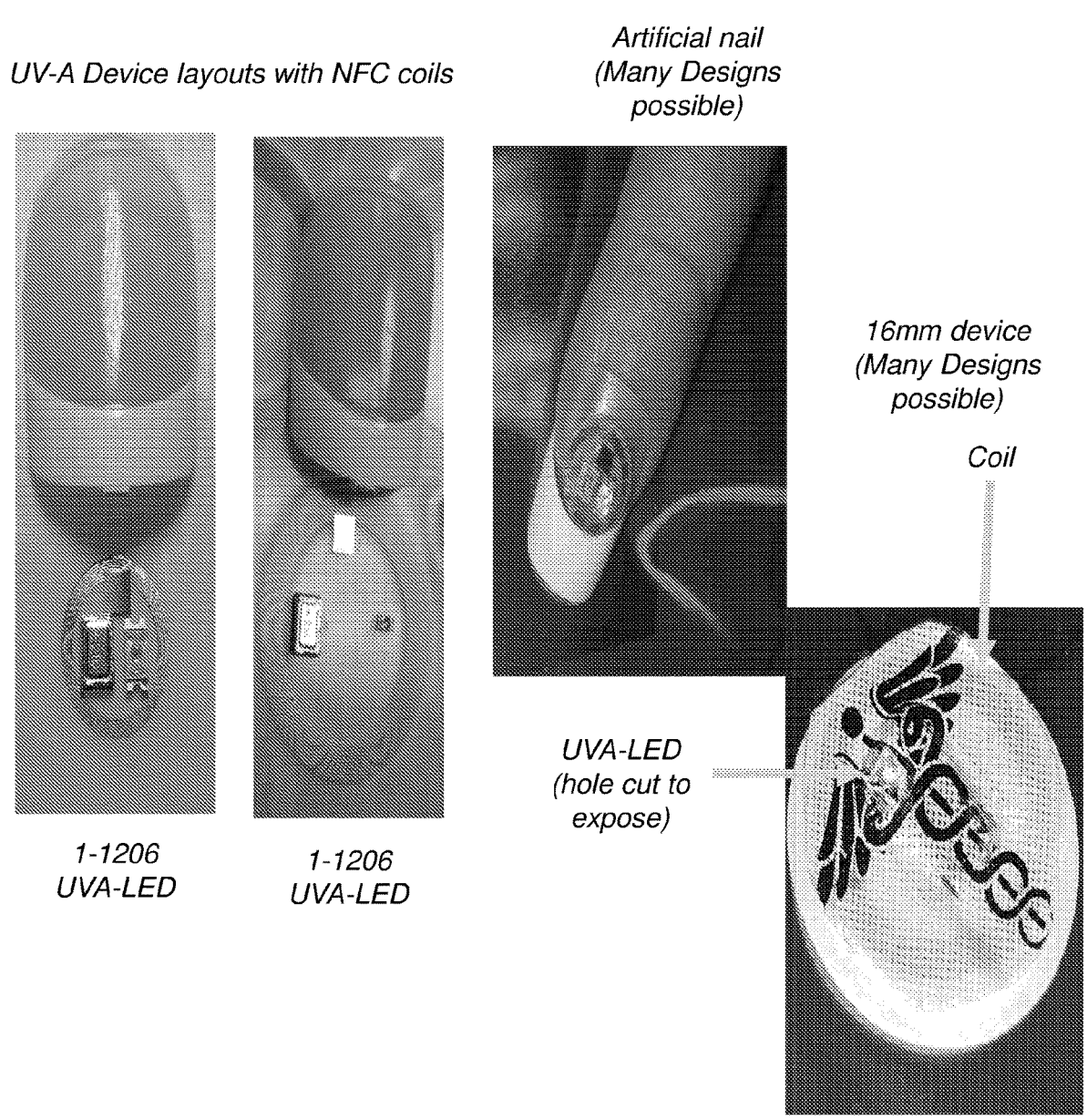
FIG. 7. Pictures of UV dosimeters and corresponding completed functional faux fingernail mounted devices with and without design overlays.
Figure 8:
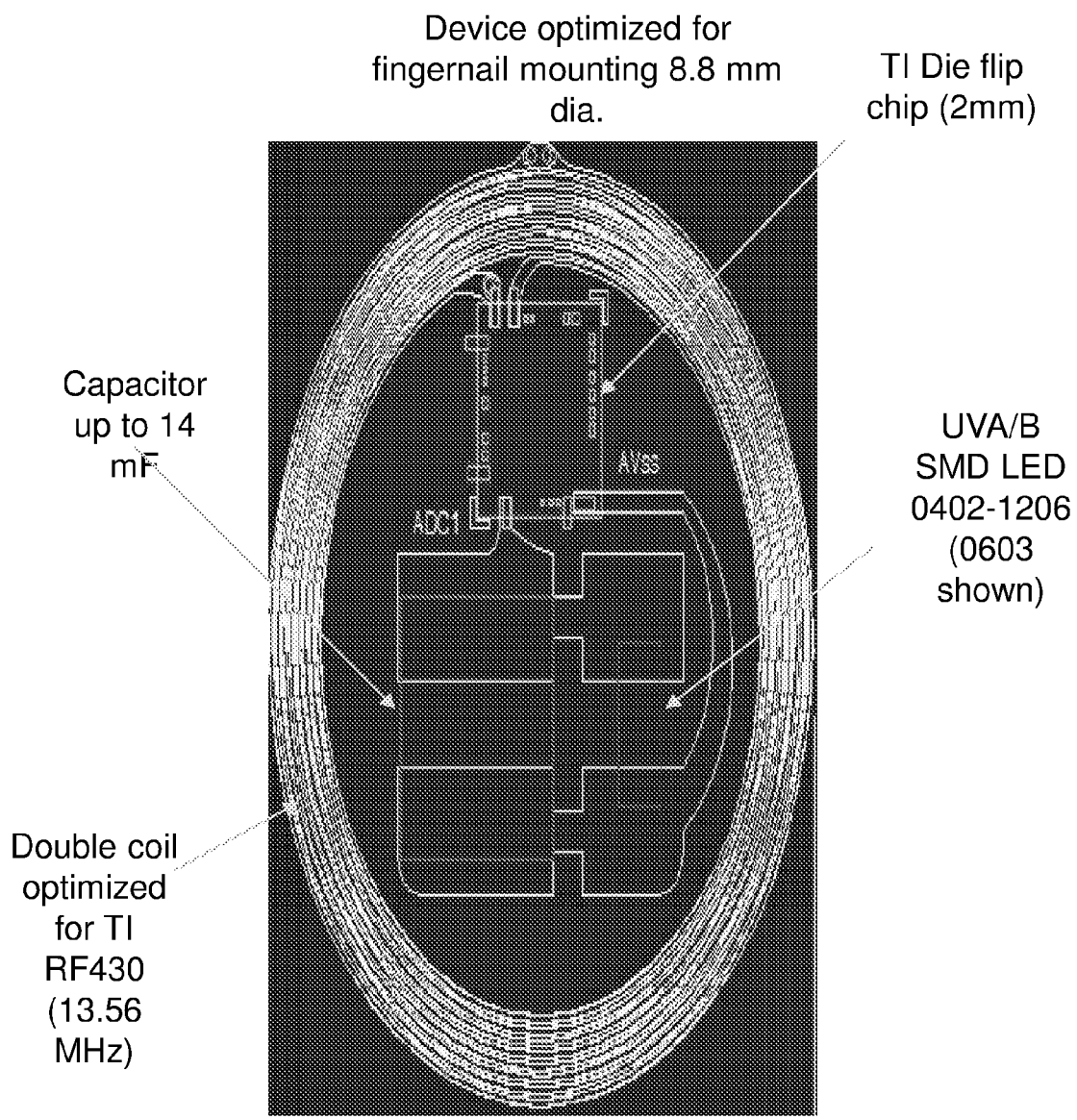
FIG. 8. Schematic circuit layout design for single channel ADC UV dosimeter NFC device.
Figure 9:
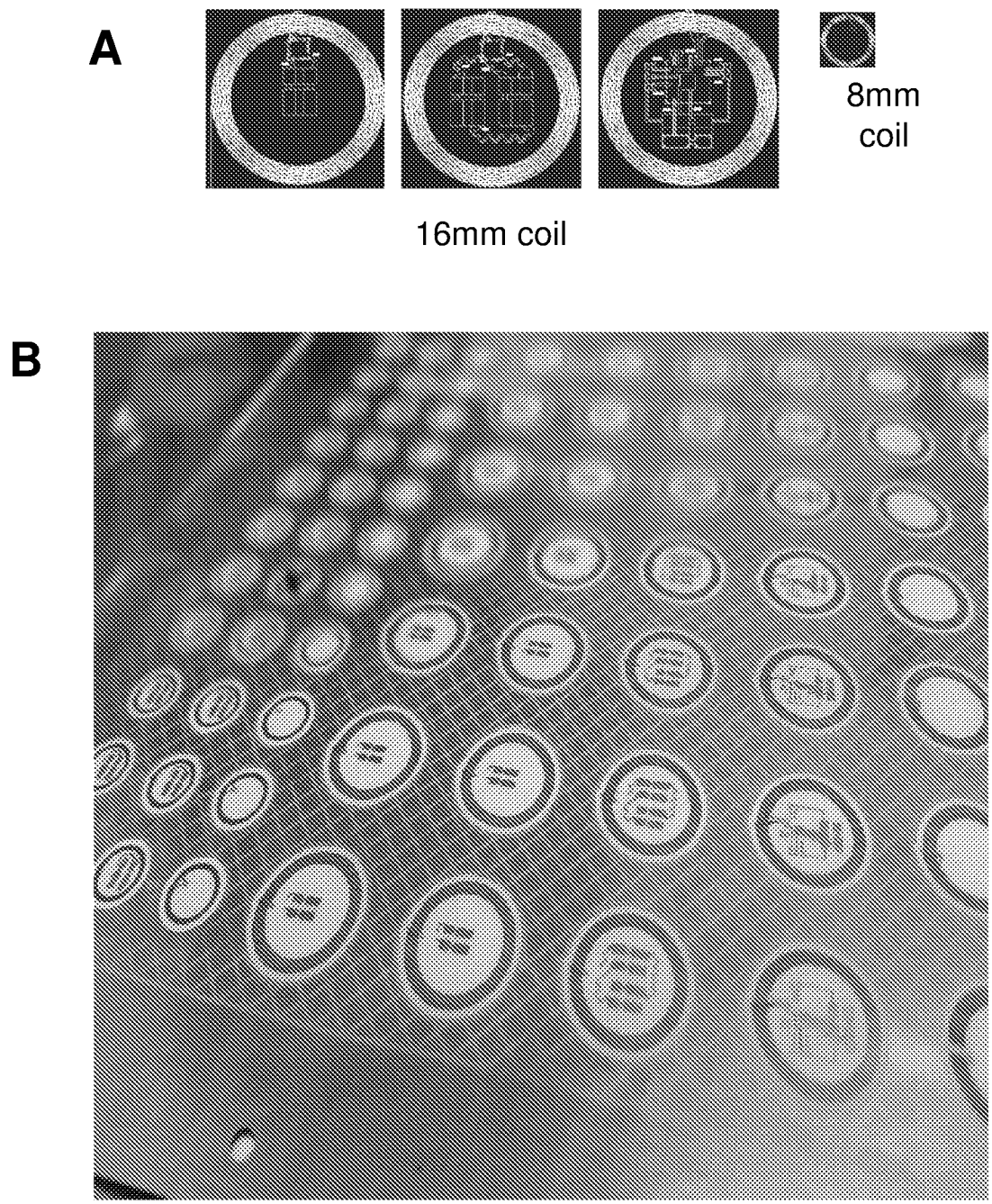
FIG. 9. A) Three separate UV dosimeter designs and schematics with varying functionality. B) Mass manufactured circuits of all three designs prior to component attachment.
Figure 10:
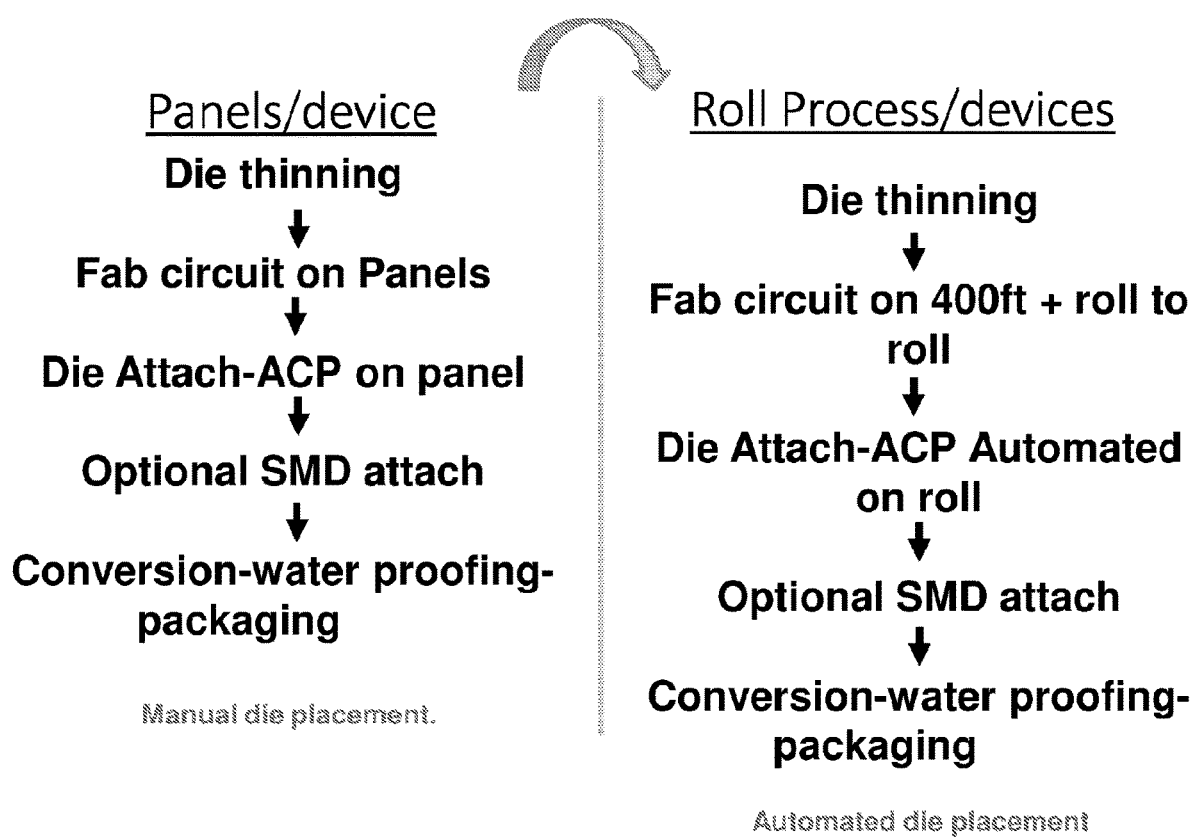
FIG. 10. Manufacturing process flow for UV dosimeter devices both in panel and roll productions modes. A NFC wafer is thinned, if necessary, by a back grinding process then diced into individual die, or WL-CSP. Circuits are fabricated with a dielectric layer and copper metal by either additive or etch back manufacturing processes. Die are attached to fabricated flex circuit using a flip-chip bonding with anisotropic conductive paste (ACP) hybrid materials and/or solder with WL-CSP. Followed by additional SMT/SMD component attachment. Completed circuits are then encapsulated, cut from panel/roll, packaged and adhesive applied.
Figure 13:
FIG. 13. Functional UV dosimeter devices in various forms and embodiments.
Figure 14:
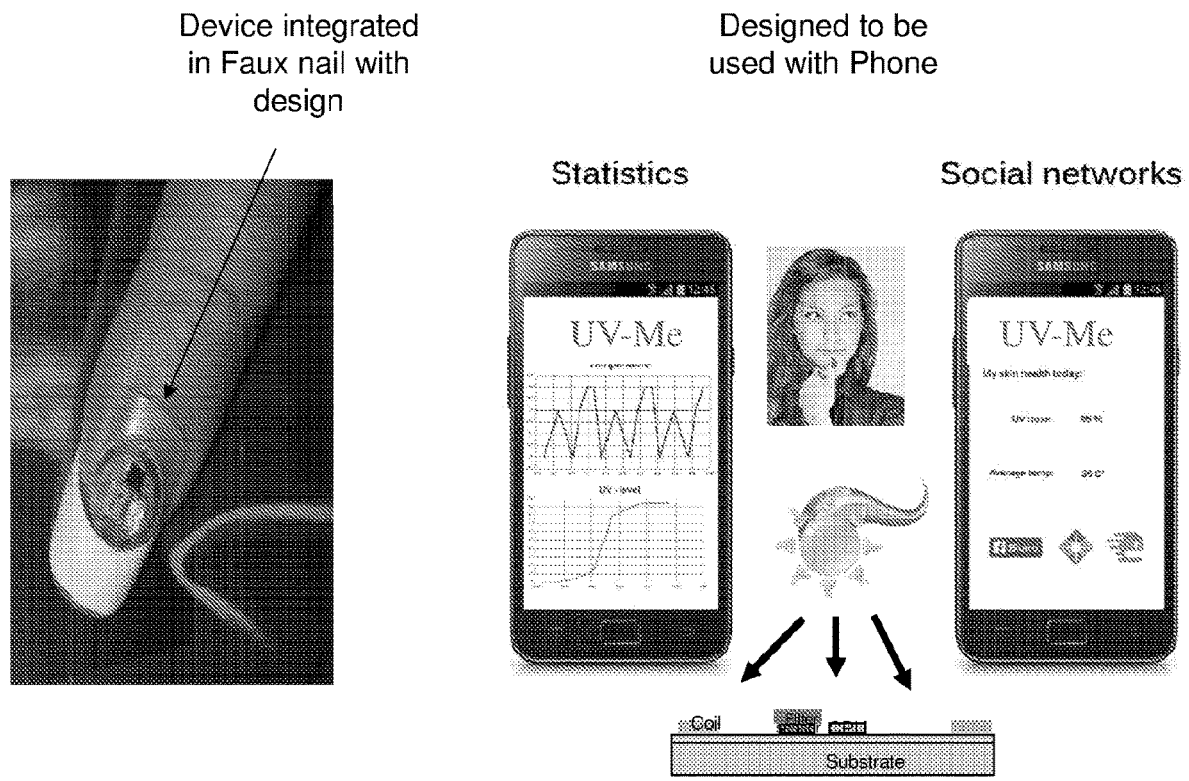
FIG. 14. UV dosimeter NFC device with faux fingernail packaging, examples of UV dosimeter software on mobile devices, and cross section of a monitoring system comprising a substrate, NFC coil, a sensor under a filter and a CPU.
Figure 15:
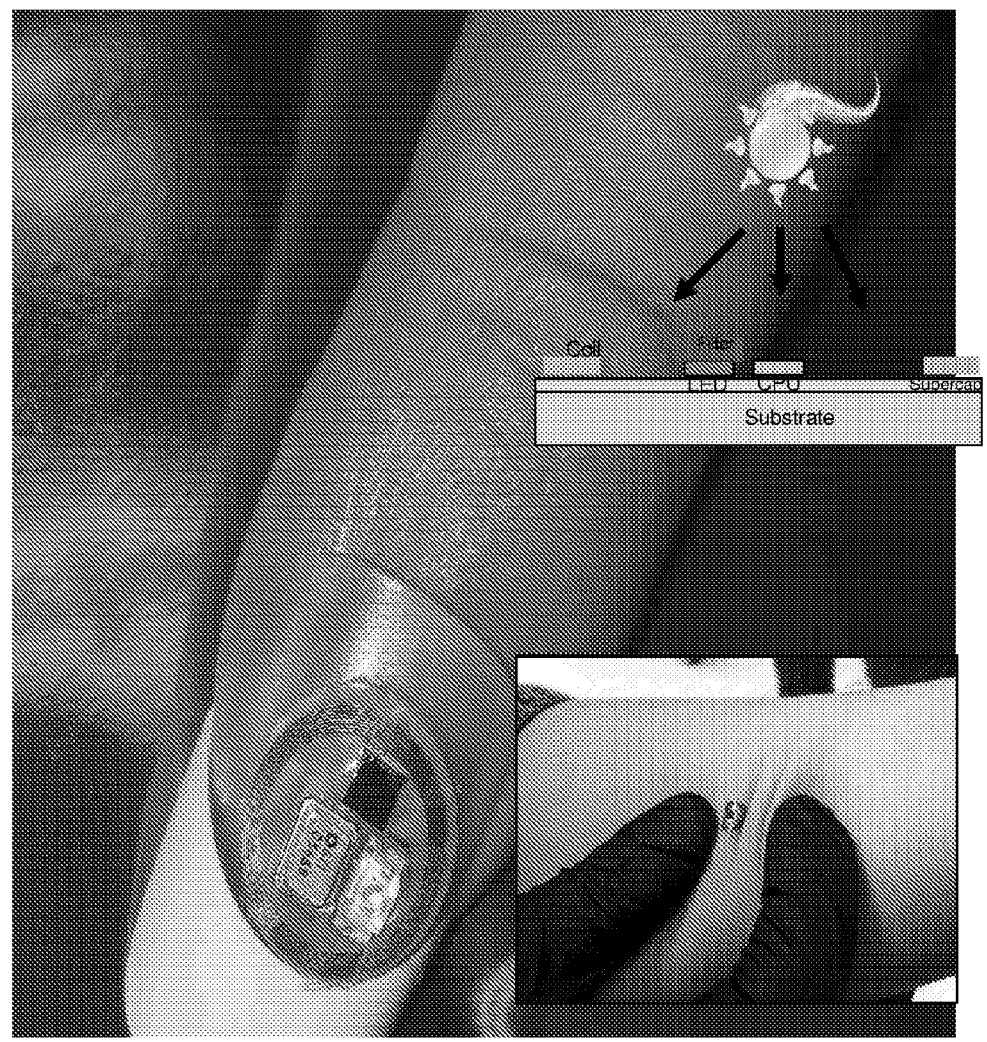
FIG. 15. Example of UV fingernail dosimeter device without additional packaging and a UV dosimeter NFC device mounted on skin, demonstrating the conformability of the miniature embodiment.
Figure 16:
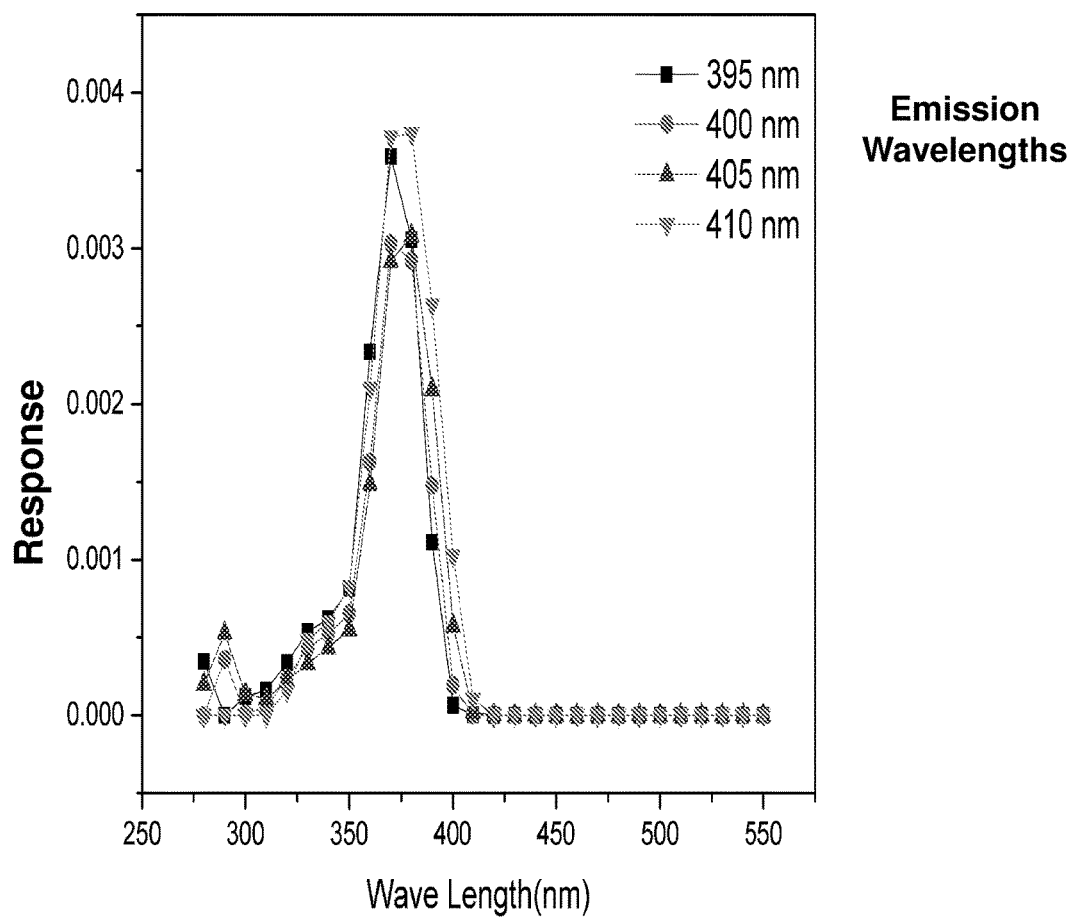
FIG. 16. Spectral absorption responses for various UV LEDs with stated emission wavelengths obtained by commercial EQE External quantum efficiency measurement equipment. The measurement indicates all LEDs tested here are suitable to be used as low cost photodetectors in the UVA range.
Figure 17:
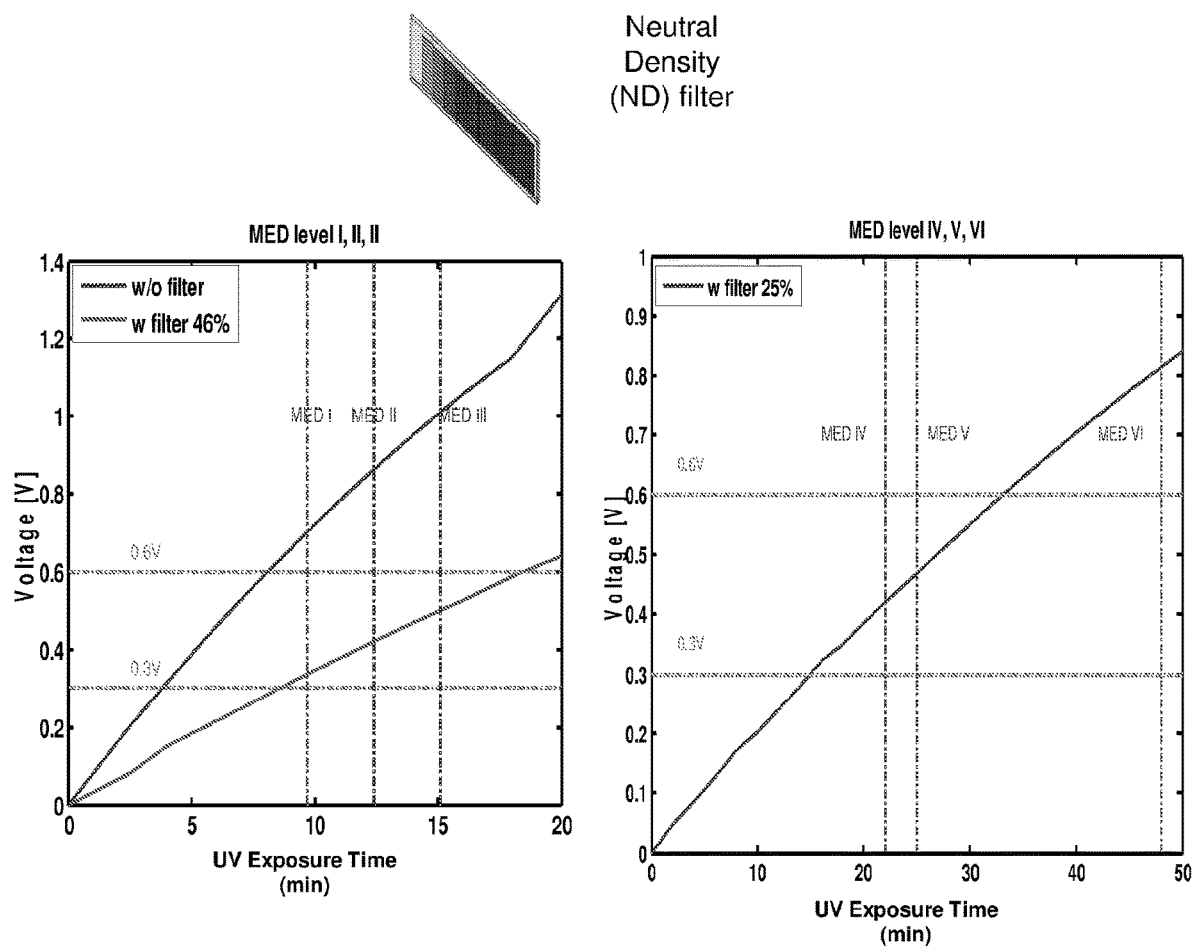
FIG. 17. Plot of the charge value of the capacitor in a single channel UVA dosimeter device as a function of UVA radiation. The test was performed using a commercial solar simulator as the UV source. UVA levels were measured using certified UV measurement devices. The MED values were obtained from Fitzpatrick, T. B. (1988) Arch. Dermatol. 124(6). (See, FIG. 20.) Readings from the NFC dosimeter were obtained wirelessly.
Figure 18:
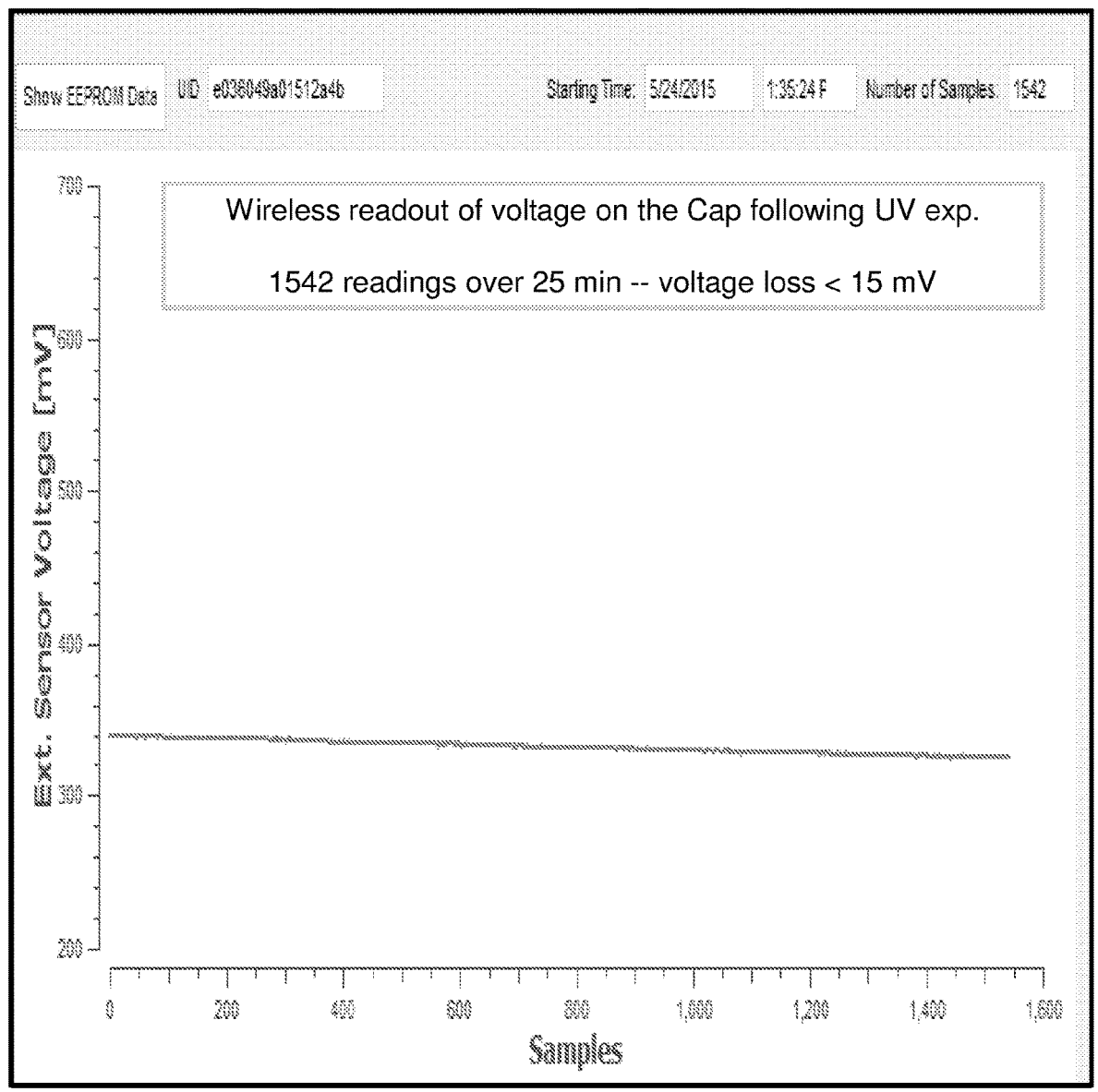
FIG. 18. Experimental result of a UV dosimeter being read wirelessly. 1542 readings were obtained over 25 min with a voltage loss <15 mV. This result indicates that wirelessly reading the voltage of the correlating UV dose has minimal effect on the overall accuracy related to discharge due to data acquisition. After 1542 readings over 25 minutes the percent charge loss was less than 5%.
Figure 23:
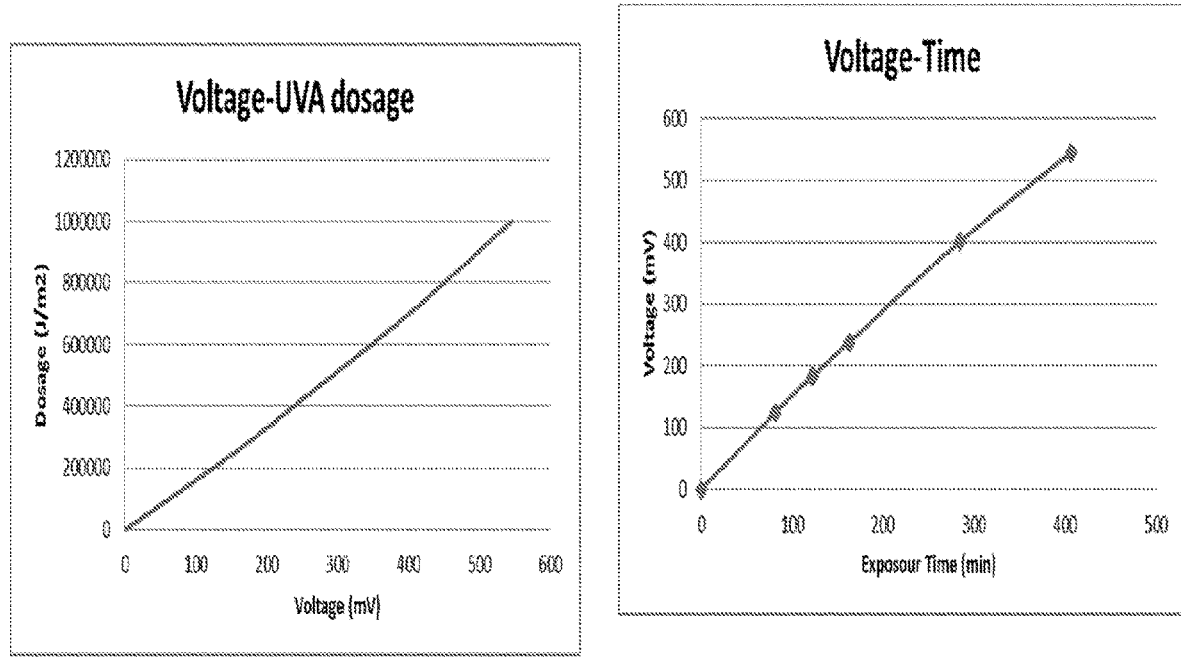
FIG. 23. Experimental calibration of UV dosimeter device from NFC voltage response to UV dose. Plot of the charge value of the capacitor from one channel of a two channel dosimeter device as a function of UVA radiation on one of the channels. The test was performed using a commercial solar simulator as the UVA source. UVA levels were measured using certified UV measurement devices. The MED values were obtained from Fitzpatrick, T. B. (1988) Arch. Dermatol. 124(6). (See, FIG. 20.) Readings from the NFC dosimeter were obtained wirelessly.
Figure 24:
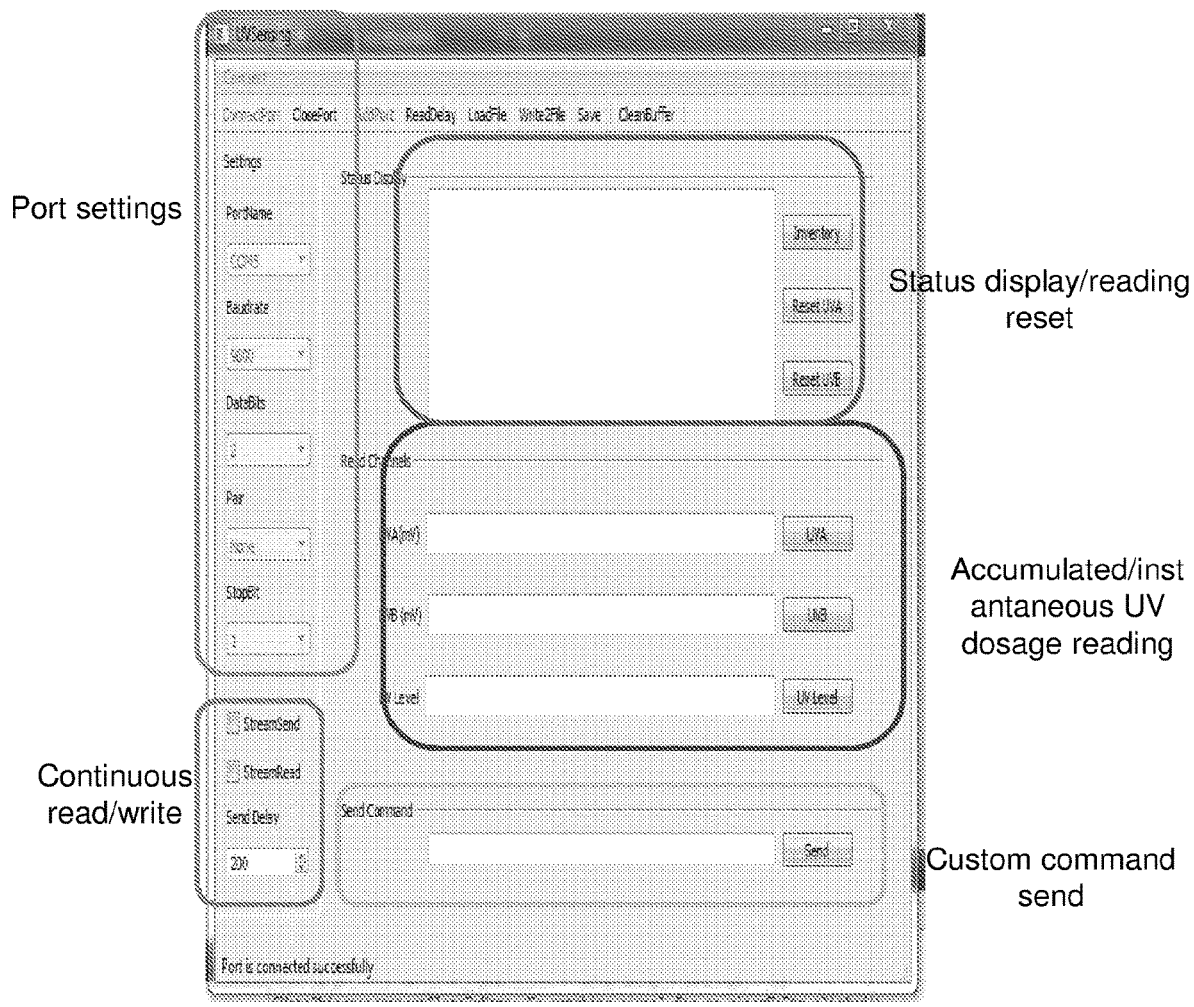
FIG. 24. Screen shot of custom Gui app written for interfacing UV dosimeter NFC device.
Figure 26:
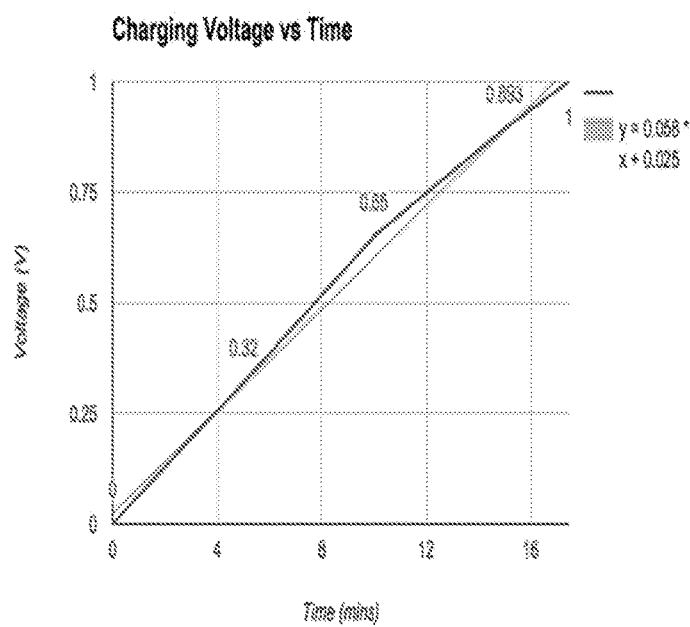
FIG. 26. Experimental testing of charging times of a capacitor with a value of 330 µF compared to FIG. 25 using a 14 mF capacitor. In both cases, the charge was supplied by the same UVB LED/PD illuminated from a UVB source with an intensity 0.5 W/m$^2$.
Figure 27:
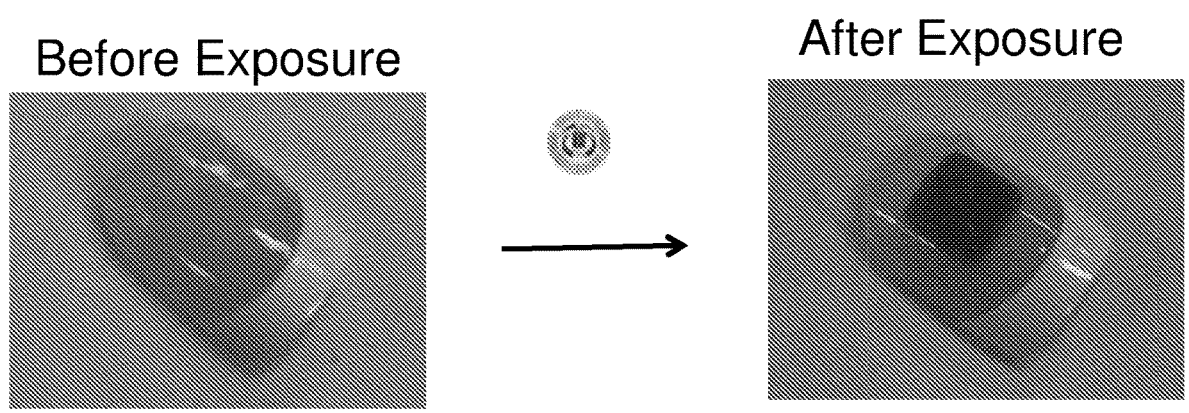
FIG. 27. Colorimetric mounted UV sensor in combination with a digital UV dosimeter utilizing NFC.
Figure 30:
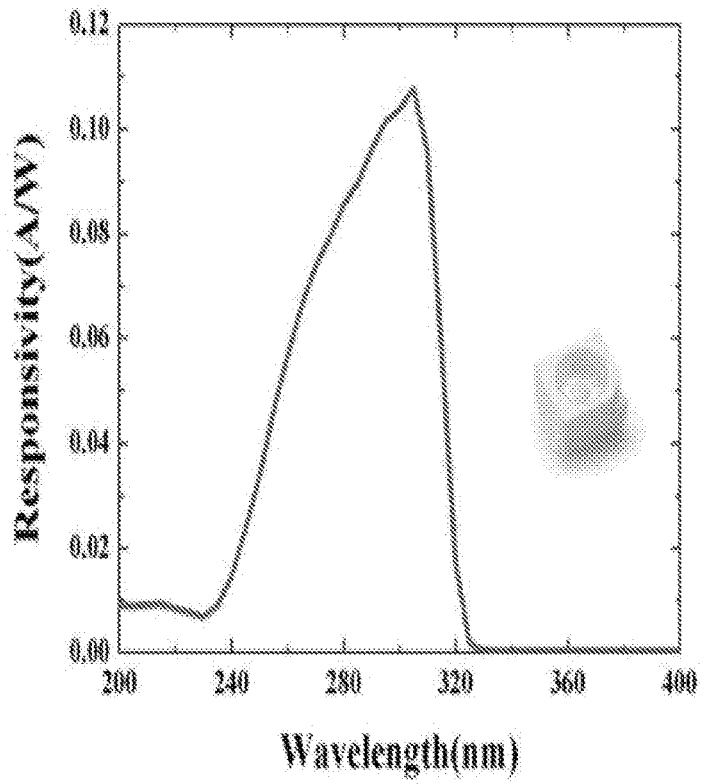
FIG. 30. Example of a UVB LED that can be used as a sensor.
Figure 31:
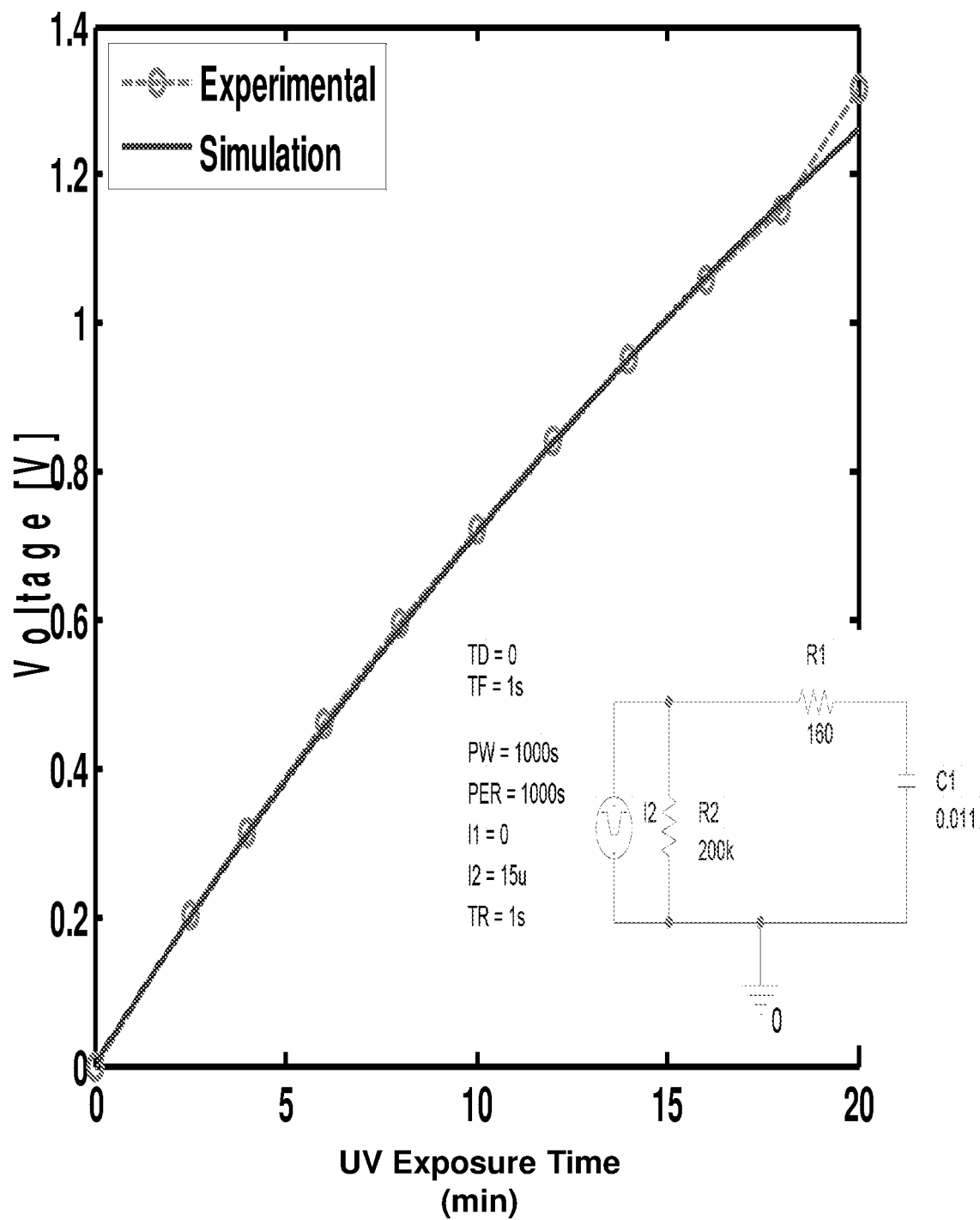
FIG. 31. Plot of experimental results and corresponding equivalent simulation using the circuit shown. The experimental results were obtained using a solar simulator and a single channel from a NFC UV dosimeter device.
Figure 32:
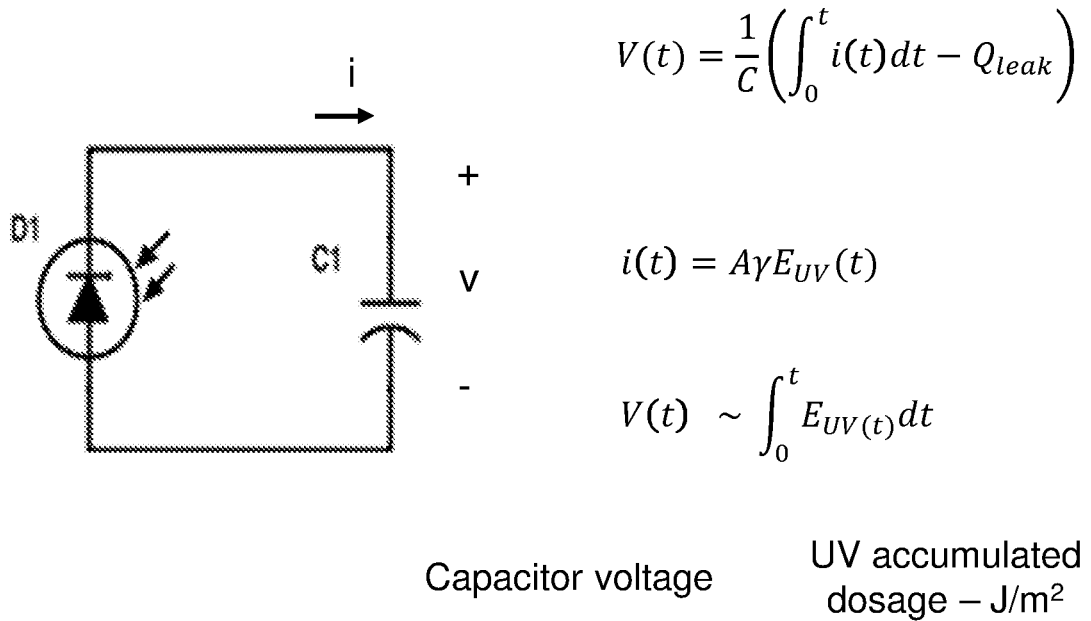
FIG. 32. Model and corresponding proofs for accumulated UVA and UVB responses with related UV dosimeter NFC devices.
Figure 34:
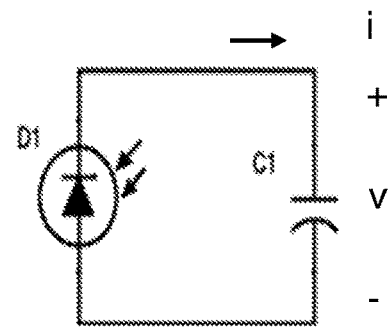
FIG. 34. Instantaneous dose model and equations for UV dosimeter UV intensity measurements.
Figure 35:
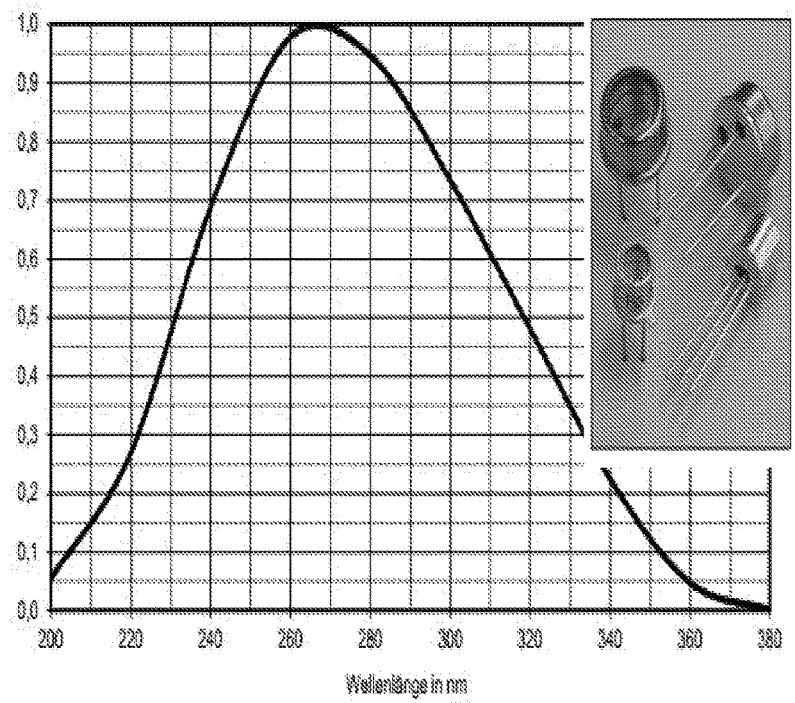
FIG. 35. UVB calibration using stated UVB photo sensor.
Figure 37:
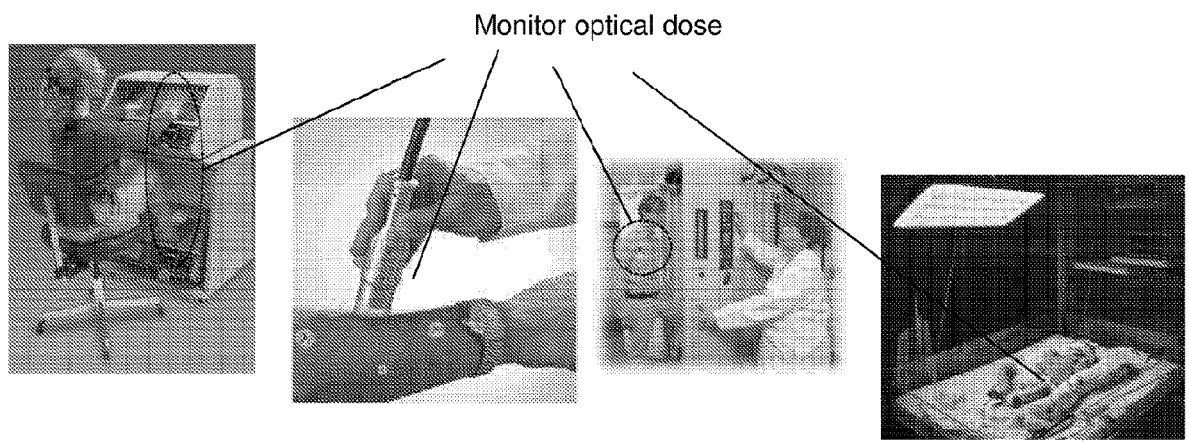
FIG. 37. Examples of UV NFC dosimeter devices used for clinical and hospital applications.

In general, the terms and phrases used herein have their art-recognized meaning, which can be found by reference to standard texts, journal references and contexts known to those skilled in the art. The following definitions are provided to clarify their specific use in the context of the invention.

"Ambient parameter" refers to a condition, state or property experienced by a monitoring system, such as an environmental condition, state or property. In an embodiment, for example, the ambient parameter is capable of being detected, monitored and/or converted into an electric signal. Exemplary ambient parameters include but are not limited to incident electromagnetic radiation, nuclear radiation, temperature, incident ionizing radiation, heat, movement (e.g., acceleration), strain, pollution (gaseous, liquid and particulate), sound (acoustic waves) and magnetic forces.

As used herein, the term "measurement" refers to generation of a signal indicative of an ambient parameter. "Readout" refers to transfer or transmission of the measured signal, or a signal derived from the measured signal, for example to an external device such as a computer or mobile device. In an embodiment of the present invention, the measurement and readout functions of a monitoring system are independently powered.

The terms "flexible" and "bendable" are used synonymously in the present description and refer to the ability of a material, structure, device or device component to be deformed into a curved or bent shape without undergoing a transformation that introduces significant strain, such as strain characterizing the failure point of a material, structure, device or device component. In an exemplary embodiment, a flexible material, structure, device or device component may be deformed into a curved shape without introducing strain larger than or equal to 5%, for some applications larger than or equal to 1%, and for yet other applications larger than or equal to 0.5% in strain-sensitive regions. A used herein, some, but not necessarily all, flexible structures are also stretchable. A variety of properties provide flexible structures (e.g., device components) of the invention, including materials properties such as a low modulus, bending stiffness and flexural rigidity; physical dimensions such as small average thickness (e.g., less than 100 microns, optionally less than 10 microns and optionally less than 1 micron) and device geometries such as thin film and mesh geometries.

The term "tissue" is used broadly to describe any types of material of which animals or plants are made, for example, consisting of specialized cells and their products. A used herein tissue may refer to cells corresponding to one or more organs, such as cells that substantially carry out the same or complementary functions. Tissue as referred to herein may correspond to animals, including human and non-human animals (e.g., livestock, veterinary animals, etc), and plants. Tissue as referred to herein may correspond to living cells or dead cells which may include, but are not limited to, the corpus *unguis*, (e.g., fingernail, toenail, claw hoof, horn etc.). Examples of tissues include skin, a fingernail, toenail, tooth, bone or an ear lobe.

"Stretchable" refers to the ability of a material, structure, device or device component to be strained without undergoing fracture. In an exemplary embodiment, a stretchable material, structure, device or device component may undergo strain larger than 0.5% without fracturing, for some applications strain larger than 1% without fracturing and for yet other applications strain larger than 3% without fracturing. As used herein, many stretchable structures are also flexible. Some stretchable structures (e.g., device components) are engineered to be able to undergo compression, elongation and/or twisting so as to be able to deform without fracturing. Stretchable structures include thin film structures comprising stretchable materials, such as elastomers; bent structures capable of elongation, compression and/or twisting motion; and structures having an island-bridge geometry. Stretchable device components include structures having stretchable interconnects, such as stretchable electrical interconnects.

"Functional layer" refers to a device-containing layer that imparts some functionality to the device. For example, the functional layer may be a thin film such as a semiconductor layer. Alternatively, the functional layer may comprise multiple layers, such as multiple semiconductor layers separated by support layers. The functional layer may comprise a plurality of patterned elements, such as interconnects running between device-receiving pads or islands. The functional layer may be heterogeneous or may have one or more properties that are inhomogeneous. "Inhomogeneous property" refers to a physical parameter that can spatially vary.

"Semiconductor" refers to any material that is an insulator at a low temperature, but which has an appreciable electrical conductivity at temperatures of approximately 300 Kelvin. In the present description, use of the term semiconductor is intended to be consistent with use of this term in the art of microelectronics and electronic devices. Useful semiconductors include those comprising element semiconductors, such as silicon, germanium and diamond, and compound semiconductors, such as group IV compound semiconductors such as SiC and SiGe, group III-V semiconductors such as AlSb, AlAs, Aln, AlP, BN, GaSb, GaAs, GaN, GaP, InSb, InAs, InN, and InP, group III-V ternary semiconductor alloys such as $Al_xGa_{1-x}As$, group II-VI semiconductors such as CsSe, CdS, CdTe, ZnO, ZnSe, ZnS, and ZnTe, group I-VII semiconductors such as CuCl, group IV-VI semiconductors such as PbS, PbTe and SnS, layer semiconductors such as $PbI_2$, $MoS_2$ and GaSe, oxide semiconductors such as CuO and $Cu_2O$. The term semiconductor includes intrinsic semiconductors and extrinsic semiconductors that are doped with one or more selected materials, including semiconductors having p-type doping materials and n-type doping materials, to provide beneficial electronic properties useful for a given application or device. The term semiconductor includes composite materials comprising a mixture of semiconductors and/or dopants. Specific semiconductor materials useful for some embodiments include, but are not limited to, Si, Ge, SiC, AlP, AlAs, AlSb, GaN, GaP, GaAs, GaSb, InP, InAs, GaSb, InP, InAs, InSb, ZnO, ZnSe, ZnTe, CdS, CdSe, ZnSe, ZnTe, CdS, CdSe, CdTe, HgS, PbS, PbSe, PbTe, AlGaAs, AlInAs, AlInP, GaAsP, GaInAs, GaInP, AlGaAsSb, AlGaInP and GaInAsP. Porous silicon semiconductor materials are useful for applications of aspects described herein in the field of sensors and light emitting materials, such as light emitting diodes (LEDs) and solid state lasers. Impurities of semiconductor materials are atoms, elements, ions and/or molecules other than the semiconductor material(s) themselves or any dopants provided to the semiconductor material. Impurities are undesirable materials present in semiconductor materials, which may negatively impact the electronic properties of semiconductor materials, and include but are not limited to oxygen, carbon, and metals including heavy metals. Heavy metal impurities include, but are not limited to, the group of elements between copper and lead on the periodic table, calcium, sodium, and all ions, compounds and/or complexes thereof.

"Coincident" refers to the relative position of two or more objects, planes or surfaces, for example a surface such as a neutral mechanical surface (NMS) or neutral mechanical plane (NMP) that is positioned within or is adjacent to a layer, such as a functional layer, substrate layer, or other layer. In an embodiment, a NMS or NMP is positioned to correspond to the most strain-sensitive layer or material within the layer. "Proximate" refers to the relative position of two or more objects, planes or surfaces, for example a NMS or NMP that closely follows the position of a layer, such as a functional layer, substrate layer, or other layer while still providing desired flexibility or stretchability without an adverse impact on the strain-sensitive material physical properties. In general, a layer having a high strain sensitivity, and consequently being prone to being the first layer to fracture, is located in the functional layer, such as a functional layer containing a relatively brittle semiconductor or other strain-sensitive device element. A NMS or NMP that is proximate to a layer need not be constrained within that layer, but may be positioned proximate or sufficiently near to provide a functional benefit of reducing the strain on the strain-sensitive device element when the device is folded.

In this aspect, "strain-sensitive" refers to a material that fractures or is otherwise impaired in response to a relatively low level of strain. In an aspect, the NMS is coincident or proximate to a functional layer. In an aspect, the NMS is coincident to a functional layer, referring to at least a portion of the NMS being located within the functional layer that contains a strain-sensitive material for all lateral locations along the NMS. In an aspect, the NMS is proximate to a functional layer, wherein although the NMS may not be coincident with the functional layer, the position of the NMS provides a mechanical benefit to the functional layer, such as substantially lowering the strain that would otherwise be exerted on the functional layer but for the position of the NMS. For example, the position of a proximate NMS is optionally defined as the distance from the strain-sensitive material that provides an at least 10%, 20%, 50% or 75% reduction in strain in the strain-sensitive material for a given folded configuration, such as a device being folded so that the radius of curvature is on the order of the millimeter or centimeter scale. In another aspect, the position of a proximate NMS can be defined in absolute terms such as a distance from the strain-sensitive material, such as less than several mm, less than 2 mm, less than 10 µm, less than 1 µm, or less than 100 nm. In another aspect, the position of a proximate layer is defined relative to the layer that is adjacent to the strain-sensitive material, such as within 50%, 25% or 10% of the layer closest to the strain-sensitive-containing layer. In an aspect, the proximate NMS is contained within a layer that is adjacent to the functional layer.

A "component" is used broadly to refer to an individual part of a device.

"Sensing" refers to detecting the presence, absence, amount, magnitude or intensity of a physical and/or chemical property. Useful device components for sensing include, but are not limited to electrode elements, chemical or biological sensor elements, pH sensors, temperature sensors, strain sensors, mechanical sensors, position sensors, optical sensors and capacitive sensors.

"Actuating" refers to stimulating, controlling, or otherwise affecting a structure, material or device component. Useful device components for actuating include, but are not limited to, electrode elements, electromagnetic radiation emitting elements, light emitting diodes, lasers, magnetic elements, acoustic elements, piezoelectric elements, chemical elements, biological elements, and heating elements.

The terms "directly and indirectly" describe the actions or physical positions of one component relative to another component. For example, a component that "directly" acts upon or touches another component does so without intervention from an intermediary. Contrarily, a component that "indirectly" acts upon or touches another component does so through an intermediary (e.g., a third component).

"Encapsulate" refers to the orientation of one structure such that it is at least partially, and in some cases completely, surrounded by one or more other structures, such as a substrate, adhesive layer or encapsulating layer. "Partially encapsulated" refers to the orientation of one structure such that it is partially surrounded by one or more other structures, for example, wherein 30%, or optionally 50%, or optionally 90% of the external surface of the structure is surrounded by one or more structures. "Completely encapsulated" refers to the orientation of one structure such that it is completely surrounded by one or more other structures.

"Dielectric" refers to a non-conducting or insulating material.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are particularly useful for some applications. Polymers useable in the methods, devices and components include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

"Elastomer" refers to a polymeric material which can be stretched or deformed and returned to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers include, but are not limited to, thermoplastic elastomers, styrenic materials, olefinic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. Exemplary elastomers include, but are not limited to silicon containing polymers such as polysiloxanes including poly(dimethyl siloxane) (i.e. PDMS and h-PDMS), poly(methyl siloxane), partially alkylated poly (methyl siloxane), poly(alkyl methyl siloxane) and poly (phenyl methyl siloxane), silicon modified elastomers, thermoplastic elastomers, styrenic materials, olefinic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a polymer is an elastomer.

"Conformable" refers to a device, material or substrate which has a bending stiffness that is sufficiently low to allow the device, material or substrate to adopt a contour profile desired for a specific application, for example a contour profile allowing for conformal contact with a surface having a non-planar geometry such as a surface with relief features or a dynamic surface (e.g. changes with respect to time). In certain embodiments, a desired contour profile is that of a fingernail, toenail, skin, tooth or ear lobe.

"Conformal contact" refers to contact established between a device and a receiving surface. In one aspect, conformal contact involves a macroscopic adaptation of one or more surfaces (e.g., contact surfaces) of a device to the overall shape of a surface. In another aspect, conformal contact involves a microscopic adaptation of one or more surfaces (e.g., contact surfaces) of a device to a surface resulting in an intimate contact substantially free of voids. In an embodiment, conformal contact involves adaptation of a contact surface(s) of the device to a receiving surface(s) such that intimate contact is achieved, for example, wherein less than 20% of the surface area of a contact surface of the device does not physically contact the receiving surface, or optionally less than 10% of a contact surface of the device does not physically contact the receiving surface, or optionally less than 5% of a contact surface of the device does not physically contact the receiving surface.

"Young's modulus" or "modulus" are used interchangeably and refer to a mechanical property of a material, device or layer which refers to the ratio of stress to strain for a given substance. Young's modulus may be provided by the expression:

$$E = \frac{(\text{stress})}{(\text{strain})} = \left(\frac{L_0}{\Delta L}\right)\left(\frac{F}{A}\right), \quad (I)$$

where E is Young's modulus, $L_0$ is the equilibrium length, $\Delta L$ is the length change under the applied stress, F is the force applied, and A is the area over which the force is applied. Young's modulus may also be expressed in terms of Lame constants via the equation:

$$E = \frac{\mu(3\lambda + 2\mu)}{\lambda + \mu}, \quad (II)$$

where $\lambda$ and $\mu$ are Lame constants. High Young's modulus (or "high modulus") and low Young's modulus (or "low modulus") are relative descriptors of the magnitude of Young's modulus in a given material, layer or device. In some embodiments, a high Young's modulus is larger than a low Young's modulus, preferably about 10 times larger for some applications, more preferably about 100 times larger for other applications, and even more preferably about 1000 times larger for yet other applications. In an embodiment, a low modulus layer has a Young's modulus less than 100 MPa, optionally less than 10 MPa, and optionally a Young's modulus selected from the range of 0.1 MPa to 50 MPa. In an embodiment, a high modulus layer has a Young's modulus greater than 100 MPa, optionally greater than 10 GPa, and optionally a Young's modulus selected from the range of 1 GPa to 100 GPa. In an embodiment, a device of the invention has one or more components having a low Young's modulus. In an embodiment, a device of the invention has an overall low Young's modulus.

"Low modulus" refers to materials having a Young's modulus less than or equal to 10 MPa, less than or equal to 20 MPa or less than or equal to 1 MPa.

"Bending stiffness" is a mechanical property of a material, device or layer describing the resistance of the material, device or layer to an applied bending movement. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

"Lateral dimensions" refer to physical dimensions of a structure such as a tissue mounted electronic system or component thereof. For example, lateral dimensions may refer to one or more physical dimensions oriented orthogonal to axes extending along the thickness of a structure, such as the length, the width, the radius or the diameter of the structure. Lateral dimensions are useful for characterizing the area of an electronic system or component thereof, such as characterizing the lateral area footprint of a system corresponding to a two dimensional area in a plane or surface positioned orthogonal to axes extending along the thickness of the structure.

Example 1: Tissue-Mounted NFC Device for UV Sensing

The invention provides, for example, miniature tissue-mounted near field communication (NFC) devices providing a platform for UV exposure monitoring. The materials, design, and circuit integration enable biocompatible NFC technology. In some embodiments, the NFC technology offers individual users, dermatologists, farmers, researchers, and/or merchants a way to measure UV exposure times and doses. The NFC devices of this example are placed either on skin, a fingernail, a plant stem, and/or a leaf. The devices are able to wirelessly communicate with readers that use NFC antennas.

In some embodiments, for privacy, some versions of the invention have a devoted chip that stores an encrypted identification number that is unique to each individual device. In addition, the chip may have action-specific security codes that change constantly. In some embodiments, the encrypted device number helps keep the digital information private.

In some embodiments, devices are waterproof and remain operational for several days or months. The system of this aspect of the invention is able to work in conjunction with computer or mobile applications. In some embodiments, if removed from the tissue, the device is permanently disabled and all private information is destroyed.

Example 2: Skin or Nail Mounted Sensors of Exposure to UV Phototherapy

Skin or nail plate mounted, thin, miniature UV radiation sensors continuously monitor exposure to UV and/or low range visible radiation. Applications include total dose under bilirubin lights, patients receiving various other light therapy in treatment of skin disorders such as with psoriasis, vitiligo, scleroderma, morphea and cutaneous graft-versus-host disease (GVHD).

Example 3: Pulse Oximetry on Skin or Fingernails

Current oximetry devices are bulky, often cable-bound, devices. This makes the devices hard to wear over a long period and also makes continuous monitoring difficult. Furthermore, due to the higher mass and attached cable motion artifacts are introduced into a signal, which are detrimental to accuracy of the devices.

Figure 39:
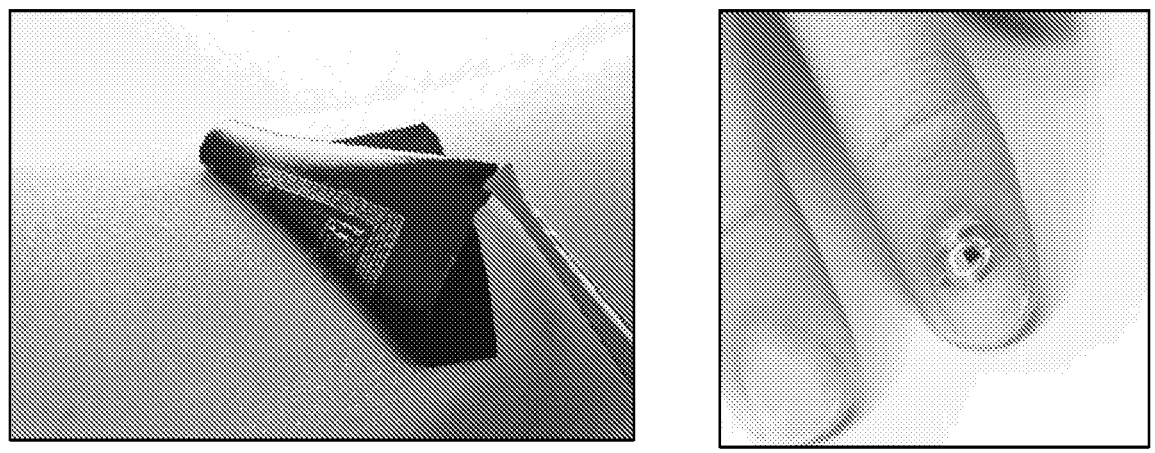
FIG. 39. Pulse oximetry devices on tissue and fingernails.
Figure 40:
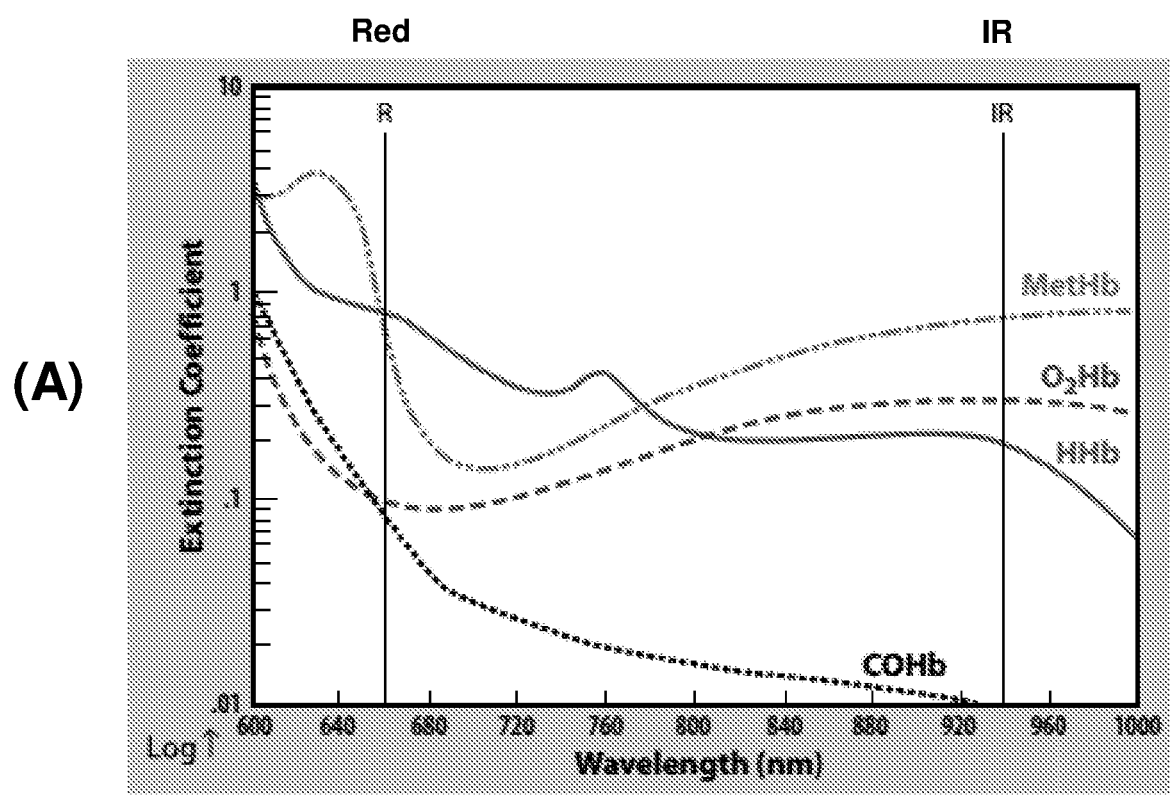
FIG. 40. Schematics showing (A) a graphical representation of extinction coefficient versus wavelength for oxygenated ($O_2Hb$) and deoxygenated (HHb) hemoglobin, (B) layouts for fingernail mounted devices and (C) adsorption as a function of current and time throughout a tissue depth.
Figure 41:
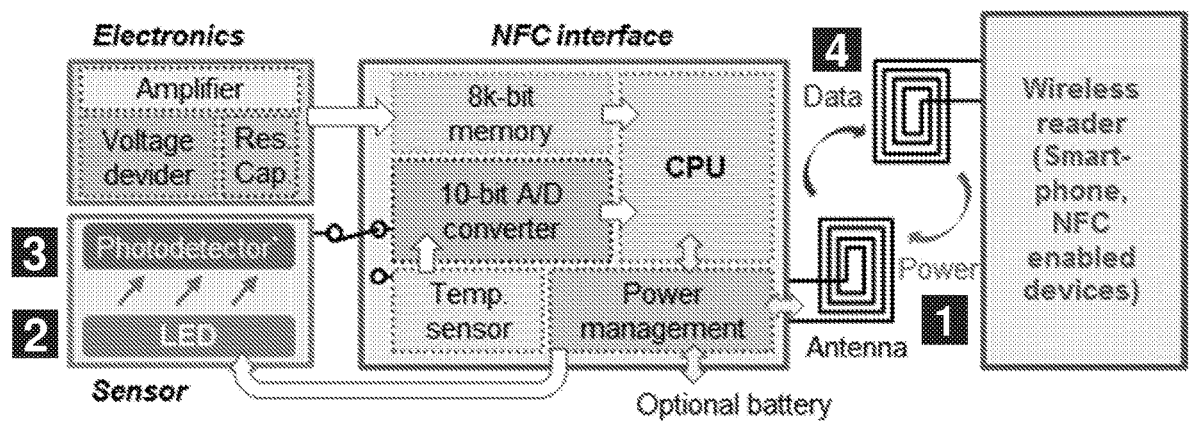
FIG. 41. Schematic of battery-less, miniaturized oximetry devices.
Figure 43:
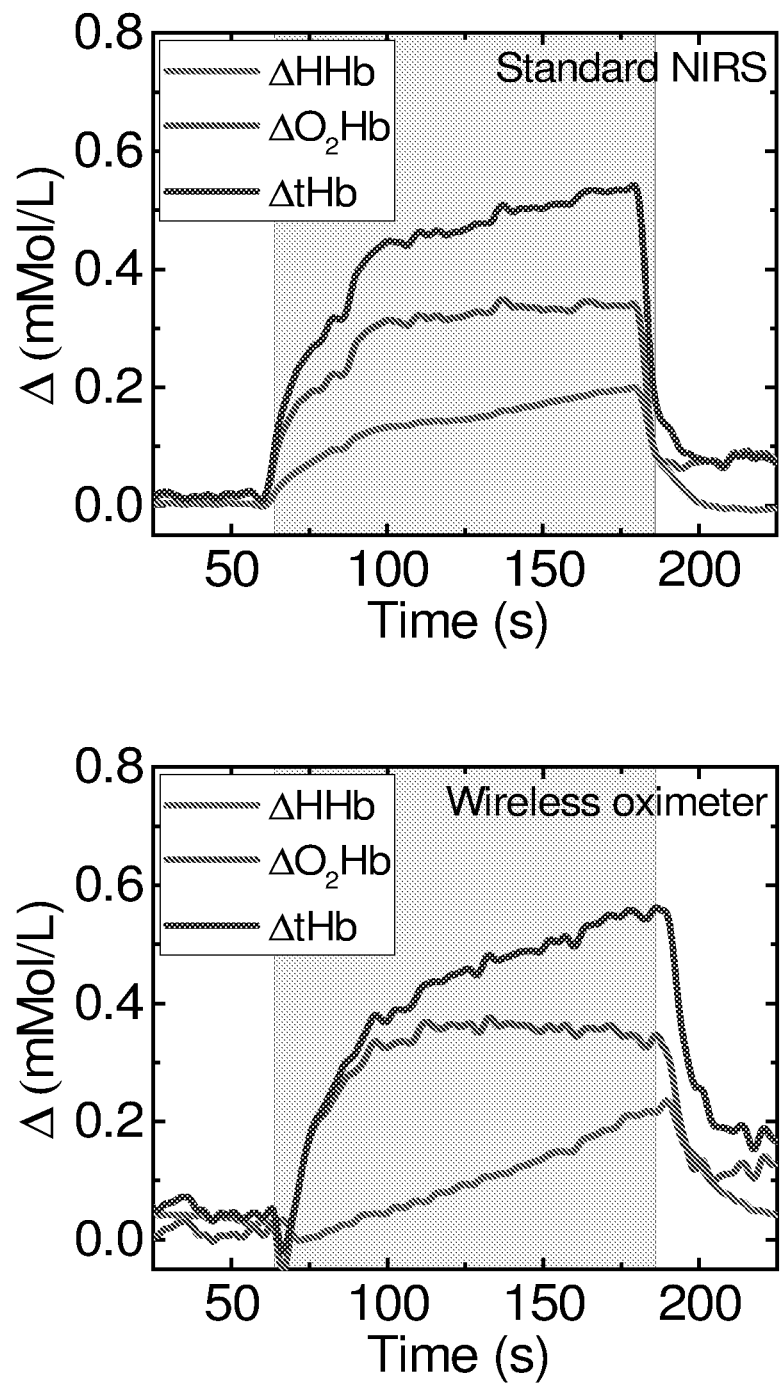
FIG. 43. Venous occlusion technique for assessing peripheral vascular diseases. When venous occlusion is applied to the upper arm or leg by inflating a blood pressure cuff to a pressure of approximately 50 mmHg, this results in an (arterial) inflow of blood but no outflow. The observed increase in blood volume equals the blood flow into the limb, and can be measured with NIRS by monitoring the increase in the tHb signal following occlusion.
Figure 44:
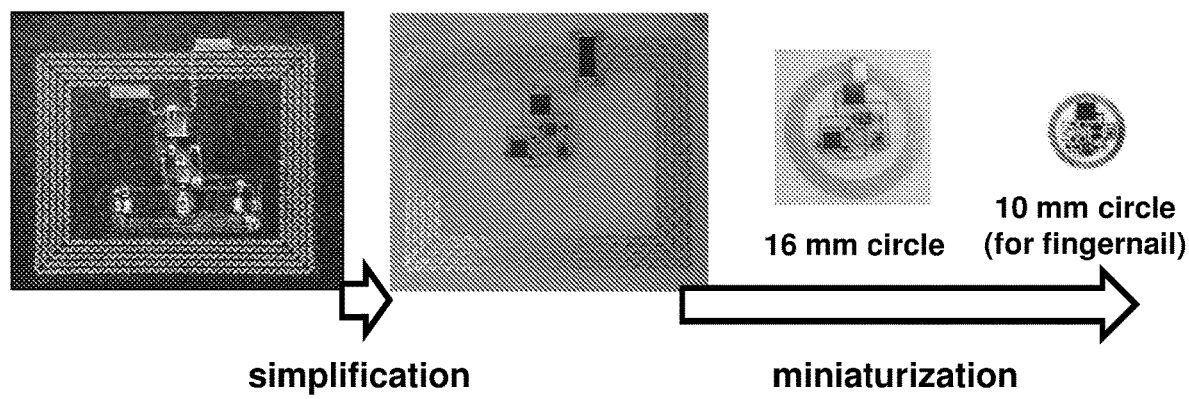
FIG. 44. Pictures of simplified and miniaturized devices. In the simplified device, 4 resistors, 2 capacitors and 2 BJTs are replaced by 1 microcontroller.
Figure 45:
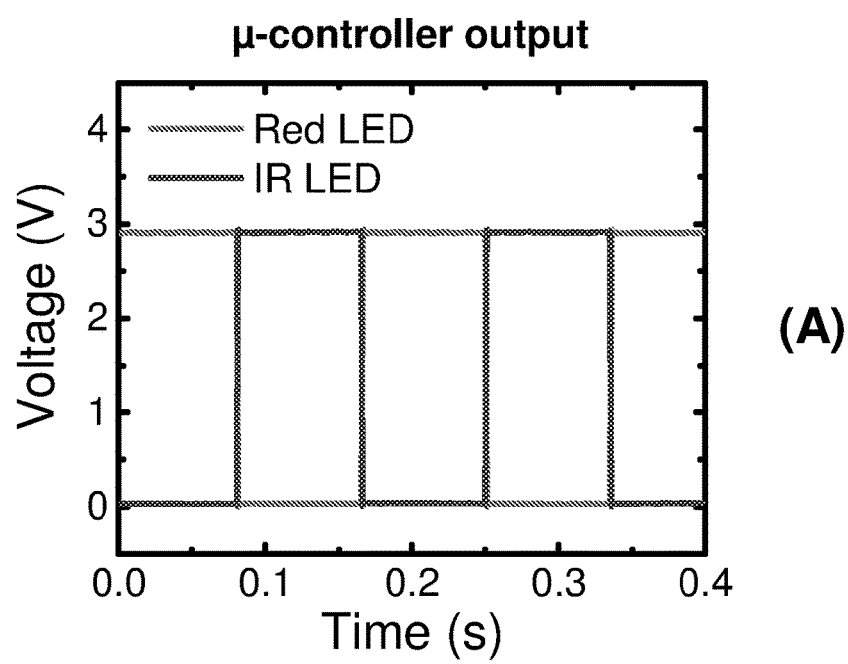
FIG. 45. Graphs showing (A) microcontroller output, (B) LED current and (C) raw voltage for red and IR LEDs versus time.
Figure 46:
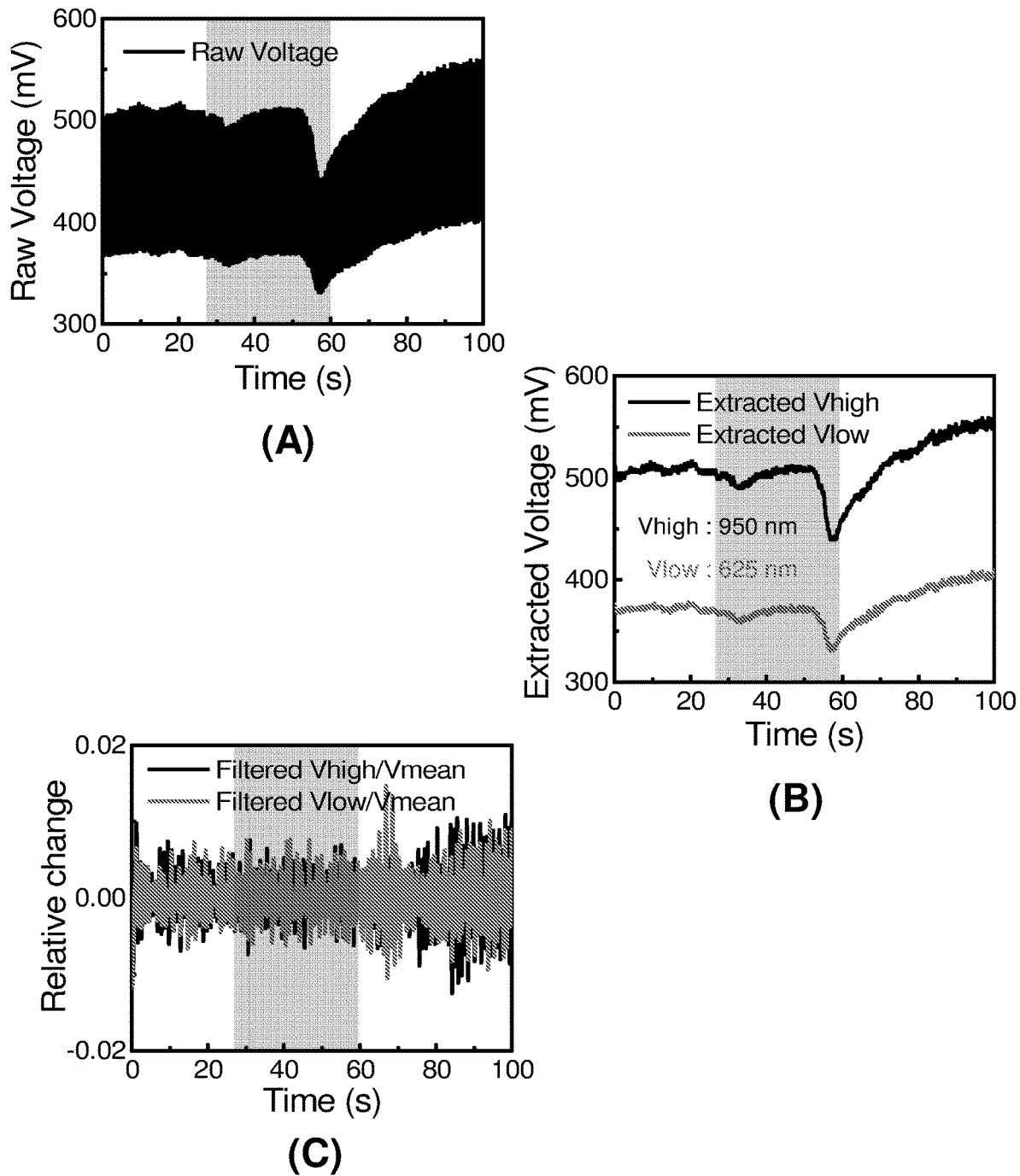
FIG. 46. Graphs showing $SPO_2$ measurements for a breath hold test. (A) raw voltage from red and IR LEDs versus time, (B) extracted Vhigh and Vlow voltage (0.5-3 Hz bandpass filtering), (C) the relative change (Filtered V/Vmean), (D) R coefficient (Red/IR) versus time and (E) $SpO_2$ ($SpO_2$%=A−B*R, the R value increases when the $SpO_2$ value decreases) versus time.

The present wearable and battery-less devices are advantageous to solve both of these problems. They increase wearability through miniaturization and ultra-low modulus, as well as reduce motion artifacts by being directly bonded to the skin or fingernail. Exemplary devices are shown, for example, in FIGS. 39-46.

The working principle of the devices relies on the absorption difference of oxygenated and deoxygenated hemoglobin, the protein that transports oxygen through the body, at infrared (IR) and red light wavelengths. Oxygenated hemoglobin absorbs more red light and less infrared, while deoxygenated hemoglobin absorbs more infrared and less red light.

In embodiments, the devices have both IR and red light sources in the form of miniaturized light emitting diodes (LEDs) that emit light into the fingernail or skin. The light is then reflected back into the detector, located approximately 2 mm from the LEDs, by the surrounding tissue. While travelling through the tissue, the light intensity is attenuated by the adverse absorbance of the IR and red light under pulsation resulting in a distinct signal that allows for the calculation of the heart rate and also the peripheral capillary oxygen saturation (SpO2).

Example 4: Bilirubin Sensor

Infant jaundice occurs because a baby's blood contains an excess of bilirubin, a yellow-colored pigment of red blood cells. Newborns develop more bilirubin than adults due to a higher turnover of red blood cells and a developing liver which, in some individuals, might not be able to remove enough bilirubin from the blood.

Figure 56:
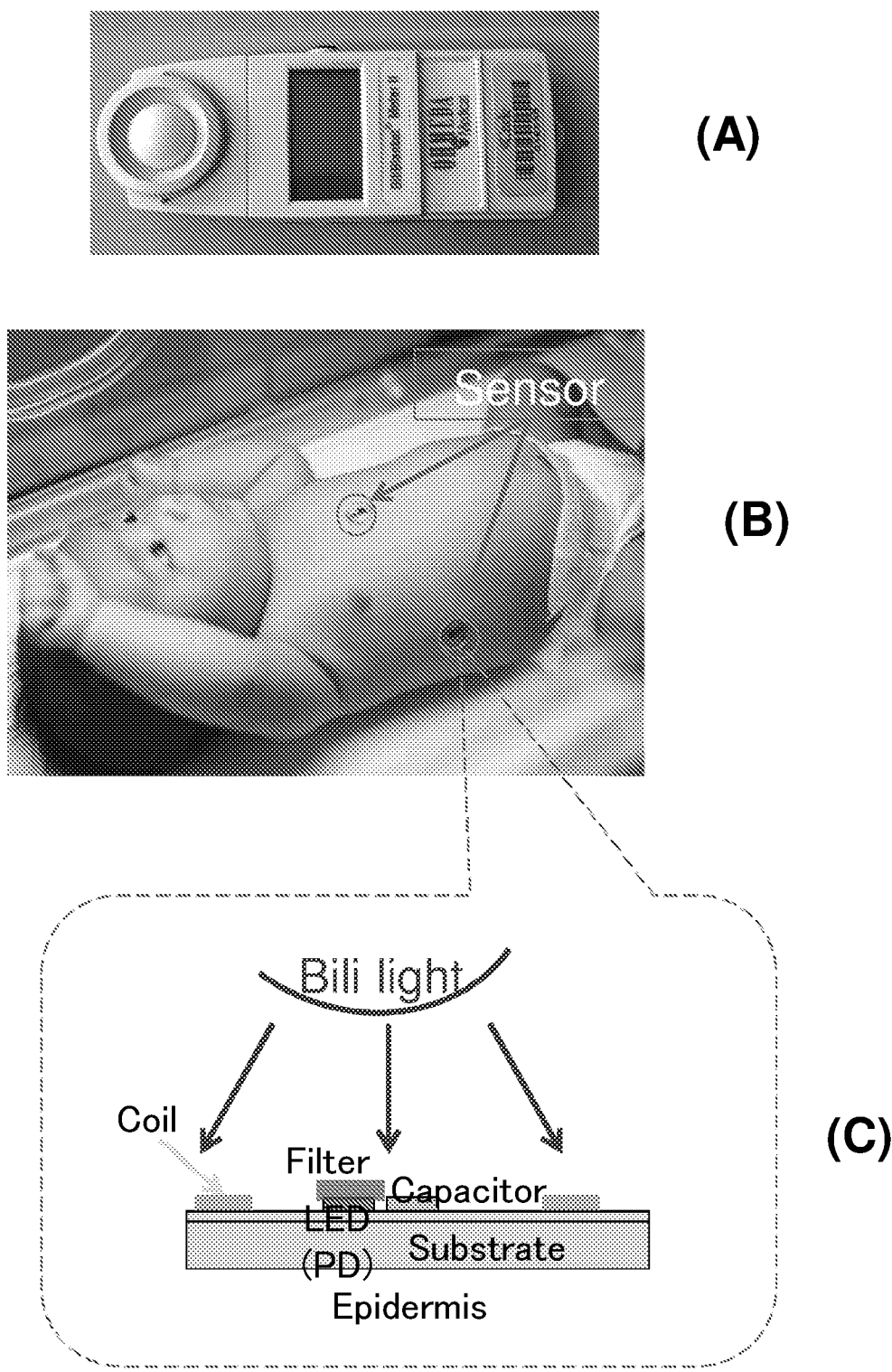
FIG. 56. Schematic of (A) a commercial bili light sensor used to measure intensity before therapy, (B) a baby having two skin-mounted, wireless bili light sensors according to an embodiment of the present invention located on its abdomen, and (C) a cross sectional view of the components of the skin-mounted, wireless bili light sensors, which track exposure in real time during therapy.

Commercial bilirubin sensor devices need a power source or a wired connection and cannot monitor bilirubin levels continuously. The present wearable and battery-less devices can be comfortably mounted on the skin and monitor the bilirubin level continuously in real time. Exemplary devices are shown, for example, in FIGS. 47-49 and 56-58.

The working principle of the devices relies on the absorption difference of the skin at green and blue light. Since people have different skin colors, it is essential to consider the effects from skin color variations. The device includes a set of green and blue LEDs located close to a detector to probe a short path of reflection and another set of LEDs located at a greater distance to probe a long path of reflection. While the short path reflection by the epidermis can assess the skin color, the long path reflection evaluates the bilirubin level.

Example 5: UV Sensor

Effects of UV radiation on the human body have been well established for many years. The drive to increase the public's awareness of both the positive effects (mental wellness, vitamin D synthesis) and negative effects (erythema, cataracts, melanoma, suppression of the immune system) of UV exposure is an ongoing effort. Awareness may be increased by providing a convenient way for individuals to determine the amount of their UV exposure.

Figure 52:
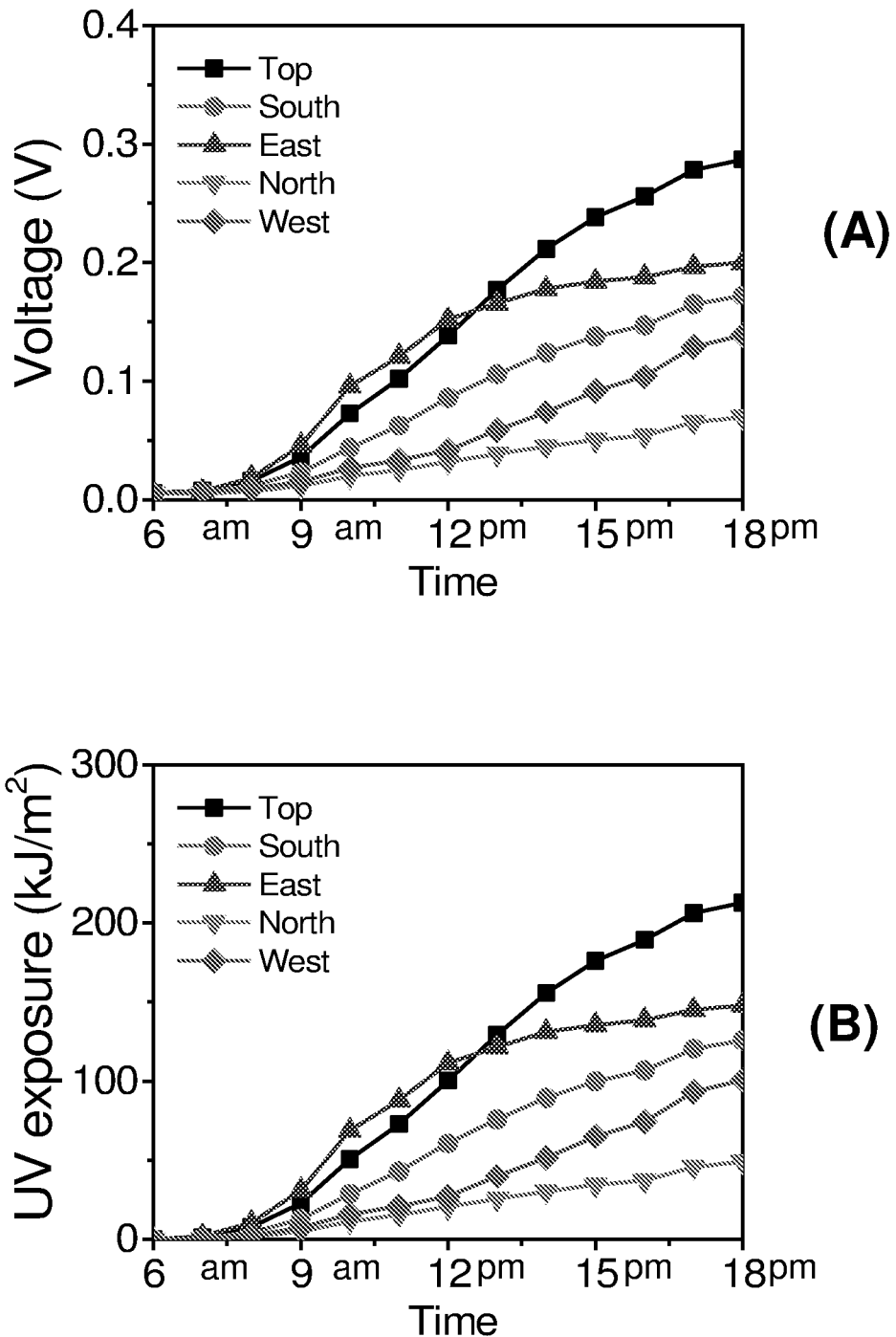
FIG. 52. Graphs of cumulative UV exposure during the test of FIG. 51. (A) Voltage versus time. (B) UV exposure versus time. The cumulative UV-A exposure amounts depend on the mounting location. For example, "East" had more UV-A than "West" during the morning, and less UV-A in the afternoon.

The present wearable, battery-less, and low-cost UV sensor devices can be mounted on the skin, and monitor the amount of UV exposure for individuals with real time UV measurement on demand. Exemplary devices are shown, for example, in FIGS. 50-55.

The devices work by using the photocurrent generated by the UV detector(s) to charge a supercapacitor. An NFC can then analyze and transmit the information to readers such as a smartphone, a tablet, etc. When the device is exposed to UV light, the NFC system readout allows for the evaluation of the cumulative charge(s) which correspond to the UV dose.

Example 6: Bili Light Sensor

Severe jaundice that is not treated can cause deafness, cerebral palsy, or other forms of brain damage. Treatment of infant jaundice often is not necessary, and most cases that need treatment respond well to noninvasive therapy. Phototherapy refers to the use of light to convert bilirubin molecules in the body into water soluble isomers that can be excreted by the body.

Current devices check the bili light intensity only before the therapy and cannot track the exposed intensity during the therapy. The present wearable and wireless sensors can be mounted on the skin and measure the exposed energy exactly on the location of impact on the skin in real time. Exemplary devices are shown, for example, in FIGS. 47-49 and 56-58.

The devices have a bili light detector, a supercapacitor, and an NFC which are similar to the UV sensor of Example 5 and measure the bili light intensities from different locations at the same time, which may provide spatial or spatiotemporal data indicative of bili light exposure.

Example 7: Particulate Pollution Sensing

Current devices that are used to measure air quality are very bulky and are typically not portable. However, with cities growing quickly, air pollution is an increasingly important topic. Especially of interest is the dust concentration or particulate pollution concentration, not only in crowded cities but also at work sites, such as construction and mining sites.

The present device is a body worn sensor system comprising a passive image analysis based system as well as a real time analysis unit. The passive sensor relies on a defined surface made out of a primary sticky layer of silicone that is covered with a perforated epoxy layer with defined holes with sub millimeter diameter exposing the sticky surface underneath. In a dusty environment the surface will get covered with dust that will only stick permanently to the exposed sticky layer, which will slowly accumulate dust. By wiping the sensor surface the excess dust will get removed from the non-sticking surfaces exposing a contrast between the predominantly white particles and virgin black sticky layer, visible through the transparent epoxy layer. By taking a picture with a smart phone camera, post image processing can be employed to estimate the accumulated dust exposure.

Figure 60:
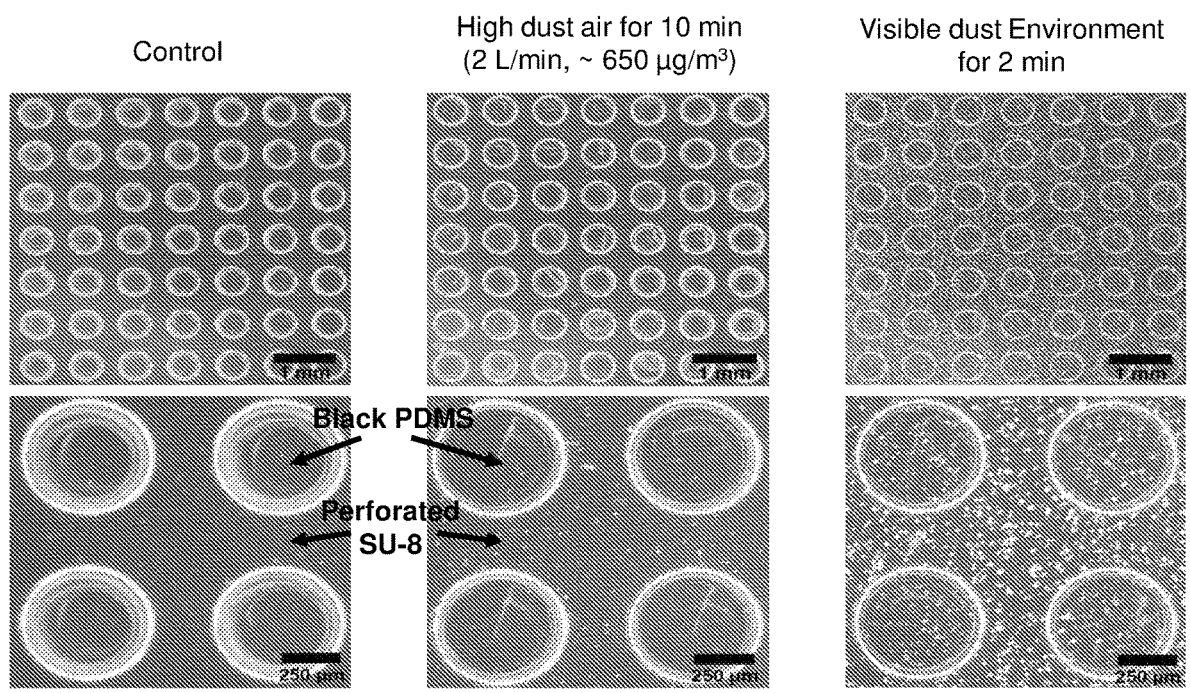
FIG. 60. Micrographs of a passive dust sensor: (A) control, (B) a high dust air for 10 minutes (2 L/min, ~650 μg/m$^3$) and (C) a visible dust environment for 2 minutes.
Figure 61:
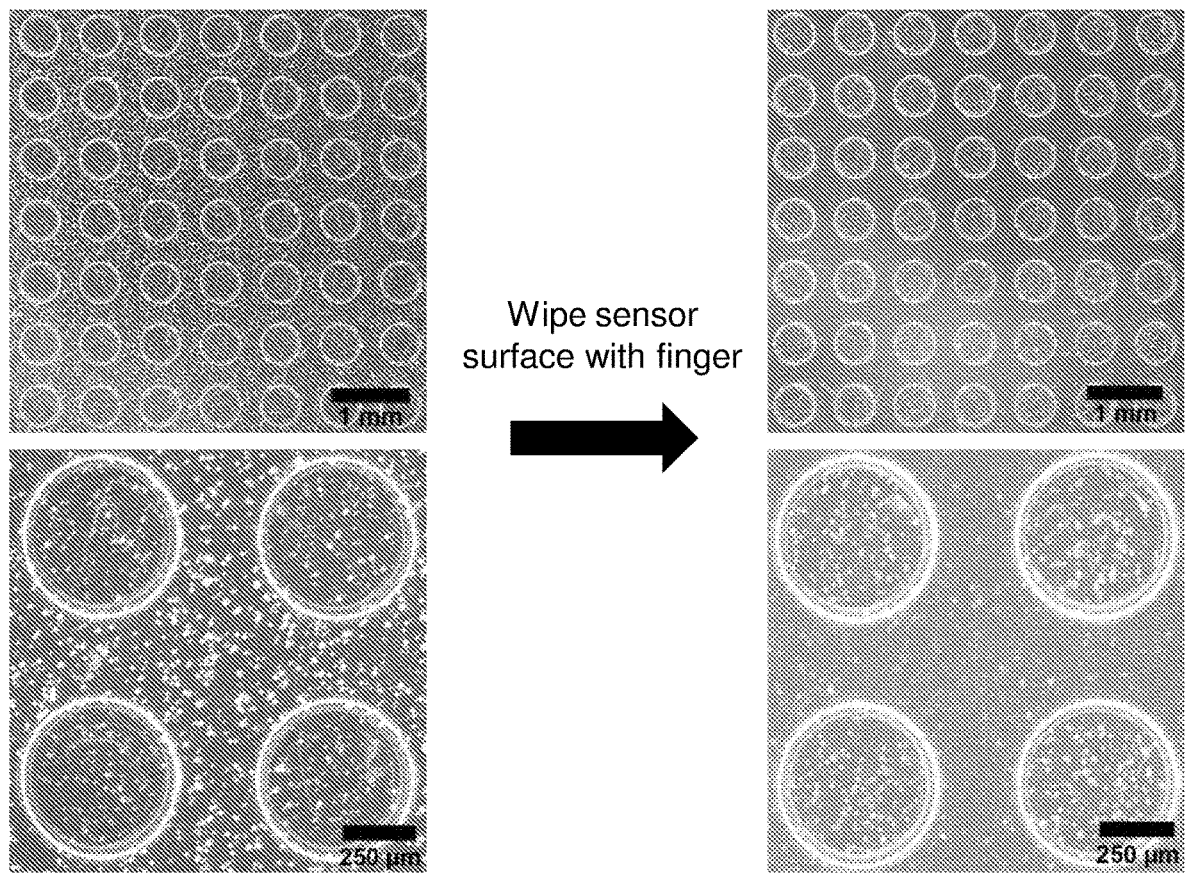
FIG. 61. Micrographs illustrating the effect of wiping the sensor surface prior to detecting the presence of dust on the substrate.
Figure 63:
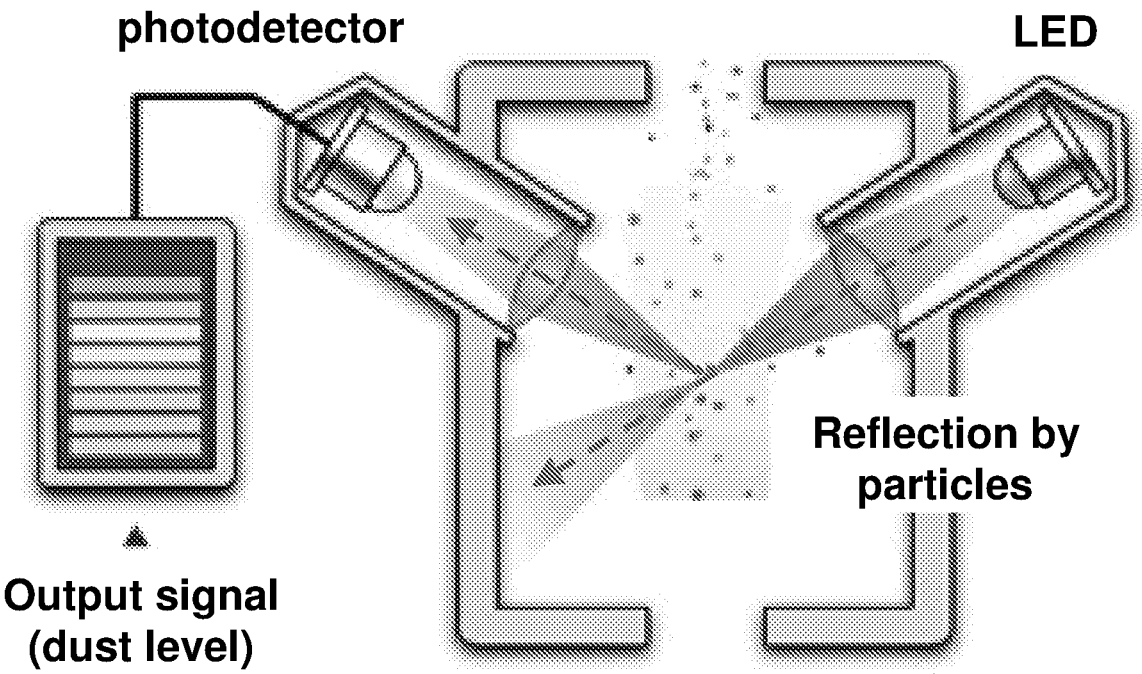
FIG. 63. Schematic illustrating the working principle of an optical dust detector.
Figure 64:
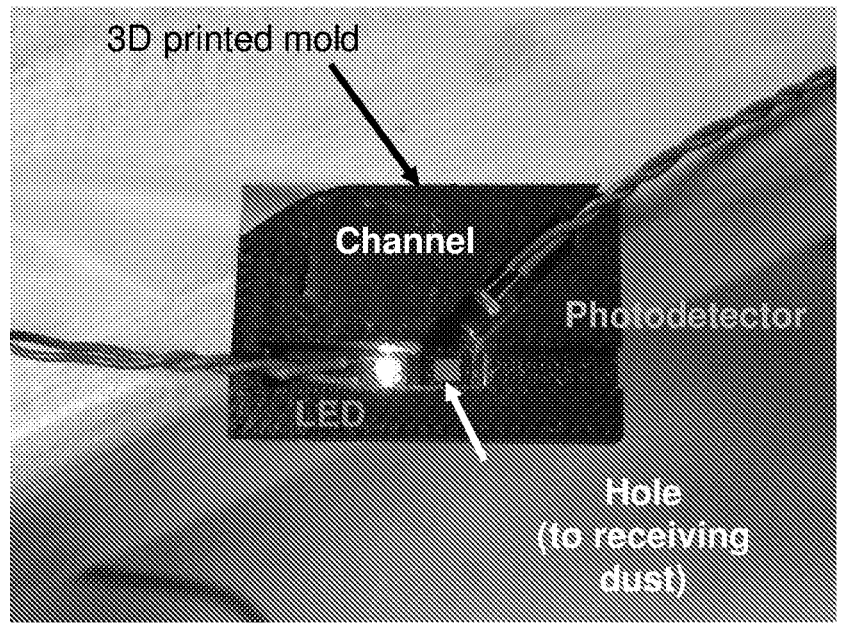
FIG. 64. Photograph of an optical dust sensor preliminary test.

The real time measurement makes use of scattering and reflection of light on particles by illuminating a channel with an LED which is indirectly connected to a secondary, optically isolated channel with a detector. The detector can only register light when a particle is introduced in the primary channel reflecting or scattering the light into the secondary channel. By measuring the light intensity, it is possible to calculate the current dust exposure. Exemplary devices are shown, for example, in FIGS. 59-65.

Example 8: Tissue Mounted NFC Device for Pollution Monitoring

The invention provides, for example, miniature tissue-mounted near field communication (NFC) devices providing a unique service platform for pollution monitoring. The materials, design, and circuit integration enable the art of biocompatible NFC technology. In some embodiments, the built-in NFC technology offers individual users, meteorologists, doctors, environmentalists, farmers, researchers, and/or merchants a way to measure contaminants in the atmosphere. The invented NFC devices of this aspect are placed on a fingernail, tissue, plant stem, and/or leaf. The invented device is able to wirelessly communicate with readers that use NFC antennas. The electrochemical sensor is able to detect levels of carbon monoxide, sulfur dioxide, chlorofluorocarbons, and nitrogen oxides.

In some embodiments, for privacy, some versions of the invention have a devoted chip that stores an encrypted identification number that is unique to each individual device. In addition, the chip has action-specific security codes that change constantly. In some embodiments, the encrypted device number helps keep the digital information private.

In some embodiments, devices are waterproof and remain operational for several days or months. The systems of this aspect of the invention are able to work in conjunction with computer or mobile applications. In some embodiments, if removed from the tissue, the invented device is permanently disabled and all private information is destroyed.

Example 9: Finger and Toenail Mounted NFC Device for Diabetes

The invention provides, for example, tissue mounted near field communication (NFC) devices providing a unique service platform for patients diagnosed with diabetes. The materials, design, and circuit integration enable the art of biocompatible NFC technology. In some embodiments, the built-in NFC technology serves as a digital replacement for the diabetic accessories. The fingernail-mounted devices of this aspect are able to wirelessly communicate with point of access readers that use NFC antennas. The readers include but are not limited to smartphones, hand-held electronic devices, and/or computers. The fingernail-mounted or tissue-mounted devices of this aspect offer diabetic patients additional bio-sensing modalities that measure temperature, pH levels, glucose, insulin levels, pulse-oximetry, heart rate, respiratory rate, blood pressure, ECG, EOG, EEG, and EMG.

In some embodiments, for privacy, the system of the invention has a devoted chip that stores an encrypted identification number that is unique to each individual device. In addition, the chip has action-specific security codes that change constantly. The encrypted device numbers and security codes help keep patient health-care information private.

Diabetic patients and doctors are able to wirelessly monitor important vital signs and symptoms. In some embodiments, the devices are waterproof and remain operational for several days or months. The systems of this aspect of the invention are able to work in conjunction with computer and mobile applications developed specifically for health care monitoring. In some embodiments, if removed from the nail or tissue, the invented device is permanently disabled and all private information is destroyed.

Example 10: Finger and Toenail Mounted NFC Device for Digital Health Monitoring

The invention provides, for example, fingernail mounted near field communication (NFC) devices providing a unique solution for digital health monitoring. The materials, design, and circuit integration enable the art of biocompatible NFC technology. In some embodiments, the built-in NFC technology serves as a digital replacement for physical health monitoring. The fingernail-mounted or tissue-mounted devices of this aspect are able to wirelessly communicate with point of access readers that use NFC antennas. The fingernail-mounted or tissue-mounted devices of this aspect offer users bio-sensing modalities that measure temperature, pH levels, glucose, pulse-oximetry, heart rate, respiratory rate, blood pressure, ECG, EOG, EEG, and EMG.

In some embodiments, for privacy, the systems of the invention have a devoted chip that stores an encrypted identification number that is unique to each individual device. In addition, the chip has action-specific security codes that change constantly. The encrypted device number helps keep patient health-care information private.

Individual users are no longer at risk of exposing their health-care information to unauthorized third parties or by-standers. In some embodiments, devices are waterproof and remain operational for several days or months. The systems of this aspect of the invention are able to work in conjunction with mobile phone applications developed specifically for mobile health monitoring. In some embodiments, if removed from the nail or tissue, the invented device is permanently disabled and all private information is destroyed.

Example 11: An Indirect Tissue Mounted NFC Device Application for Prosthetic Temperature Monitoring The invention provides, for example, miniature near field communication (NFC) devices providing a unique solution for prosthetic temperature monitoring. The materials, design, and circuit integration enable the art of biocompatible NFC technology. In some embodiments, the built-in NFC technology serves as a digital replacement for temperature sensing electrodes with copper wire leads. The invented NFC devices of this aspect function as an integrated temperature sensor that is placed on the inner surface of prosthetic limbs. The invented device of this aspect is able to wirelessly communicate with smartphone readers that use NFC antennas.

In some embodiments, for privacy, the invention has a devoted chip that stores an encrypted identification number that is unique to each individual device. In addition, the chip has action-specific security codes that change constantly. The encrypted device number helps keep patient health-care information private. Individual patients, hospital staff, and insurance providers are the only users with access to the health care information.

Individual users are no longer at risk of exposing their name or health-care information to third parties or by-standers. In some embodiments, devices are waterproof and remain operational for several days or months. The systems of this aspect of the invention are able to work in conjunction with computer or mobile applications developed specifically for authentication purposes. In some embodiments, if removed from the nail or tissue, the invented device is permanently disabled and all private information is destroyed.

Example 12: Tissue Mounted NFC Device for UV Sensing

The invention provides, for example, miniature tissue-mounted near field communication (NFC) devices providing a unique service platform for UV exposure monitoring. The materials, design, and circuit integration enable the art of biocompatible NFC technology. In some embodiments, the built-in NFC technology offers individual users, dermatologists, farmers, researchers, and/or merchants a way to measure UV exposure times and doses. The invented NFC devices of this aspect are placed on a fingernail, tissue, plant stem, and/or leaf. The invented device is able to wirelessly communicate with readers that use NFC antennas.

In some embodiments, for privacy, some versions of the invention have a devoted chip that stores an encrypted identification number that is unique to each individual device. In addition, the chip has action-specific security codes that change constantly. In some embodiments, the encrypted device number helps keep the digital information private.

In some embodiments, devices are waterproof and remain operational for several days or months. The systems of this aspect of the invention are able to work in conjunction with computer or mobile applications. In some embodiments, if removed from the tissue, the invented device is permanently disabled and all private information is destroyed.

Example 13: Tissue Mounted NFC Device for Activity Monitoring

The invention provides, for example, miniature tissue-mounted near field communication (NFC) devices providing a unique service platform for activity monitoring. The materials, design, and circuit integration enable the art of biocompatible NFC technology. In some embodiments, the built-in NFC technology offers individual users, doctors, researchers, and/or personal trainers a way to measure the instantaneous and/or cumulative activity level of a user (e.g., instantaneous or cumulative calories burned). The invented NFC devices of this aspect may contain a motion sensor, such as an accelerometer or gyroscope, and they are typically placed on a fingernail, tissue and/or mounting platform (e.g., clothing or jewelry). The invented device is able to wirelessly communicate with readers that use NFC antennas.

In some embodiments, for privacy, some versions of the invention have a devoted chip that stores an encrypted identification number that is unique to each individual device. In addition, the chip has action-specific security codes that change constantly. In some embodiments, the encrypted device number helps keep the digital information private.

In some embodiments, devices are waterproof and remain operational for several days or months. The systems of this aspect of the invention are able to work in conjunction with computer or mobile applications. In some embodiments, if removed from the tissue, the invented device is permanently disabled and all private information is destroyed.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components and method steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomer and enantiomer of the compound described individually or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when compositions of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element, elements, limitation or limitations which is/are not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents of any such materials and methods are intended to be included in this invention. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A UV monitoring system for measuring a radiant exposure or flux of incident UV electromagnetic radiation, the system comprising:
 a near-field coil for wirelessly coupling the system with an external electronic device;
 a substrate; and
 an electronic device supported by said substrate, wherein said electronic device comprises:
  a transducer including one or more light emitting diodes (LEDs), the one or more LEDs configured to convert at least a portion of said incident UV electromagnetic radiation into an electrical current, wherein the current is characteristic of said radiant exposure or flux of said incident UV electromagnetic radiation, wherein absorption of the incident UV electromagnetic radiation by the one or more LEDs provides at least a portion of the power for said measurement of the radiant exposure or flux of said incident UV electromagnetic radiation;
  a capacitor to store charge from the one or more LEDs; and
  an NFC chip configured to assess charge on the capacitor and transmit UV exposure data to the external electronic device
 wherein the near-field coil encircles the transducer, the capacitor and the NFC chip on the substrate.

2. The system of claim 1, wherein absorption of the incident electromagnetic radiation by the electronic device provides at least 50% of the power for said measurement of the radiant exposure or flux of said incident UV electromagnetic radiation.

3. The system of claim 1, wherein said electronic device does not include a battery or solar cell configured to provide power to said electronic device.

4. The system of claim 1, wherein said system continuously monitors said radiant exposure or flux of incident UV electromagnetic radiation received by said electronic device.

5. The system of claim 1, wherein said system is wearable on clothing, jewelry or a faux nail.

6. The system of claim 1, wherein an inner surface of said substrate is capable of being conformably integrated with a tissue surface.

7. The system of claim 1, wherein said electronic device further comprises one or more optical filters positioned to optically filter said incident UV electromagnetic radiation received by said system.

8. The system of claim 1, further comprising a temperature sensor.

9. The system of claim 1, further comprising a power source selected from the group consisting of a battery, an energy harvester, a solar cell, a piezoelectric element and any combination of these.

10. The system of claim 1, wherein the capacitor is a first capacitor, the system comprising:
 a first LED, the first LED being configured to detect UVA electromagnetic radiation;
 the first capacitor connected in parallel to the first LED, the first capacitor being configured to store charge from the first LED;
 a second LED, the second LED being configured to detect UVB electromagnetic radiation;
 a second capacitor connected in parallel to the second LED, the second capacitor being configured to store charge from the second LED; and
 a trigger, wherein the first and second capacitors are each connected in parallel to the trigger to allow discharge of the first and second capacitors;
 the NFC chip being configured to assess the charge on each capacitor and transmit UVA and UVB exposure data to the external electronic device, wherein UVA exposure is correlated to the total charge on the first capacitor and wherein UVB exposure is correlated to the total charge on the second capacitor.

11. The system of claim 10, wherein the first LED absorbs electromagnetic radiation having wavelengths between 320 nm and 400 nm and the second LED absorbs electromagnetic radiation having wavelengths between 280 nm and 320 nm.

12. The system of claim 1, wherein said electronic device is waterproof.

13. The system of claim 1, wherein said system has a lateral area footprint selected from the range of 10 $mm^2$ to 500 $mm^2$.

14. The system of claim 1, wherein said system has an average modulus selected from the range of 10 kPa to 100 GPa.

15. The system of claim 1, wherein said system has a net bending stiffness selected from the range of 0.1 nN m to 1 N m.

16. The system of claim 1, wherein said system has an average thickness selected from the range of 5 microns to 5 millimeters.

17. The system of claim 1, wherein said near-field coil has a diameter selected from the range of 500 microns to 20 millimeters.

18. The system of claim 17, wherein said UV monitoring system has a diameter less than 9 millimeters.

19. The system of claim 1, wherein said near-field coil has an annular shape, an elliptical shape, or a rectangular shape.

20. A method of making a UV monitoring system for measuring a radiant exposure or flux of incident UV electromagnetic radiation, comprising:
 providing a near-field coil for wirelessly coupling the system with an external electronic device;
 providing a substrate; and
 providing an electronic device supported by said substrate, wherein said electronic device comprises:
  a transducer including one or more light emitting diodes (LEDs), the one or more LEDs configured to convert at least a portion of said incident UV electromagnetic radiation into an electrical current, wherein the current is characteristic of said radiant exposure or flux of said incident UV electromagnetic radiation; wherein absorption of the incident UV electromagnetic radiation provides at least a portion of the power for said measurement of the radiant exposure or flux of said incident UV electromagnetic radiation;
  a capacitor to store charge from the one or more LEDs; and
  an NFC chip configured to assess charge on the capacitor and transmit UV exposure data to the external electronic device
 wherein the near-field coil encircles the transducer, the capacitor and the NFC chip on the substrate.

21. A method of using a UV monitoring system for measuring a radiant exposure or flux of incident UV electromagnetic radiation, comprising:
   mounting the UV monitoring system on a subject, said monitoring system comprising:
   a near-field coil for wirelessly coupling the system with an external electronic device;
   a substrate; and
   an electronic device supported by said substrate, wherein said electronic device comprises:
      a transducer including one or more light emitting diodes (LEDs), the one or more LEDs configured to convert at least a portion of said incident UV electromagnetic radiation into an electrical current, wherein the current is characteristic of said radiant exposure or flux of said incident UV electromagnetic radiation; wherein absorption of the incident UV electromagnetic radiation by the one or more LEDs provides at least a portion of the power for said measurement of the radiant exposure or flux of said incident UV electromagnetic radiation;
      a capacitor; and
      an NFC chip;
      wherein the near-field coil encircles the transducer, the capacitor and the NFC chip on the substrate;
   exposing said one or more LEDs of said UV monitoring system to said UV electromagnetic radiation;
   charging the capacitor via the electrical current from the one or more LEDs; and
   assessing the charge on the capacitor and transmitting UV exposure data to the external electronic device via the NFC chip.

22. The method of claim 21, wherein said UV monitoring system is a wearable or a tissue-mounted system provided on a subject.

23. The method of claim 22, wherein said UV monitoring system is provided on the skin or finger nail of said subject.

* * * * *